United States Patent
Schnermann et al.

(10) Patent No.: US 10,561,729 B2
(45) Date of Patent: Feb. 18, 2020

(54) NEAR-IR LIGHT-CLEAVABLE CONJUGATES AND CONJUGATE PRECURSORS

(71) Applicant: The United States of America, as represented by the Secretary, Department of Health and Human Services, Bethesda, MD (US)

(72) Inventors: Martin John Schnermann, Rockville, MD (US); Roger Rauhauser Nani, Frederick, MD (US); Alexander Patrick Gorka, Frederick, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/323,747

(22) PCT Filed: Aug. 7, 2017

(86) PCT No.: PCT/US2017/045694
§ 371 (c)(1),
(2) Date: Feb. 6, 2019

(87) PCT Pub. No.: WO2018/031448
PCT Pub. Date: Feb. 15, 2018

(65) Prior Publication Data
US 2019/0167793 A1    Jun. 6, 2019

Related U.S. Application Data

(60) Provisional application No. 62/373,666, filed on Aug. 11, 2016.

(51) Int. Cl.
| | |
|---|---|
| A61K 49/00 | (2006.01) |
| A61K 31/4545 | (2006.01) |
| C07D 209/10 | (2006.01) |
| A61K 41/00 | (2020.01) |
| A61P 35/00 | (2006.01) |
| A61K 47/54 | (2017.01) |
| A61K 47/68 | (2017.01) |

(52) U.S. Cl.
CPC ........ *A61K 41/0042* (2013.01); *A61K 47/545* (2017.08); *A61K 47/6829* (2017.08); *A61K 47/6845* (2017.08); *A61K 49/0032* (2013.01); *A61K 49/0058* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 6,448,008 | B1 | 9/2002 | Caputo et al. |
| 7,198,778 | B2 | 4/2007 | Achilefu et al. |
| 8,344,158 | B2 | 1/2013 | Achilefu et al. |
| 2004/0081622 | A1 | 4/2004 | Achilefu et al. |
| 2004/0141920 | A1 | 7/2004 | Achilefu et al. |
| 2008/0031823 | A1 | 2/2008 | Bornhop et al. |
| 2008/0050316 | A1 | 2/2008 | Adams et al. |
| 2015/0335765 | A1 | 11/2015 | Chung et al. |
| 2018/0273758 | A1 | 9/2018 | Schnermann et al. |

FOREIGN PATENT DOCUMENTS

| | | |
|---|---|---|
| JP | 2011-051961 A | 3/2011 |
| KR | 10-1494639 B1 | 2/2015 |
| WO | WO 2007/005222 A2 | 1/2007 |
| WO | WO 2011/119114 A1 | 9/2011 |
| WO | WO 2013/036543 A2 | 3/2013 |
| WO | WO 2014/144702 A3 | 9/2014 |

(Continued)

OTHER PUBLICATIONS

Bio et al., "Site-Specific and Far-Red-Light-Activatable Prodrug of Combretastatin A-4 Using Photo-Unclick Chemistry," *Journal of Medicinal Chemistry*, 2013, 56:3936-3942.
Biswas et al. "Biomolecular robotics for chemomechanically driven guest delivery fuelled by intracellular ATP." *Nature Chemistry* 2013, 5:613-620.
Bouteiller et al. "Novel water-soluble near-infrared cyanine dyes: synthesis, spectral properties, and use in the preparation of internally quenched fluorescent probes." *Bioconjugate Chemistry*, 2007, 18:1303-1317.
Choi et al., "Synthesis and In Vivo Fate of Zwitterionic Near-Infrared Fluorophores," author manuscript, published in *Angewandte Chemie International Edition*, 2011, 50(28):6258-6263.

(Continued)

*Primary Examiner* — Mark Halvorson
*Assistant Examiner* — Kauser M Akhoon
(74) *Attorney, Agent, or Firm* — Klarquist Sparkman, LLP

(57) ABSTRACT

Embodiments of near-infrared light-cleavable heptamethine cyanine-based conjugates, particularly targeting agent-drug conjugates, according to Formula I and conjugate precursors are disclosed. The disclosed targeting agent-drug conjugates are useful for targeted delivery and release of a drug. Methods of making and using the conjugates and precursors also are disclosed.

11 Claims, 12 Drawing Sheets

(56) References Cited

FOREIGN PATENT DOCUMENTS

| WO | WO 2014/149069 A1 | 9/2014 |
|---|---|---|
| WO | WO 2017/027721 A1 | 2/2017 |

OTHER PUBLICATIONS

Choi et al., "Targeted zwitterioinic near-infrared fluorophores for improved optical imaging" *Nat. Biotechnol.*, 2013, 31(2):1-16.

Gorka et al. "A Near-IR Uncaging Strategy Based on Cyanine Photochemistry," author manuscript, published in *Journal of the American Chemical Society*, 2014, 136:14153-14159.

Gorka et al. "Harnessing cyanine photooxidation: from slowing photobleaching to near-IR uncaging," *Current Opinion in Chemical Biology*, 2016, 33:117-125.

Hilderbrand et al., "Monofunctional near-infrared fluorochromes for imaging applications," *Bioconjugate Chemistry*, 2005, vol. 16, pp. 1275-1281.

International Search Report and Written Opinion for PCT/US2017/045694 dated Nov. 7, 2017, 11 pp.

Lim et al., "Tunable heptamethine-azo dye conjugate as an NIR fluorescent probe for the selective detection of mitochondrial glutathione over cysteine and homocysteine," *Journal of the American Chemical Society*, 2014, 136:7018-7025.

Mitsunaga et al., "Cancer cell—selective in vivo near infrared photoimmunotherapy targeting specific membrane molecules," *Nature Medicine*, 2011, 17(12):1685-1692.

Nani et al., "In Vivo Activation of Duocarmycin-Antibody Conjugates by Near-Infrared Light," *ACS Central Science*, 2017, 3(4):329-337.

Nani, et al., "N- to O- Rearrangement of Cyanines: Synthesis of Stable NIR Fluorophores," Chemical Biology Laboratory, National Cancer Institute, 1 page (Sep. 24, 2014).

Nani et al., "Near-IR Light-Mediated Cleavage of Antibody-Drug Conjugates Using Cyanine Photocages,"*Angewandte Chemie International Edition*, 2015, 54(46):13635-13638.

Narayanan et al., "A new method for the synthesis of heptamethine cyanine dyes: synthesis of new near-infrared fluorescent labels, " Journal of Organic Chemistry, 1995, 60:2391-2395.

Nkepang et al., "Folate Receptor-Mediated Enhanced and Specific Delivery of Far-Red Light-Activatable Prodrugs of Combretastatin A-4 to FR-Positive Tumor," *Bioconjugate Chemistry*, 2014, 25:2175-2188.

Pascal et al. "Expanding the polymethine paradigm: evidence for the contribution of a bis-dipolar electronic structure," *The Journal of Physical Chemistry*, 2014, 118:4038-4047.

Peng et al., "Heptamethine cyanine dyes with a large Stokes shift and strong fluorescence: a paradigm for excited-state intramolecular charge transfer," *Journal of the American Chemical Society*, 2005, 127:4170-4171.

Shealy et al., "Synthesis, chromatographic separation, and characterization of near-infrared-labeled DNA oligomers for use in DNA sequencing," *Anal. Chem.* 1995, 67:247-251.

Shell et al., "Tunable Visible and Near-IR Photoactivation of Light-Responsive Compounds by Using Fluorophores as Light-Capturing Antennas," *Angewandte Chemie International Edition*, 2014, 53:875-878.

Strekowski et al., "Water-soluble pH-sensitive 2,6-bis(substituted ethylidene)-cyclohexanone/hydroxy cyanine dyes that absorb in the visible/near-infrared regions," *Journal of Heterocyclic Chemistry* 2004, 41: 227-232.

Xing et al., "Synthesis of polypeptide conjugated with near infrared fluorescence probe and doxorubicin for pH-responsive and image-guided drug delivery," *Journal of Material Chemistry* 2012, 22:22290-22300.

Yang et al., "Folate-Based Near-Infrared Fluorescent Theranostic Gemcitabine Delivery," *Journal of the American Chemical Society* Jul. 24, 2013, 135(31):11657-11662.

Zaheer et al., "IRDye78 conjugates for near-infrared fluorescence imaging," *Molecular Imaging* 2002, 1(4):354-364.

Zhang et al., "Synthesis and evaluation of polyhydroxylated near-infrared carbocyanine molecular probes," *Org. Lett.* 2004, 6(12):2067-2070.

Scheme 2

Scheme 3

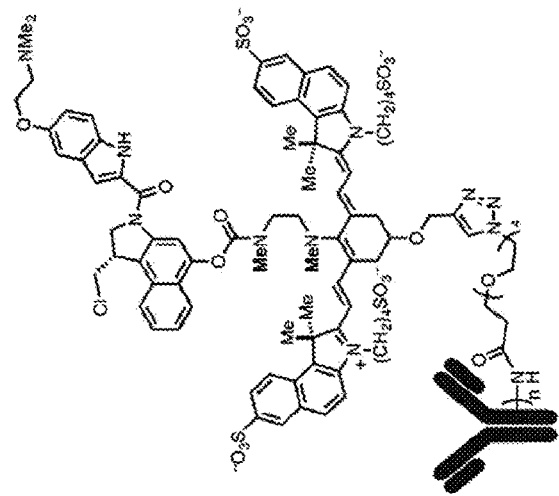
FIG. 5
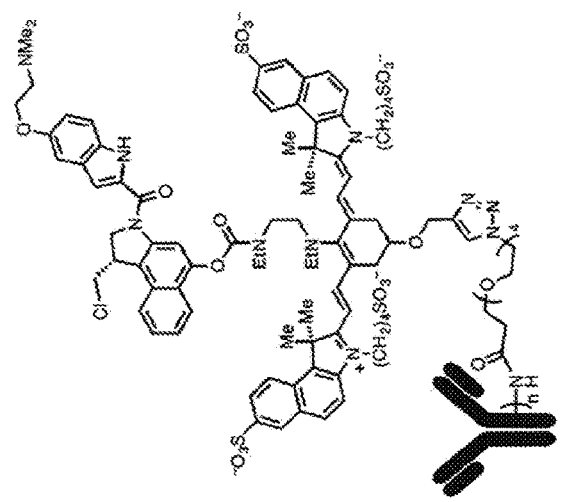
FIG. 6
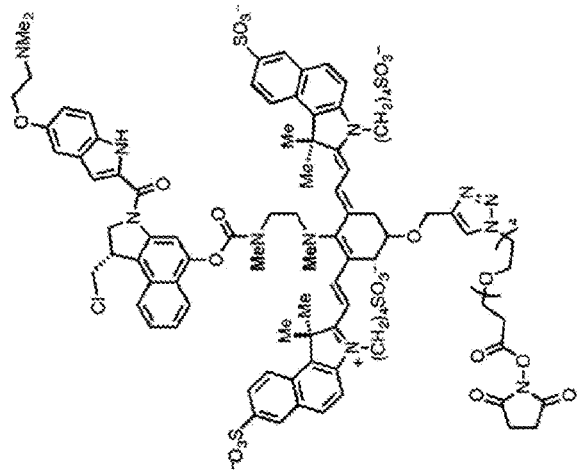
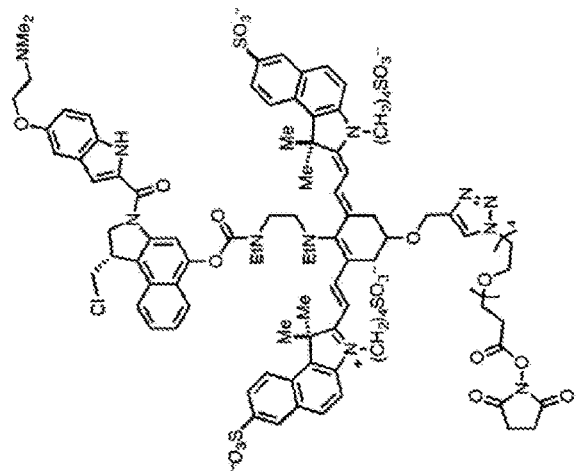

NEAR-IR LIGHT-CLEAVABLE CONJUGATES AND CONJUGATE PRECURSORS

CROSS REFERENCE TO RELATED APPLICATION

This is the U.S. National Stage of International Application No. PCT/US2017/045694, filed Aug. 7, 2017, which was published in English under PCT Article 21(2), which in turn claims the benefit of U.S. Provisional Application No. 62/373,666, filed Aug. 11, 2016, which is herein incorporated by reference in its entirety.

FIELD

This disclosure concerns conjugates, particularly targeting agent-drug conjugates comprising heptamethine cyanine fluorophores, conjugate precursors, and methods of making and using the conjugates.

BACKGROUND

The recent clinical success of antibody-drug conjugates has validated the benefits of combining macromolecule and small molecule therapeutics. Within this exciting area, a remaining challenge is to identify linker strategies that provide improved cleavage selectivity with site-specific drug delivery. An appealing solution would be to develop antibody-drug cleavage chemistry that relies on an external stimulus which can be applied in a site-specific fashion.

Light in the near-IR range (e.g., 650-900 nm) has unique potential in this context. These wavelengths exhibit significant tissue penetration, minimal toxicity, and, moreover, are clinically validated for both diagnostic and therapeutic applications. Near-IR fluorescence imaging is routine in certain clinical contexts and innovative applications, such as methods to optically define tumor margins during surgery, are being developed. Light-based therapeutic modalities using phototoxic small molecules have an extensive history in the treatment of cancer and skin disorders.

Existing approaches, however, rely on intracellular processes that use endogenous, often enzymatic, reactions with little inherent tumor selectivity. As a consequence, benign tissue uptake of the antibody through either antigen-specific or antigen-independent mechanisms can lead to off-target drug release with resulting dose-limiting toxicities, especially in organs responsible for catabolizing antibody-drug conjugates. Moreover, premature release in circulation can be a significant issue.

SUMMARY

This disclosure concerns embodiments of targeting agent-drug conjugates comprising heptamethine cyanine fluorophores, precursors of the conjugates, and methods of making and using the conjugates and precursors. The targeting agent promotes preferential or targeted delivery of the drug to a target site. Embodiments of the disclosed conjugates undergo photodegradation when irradiated with near-infrared light, which produces intramolecular cleavage and release of the drug. Advantageously, some embodiments of the conjugates are fluorophores, and fluorescence is lost upon photodegradation and drug release. Embodiments of the disclosed targeting agent-drug conjugates are useful for site-specific delivery and selective activation with concomitant drug release. Fluorescence levels of the administered conjugate may be monitored to visualize the location of the conjugate within a subject and/or as an indicator of drug release.

Targeting agent-drug conjugates and intermediate conjugates comprising a drug and a reactive group have a chemical structure according to Formula I, or a pharmaceutically acceptable salt thereof:

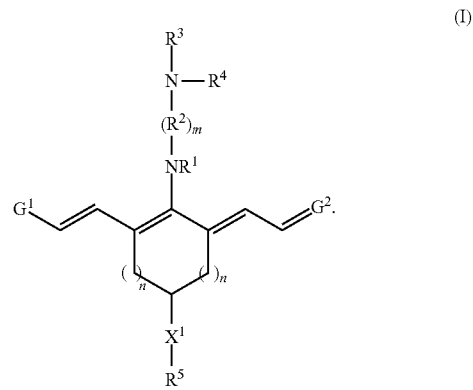

With respect to Formula I, m is 1, 2, 3, 4, or 5; and each n independently is 1, 2, or 3. $R^1$ and $R^4$ independently are alkyl, haloalkyl, cycloalkyl, alkoxy, —ROH, —RC(O)OH, —C(O)—R, or —C(O)—O—R, wherein R is alkyl. $R^2$ is $C(R^c)_2$ wherein each $R^c$ independently is H, halo, alkyl, or aryl, or $(R^2)_m$ collectively is phenyl. $R^3$ is -$L_1$-C(O)—$X^2$-drug, where $L_1$ is a linker moiety or is absent and $X^2$ is O, N(H), or N($CH_3$). $R^5$ is —$(CH_2)_x$-$L_2$-$R^a$, where x is an integer$\geq 1$, $L_2$ is a linker moiety or is absent, and $R^a$ is

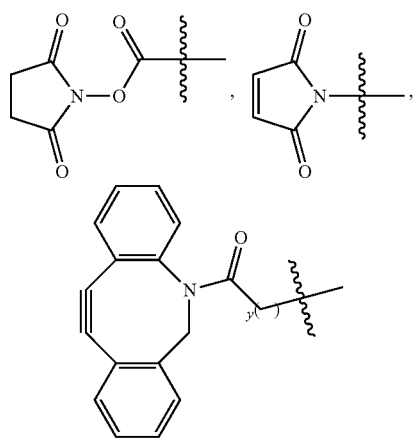

where y is an integer$\geq 1$, —C(O)N(H)$R^b$, —N(H)C(O)$R^b$, —N(H)$R^b$, or —S$R^b$ where $R^b$ is a targeting agent,

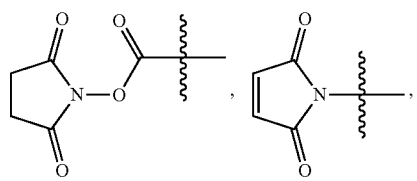

-continued

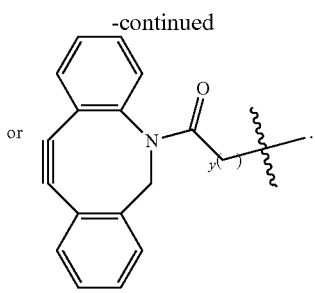

$G^1$ is

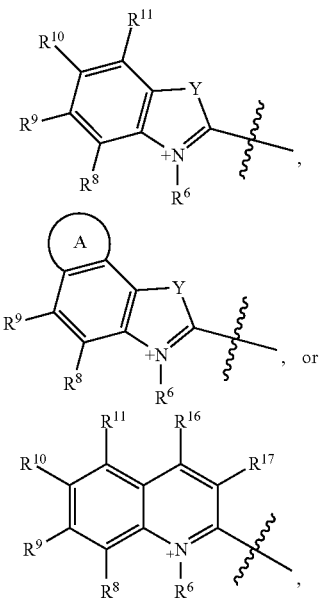

and $G^2$ is

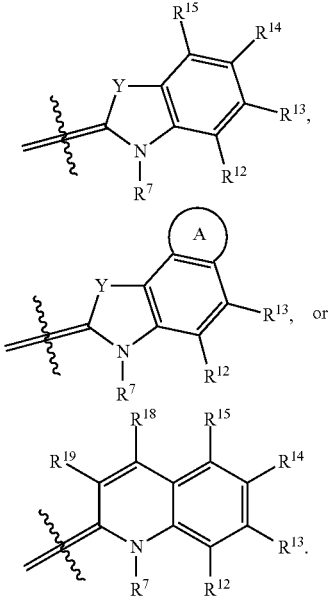

$R^6$ and $R^7$ independently are H, alkyl, alkoxy, alkyl sulfonate, or substituted aminoalkyl. $R^8$-$R^{19}$ independently are H, alkyl, amino, alkoxy, or alkyl sulfonate. Each Y independently is $C(R^d)_2$, S, O, Se, or $N(R^d)$ wherein each $R^d$ independently is H or alkyl. Each ring A independently is a 6-membered fused aliphatic, heteroaliphatic, aryl, or heteroaryl ring.

$G^1$ and $G^2$ may be substantially the same or different from one another. In some embodiments, each Y is the same, $R^6$ and $R^7$ are identical, and $R^8$-$R^{11}$ and $R^{16}$-$R^{17}$ are identical to $R^{12}$-$R^{15}$ and $R^{18}$-$R^{19}$, respectively. In any or all of the above embodiments, Y may be $C(CH_3)_2$. In any or all of the above embodiments, $R^6$ and $R^7$ may be —$(CH_2)_pSO_3^-$ or —$(CH_2)_pN(CH_3)_3^+$, where p is 1, 2, 3, 4, or 5. In any or all of the above embodiments, $R^1$ and $R^4$ independently may be $C_1$-$C_4$ alkyl, —ROH, —RCOOH, or —$RCF_3$, where R is $C_1$-$C_4$ alkyl.

In some embodiments, the conjugate has a structure according to Formula II, wherein $R^1$-$R^9$, $R^{12}$, $R^{13}$, m, $X^1$, and Y are as previously defined:

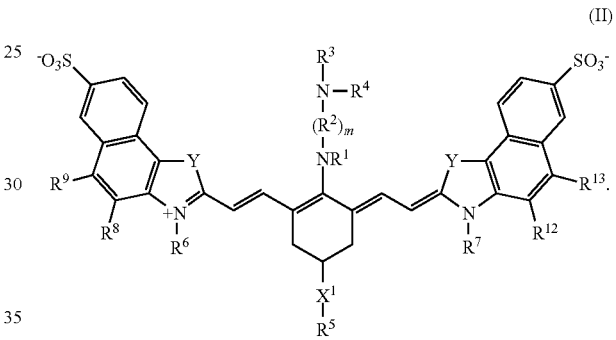

(II)

In any or all of the above embodiments, $R^3$ may be

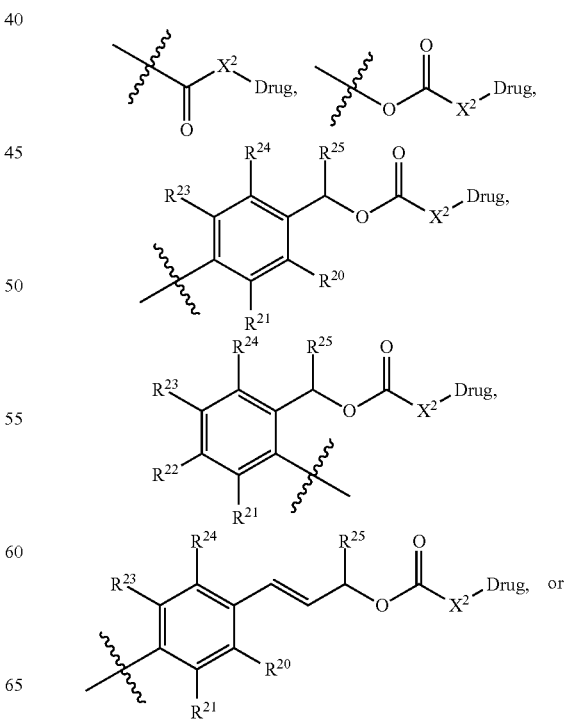

-continued

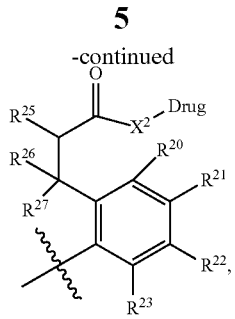

where $R^{20}$-$R^{27}$ independently are H, alkyl, —$NO_2$, —$NR^e{}_2$, —$NR^e{}_3$, alkoxy, or sulfonate, wherein each $R^e$ independently is H, halo, or alkyl. In some embodiments, $R^{20}$-$R^{25}$ are H. In certain embodiments, $R^3$ is

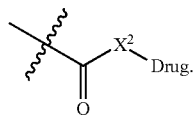

In any or all of the above embodiments, the drug may be an anti-cancer drug. In one embodiment, the drug is a duocarmycin, such as duocarmycin DM.

In any or all of the above embodiments, $R^5$ may be

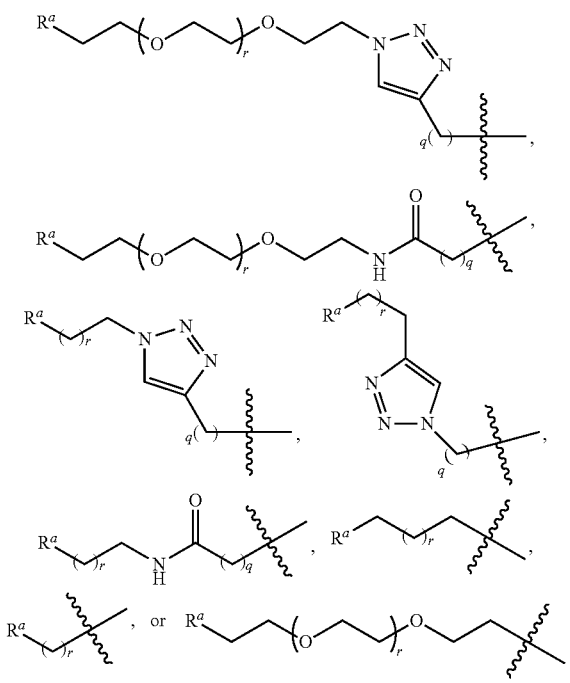

where q and r independently are 1, 2, 3, 4, or 5. In some embodiments, $R^b$ is a targeting agent, such as an antibody.

In any or all of the above embodiments, $R^5$ may be —$(CH_2)_x$-$L_2$-$R^a$, where x is an integer≥1, $L_2$ is a linker moiety or is absent, and $R^a$ is —C(O)N(H)$R^b$, —N(H)C(O)$R^b$, —N(H)$R^b$, or —S$R^b$ where $R^b$ is a targeting agent, and the conjugate further comprises one or more additional moieties bound to $R^b$, each of the additional moieties independently having a chemical structure according to Formula III:

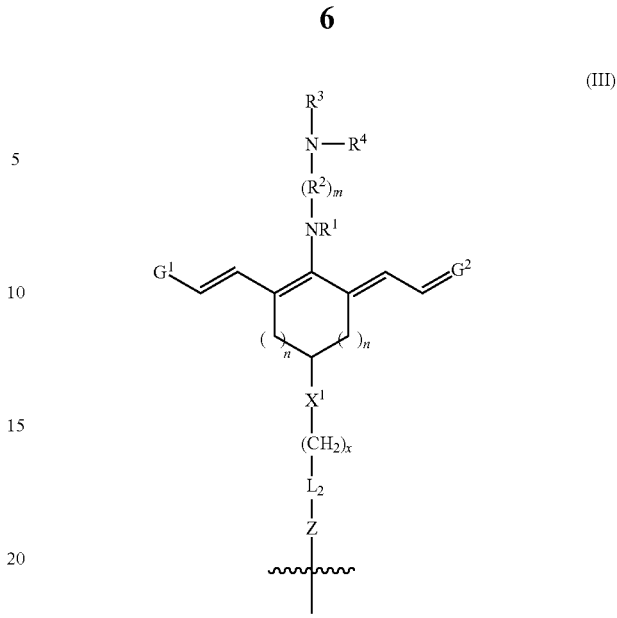

wherein m, n, x, $R^1$-$R^4$, $X^1$, $G^1$, $G^2$, and $L_2$ are as previously defined, and Z is —C(O)N(H)—, —N(H)C(O)—, —N(H)—, or —S—.

A pharmaceutical composition comprises a conjugate according to Formula I wherein $R^b$ is a targeting agent and a pharmaceutically acceptable carrier.

Embodiments of precursor compounds for preparing the disclosed targeting agent-drug conjugates have a chemical structure according to Formula IV, or a salt thereof:

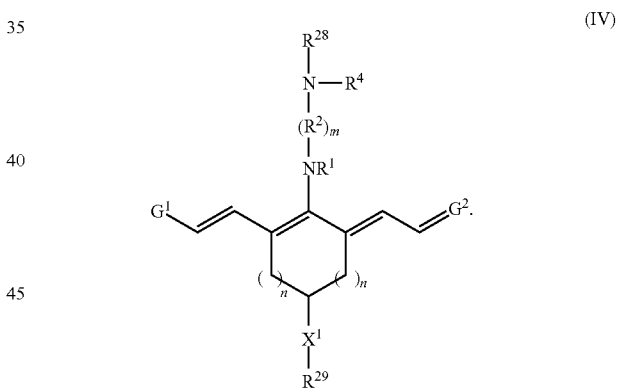

With respect to Formula IV, m, n, $R^1$, $R^2$, $R^4$, $G^1$, $G^2$, and $X^1$ are as previously defined; $R^{28}$ is hydrogen or a protecting group; and $R^{29}$ is —$(CH_2)_u$—C≡CH where u is 1, 2, 3, 4, or 5. In some embodiments, $R^{28}$ is hydrogen.

A method of using a conjugate as disclosed herein includes providing a conjugate according to Formula I, wherein $R^b$ is a targeting agent, and subsequently irradiating the conjugate with targeted application of an effective quantity of light having a selected wavelength in the near-infrared range and a selected intensity to induce a cleavage reaction and release the drug from the conjugate. In some embodiments, irradiating the conjugate with targeted application of light comprises irradiating the conjugate with a laser that produces light having a wavelength of 650-900 nm. In any or all of the above embodiments, the method may further include monitoring a level of fluorescence of the conjugate, and ceasing irradiation when the level of fluorescence falls below a target level.

In any or all of the above embodiments, the method may include (i) providing a biological sample including, or suspected of including, a target molecule; (ii) contacting the biological sample with the conjugate, wherein the targeting agent of the conjugate is capable of recognizing and binding to the target molecule; and (iii) subsequently irradiating the biological sample with the targeted application of light.

In any or all of the above embodiments, the method may further include (i) identifying a subject as having a condition that may be treated with the drug; (ii) administering a therapeutically effective amount of the conjugate or a pharmaceutical composition comprising the conjugate to the subject; and (iii) subsequently irradiating the conjugate by targeted application of an effective quantity of light having a wavelength in the near-infrared range and a selected intensity to a targeted portion of the subject, thereby releasing the drug from at least some molecules of the conjugate. In some embodiments, the subject has a tumor and the targeted portion of the subject includes an area proximate a location of the tumor. In any or all of the above embodiments, the effective quantity of light applied to the targeted portion may be from 5-250 J/cm$^2$.

Another method of using a conjugate as disclosed herein includes (i) administering a therapeutically effective amount of the conjugate or a pharmaceutical composition comprising the conjugate to a subject suspected of having a condition that may be treated with the drug; (ii) subsequently irradiating the conjugate by targeted application of a quantity of light having a wavelength in the near-infrared range and a selected intensity to a targeted portion of the subject, wherein the quantity of light is sufficient to produce fluorescence of the conjugate but insufficient to induce cleavage of the conjugate and release the drug from the conjugate; (iii) detecting any fluorescence from the conjugate in the targeted portion of the subject; and (iv) subsequently irradiating the conjugate, if fluorescence is detected, by targeted application of an effective quantity of light having a wavelength in the near-infrared range and a selected intensity to the targeted portion of the subject, thereby releasing the drug from at least some molecules of the conjugate.

The foregoing and other objects, features, and advantages of the invention will become more apparent from the following detailed description, which proceeds with reference to the accompanying figures.

BRIEF DESCRIPTION OF THE DRAWINGS

FIG. 5 is a synthetic scheme for conjugation of a heptamethine cyanine-duocarmycin DM conjugate, CY(Me)-DuoDM, to panitumumab.

FIG. 6 is a synthetic scheme for conjugation of a heptamethine cyanine-duocarmycin DM conjugate, CY(Et)-DuoDM, to panitumumab.

DETAILED DESCRIPTION

Figure 1:
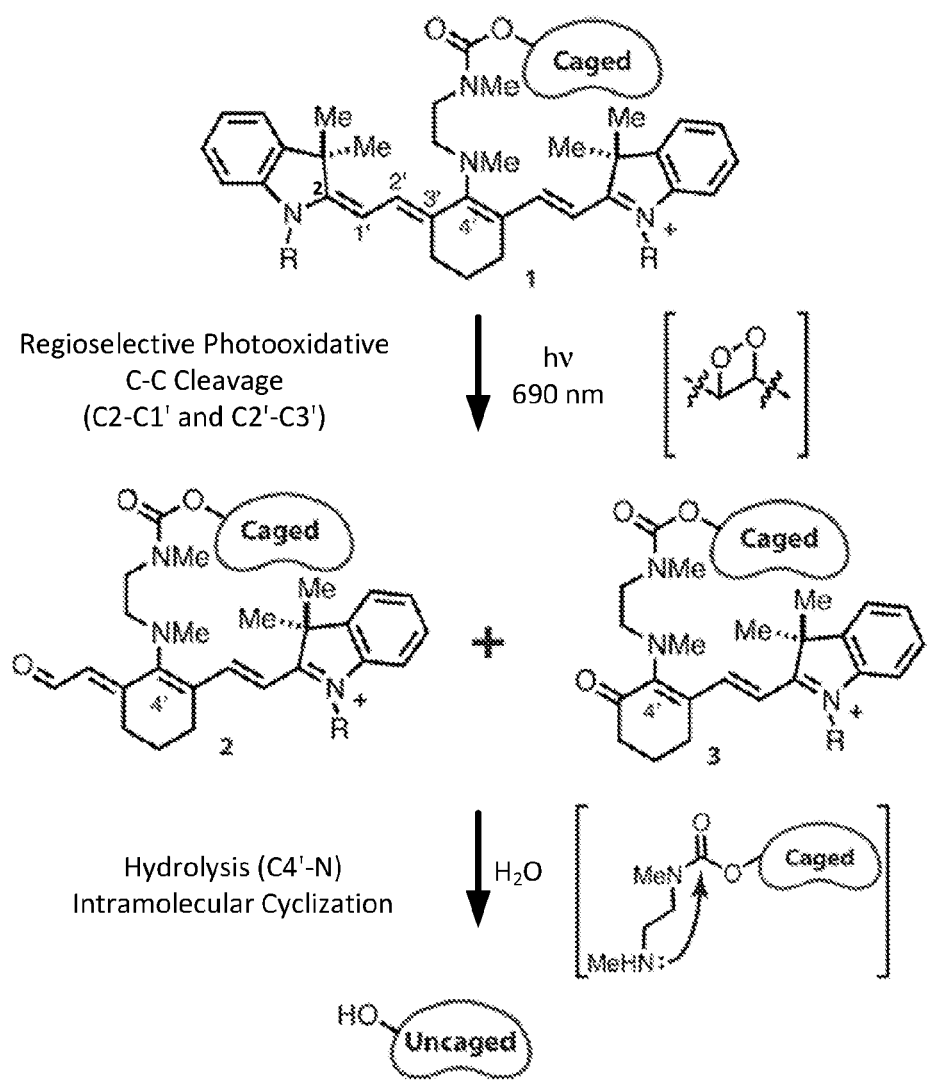
FIG. 1 is a reaction scheme showing photo-induced cleavage of a drug from an exemplary heptamethine cyanine-drug conjugate

This disclosure concerns embodiments of targeting agent-drug conjugates comprising heptamethine cyanine fluorophores, precursors of the conjugates, and methods of making and using the conjugates and precursors. A near-IR uncaging strategy uses the heptamethine cyanine fluorophore scaffold as the caging component. Irradiation with an effective quantity of near-infrared light induces cleavage of the drug from the targeting agent-drug conjugate.

This approach allows target-specific delivery of bioactive small molecules using near-IR optical tools already employed in various clinical settings. An advantageous feature is that the fluorescent properties of the conjugate can be used to evaluate targeting agent-target engagement. Moreover, following administration of therapeutic light doses, the loss of that signal allows real-time assessment of drug release.

Certain embodiments of the disclosed conjugates comprise an antibody and an anti-cancer agent, and are useful for site-specific delivery of the anti-cancer agent to a tumor. By separating the drug payload release process from cellular internalization, the extracellular targeting agent-drug conjugate fraction will release the drug cargo into the local tumor environment. Advantageously, this localized release should effectively transfer molecules from antigen-positive cells to adjacent antigen-negative cells achieving bystander effects, which can be critical for therapeutic efficacy.

I. Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkoxy: A group having the structure —OR, where R is a substituted or unsubstituted alkyl. Methoxy (—OCH$_3$) is an exemplary alkoxy group. In a substituted alkoxy, R is alkyl substituted with a non-interfering substituent.

Alkoxy carbonyl: A group having the structure —(O)C—O—R, where R is a substituted or unsubstituted alkyl.

Alkyl: A hydrocarbon group having a saturated carbon chain. The chain may be branched, unbranched, or cyclic (cycloalkyl). The term lower alkyl means the chain includes 1-10 carbon atoms. Unless otherwise specified, the term alkyl encompasses substituted and unsubstituted alkyl.

Alkyl carbonyl: A group having the structure —(O)C—R, where R is a substituted or unsubstituted alkyl.

Alkyl sulfonate: A group having the structure —R—SO$_3^-$, where R is a substituted or unsubstituted alkyl.

Amino: A group having the structure —N(R)R' where R and R' are independently hydrogen, haloalkyl, aliphatic, heteroaliphatic, aryl (such as optionally substituted phenyl or benzyl), heteroaryl, alkylsulfano, or other functionality. A "primary amino" group is —NH$_2$. "Mono-substituted amino" means a radical —N(H)R substituted as above and includes, e.g., methylamino, (1-methylethyl)amino, phenylamino, and the like. "Di-substituted amino" means a radical —N(R)R' substituted as above and includes, e.g., dimethylamino, methylethylamino, di(1-methylethyl)amino, and the like. The term amino also encompasses charged tri-substituted amino groups, e.g., —N(R)(R')R''$^+$ where R, R', and R'' are independently hydrogen, haloalkyl, aliphatic, heteroaliphatic, aryl (such as optionally substituted phenyl or benzyl), heteroaryl, alkylsulfano, or other functionality.

Aminoalkyl: A chemical functional group —RNH$_2$ or —RNH$_3^+$ where R is an alkyl group. "Substituted aminoalkyl" means that the amino group is substituted, e.g., —RN(R')R'' or —RN(R')(R'')R'''$^+$ where R', R'', and R''' are independently hydrogen, haloalkyl, aliphatic, heteroaliphatic, aryl (such as optionally substituted phenyl or benzyl), heteroaryl, alkylsulfano, or other functionality.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In avian and reptilian species, IgY antibodies are equivalent to mammalian IgG.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

The structure of IgY antibodies is similar to the structure of mammalian IgG, with two heavy ("nu" chains; approximately 67-70 kDa) and two light chains (22-30 kDa). The molecular weight of an IgY molecule is about 180 kDa, but it often runs as a smear on gels due to the presence of about 3% carbohydrate. Heavy chains (H) of IgY antibodies are composed of four constant domains and one variable domain, which contains the antigen-binding site.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999). As used herein, the term "antibodies" includes antibodies comprising one or more unnatural (i.e., non-naturally occurring) amino acids (e.g., p-acetyl-phenyl-alanine) to facilitate site-specific conjugation.

Antibodies for use in the methods of this disclosure can be monoclonal or polyclonal, and for example specifically bind a target such as the target antigen. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, Using Antibodies: A Laboratory Manual, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. As used herein, a "target antigen" is an antigen (including an epitope of the antigen) that is recognized and bound by a targeting agent. "Specific binding" does not require exclusive binding. In some embodiments, the antigen is obtained from a cell or tissue extract. In some embodiments, the target antigen is an antigen on a tumor cell. An antigen need not be a full-length protein. Antigens contemplated for use include any immunogenic fragments of a protein, such as any antigens having at least one epitope that can be specifically bound by an antibody.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, the term aryl encompasses substituted and unsubstituted aryl.

Biological sample: As used herein, a "biological sample" refers to a sample obtained from a subject (such as a human or veterinary subject) or other type of organism, such as a plant, bacteria or insect. Biological samples from a subject include, but are not limited to, cells, tissue, serum, blood, plasma, urine, saliva, cerebral spinal fluid (CSF) or other bodily fluid. In particular examples of the method disclosed herein, the biological sample is a tissue sample.

Conjugate: Two or more moieties directly or indirectly coupled together. For example, a first moiety may be covalently coupled to a second moiety. Indirect attachment is possible, such as by using a "linker" (a molecule or group of atoms positioned between two moieties).

DMP: Dess-Martin periodinane

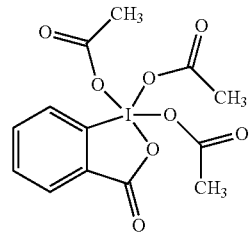

DMP

Drug: As used herein, the term "drug" refers to a substance which has a physiological effect when administered to a subject, and is intended for use in the treatment, mitigation, cure, prevention, or diagnosis of disease or used to otherwise enhance physical or mental well-being. The term "small molecule drug" refers to a drug having a molecular weight<1,000 Daltons.

An anti-cancer drug is a drug that is used to treat malignancies. Exemplary anti-cancer drugs include, but are not limited to, abiraterone, actinomycin D, altretamine, amifostine, anastrozole, asparaginase, bexarotene, bicalutamide, bleomycin, buserelin, busulfan, carboplatin, carmustine, chlorambucil cisplatin, cladribine, clodronate, combretastatin A4, cyclophosphamide, cyproterone, cytarabine, dacarbazine, daunorubicin, degarelix, diethylstilbestrol, docetaxel, doxorubicin, duocarmycin DM, epirubicin, ethinyl estradiol, etoposide, exemestane, 5-fluorouracil, fludarabine, flutamide, folinic acid, fulvestrant, gemcitabine, goserelin, ibandronic acid, idarubicin, ifosfamide, irinotecan, lanreotide, lenalidomide, letrozole, leuprorelin, medroxyprogesterone, megestrol, melphalan, mesna, methotrexate, octreotide, pamidronate, pemetrexed, mitocmycin, mitotane, mitoxantrone, oxaliplatin, paclitaxel, pentastatin, pipbroman, plicamycin, procarbazine, raltitrexed, stilbestrol, streptozocin, tamoxifen, temozolomide, teniposide, topotecan, triptorelin, vinblastine, vincristine, vinorelbine, and zolendronic acid.

Effective amount or therapeutically effective amount: An amount sufficient to provide a beneficial, or therapeutic, effect to a subject or a given percentage of subjects.

Epitope: An antigenic determinant Epitopes are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Halogen: The terms halogen and halo refer to fluorine, chlorine, bromine, iodine, and radicals thereof.

Heteroaliphatic: An aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heterocycloaliphatic", or "heterocyclic" groups.

Heteroalkyl: An alkyl group as defined above containing at least one heteroatom, such as N, O, S, or $S(O)_n$ (where n is 1 or 2). Unless otherwise specified, the term heteroalkyl encompasses substituted and unsubstituted heteroalkyl.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur. Unless otherwise specified, the term heteroaryl encompasses substituted and unsubstituted heteroaryl.

Ligand: A molecule that binds to a receptor, having a biological effect.

Linker: A molecule or group of atoms positioned between two moieties. As used herein, the term "linker" refers to a group of atoms positioned between the cyanine fluorophore and a targeting agent or reactive group, or to a group of atoms positioned between the cyanine fluorophore and a drug.

Near-infrared (near-IR, NIR): Wavelengths within the range of 650-2500 nm. Unless otherwise specified, the terms "near-infrared" and "NIR" as used herein refer to wavelengths within the range of 650-900 nm.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more targeting agent-drug conjugates as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of a disclosed conjugate, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Protecting group: When synthesizing organic compounds, often a specific functional group cannot survive the required reagents or chemical environments. These groups must be protected. A protecting group, or protective group, is introduced into a molecule by chemical modification of a functional group in order to obtain chemoselectivity in a subsequent chemical reaction. Various exemplary protecting or protective groups are disclosed in Greene's Protective Groups in Organic Synthesis, by Peter G. M. Wuts and Theodora W. Greene (Oct. 30, 2006), which is incorporated herein by reference.

Specific binding partner: A member of a pair of molecules that interact by means of specific, non-covalent interactions that depend on the three-dimensional structures of the molecules involved. Exemplary pairs of specific binding partners include antigen/antibody, hapten/antibody, receptor/ligand, nucleic acid strand/complementary nucleic acid strand, substrate/enzyme, inhibitor/enzyme, carbohydrate/lectin, biotin/avidin (such as biotin/streptavidin), and virus/cellular receptor.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, isocyano, isothiocyano, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Sulfonate-containing group: A group including $SO_3^-$. The term sulfonate-containing group includes —$SO_3^-$ and —$RSO_3^-$ groups, where R is substituted or unsubstituted alkyl, substituted or unsubstituted heteroalkyl, substituted or unsubstituted aryl, or substituted or unsubstituted heteroaryl.

Target: An intended molecule to which a disclosed targeting agent-drug conjugate is capable of specifically binding. Examples of targets include proteins and nucleic acid sequences present in tissue samples. A target area is an area in which a target molecule is located or potentially located.

Targeting agent: An agent that promotes preferential or targeted delivery to a target site, for example, a targeted location in a subject's body, such as a specific organ, organelle, physiologic system, tissue, or site of pathology such as a tumor, area of infection, or area of tissue injury. Targeting agents function by a variety of mechanisms, such as selective concentration in a target site or by binding to a specific binding partner. Suitable targeting agents include, but are not limited to, proteins, polypeptides, peptides, glycoproteins and other glycoslyated molecules, oligonucleotides, phospholipids, lipoproteins, alkaloids, and steroids. Exemplary targeting agents include antibodies, antibody fragments, affibodies, aptamers, albumin, cytokines, lymphokines, growth factors, hormones, enzymes, immune modulators, receptor proteins, antisense oligonucleotides, avidin, nano particles, and the like. Particularly useful of targeting agents are antibodies, nucleic acid sequences, and receptor ligands, although any pair of specific binding partners can be readily employed for this purpose.

Treat/treatment: As used herein, the terms "treat" and "treatment" mean to inhibit or reduce at least one sign or symptom associated with a condition, i.e., a disorder or disease. With respect to a tumor, treating may mean inhibiting tumor growth and/or reducing a tumor volume. Treatment may, for example, produce a reduction in severity of some or all clinical symptoms of the tumor, a slower progression of the tumor (for example by prolonging the life of a subject having the tumor), a reduction in the number of tumor reoccurrence, an improvement in the overall health or well-being of the subject, or by other parameters well known in the art that are specific to the particular disorder or disease.

II. Conjugates

Disclosed herein are embodiments of conjugates comprising a heptamethine cyanine fluorophore, a drug, and a targeting agent or a reactive group suitable for further conjugation. FIG. 1 shows an exemplary prior art heptamethine cyanine-drug conjugate where R is H, alkyl, alkoxy, alkyl sulfonate, or substituted aminoalkyl, and the "caged" moiety comprises a drug. As shown FIG. 1, the conjugates undergo photodegradation when irradiated with near-IR light, which renders the C4'—N bond hydrolytically labile. This leads to uncaging of the C4'-nitrogen, which spontaneously cyclizes onto a pendant carbamate group, ejecting the drug payload. The photodegradation involves a singlet oxygen-mediated regioselective cyanine polyene cleavage process that proceeds through dioxetane intermediates. Although the exemplary conjugates of FIG. 1 do not include a targeting agent, the photodegradation mechanism is the same for the conjugates disclosed herein.

Conjugates comprising a heptamethine cyanine fluorophore, a drug, and a targeting agent or a reactive group suitable for further conjugation have a chemical structure according to Formula I, or a pharmaceutically acceptable salt thereof.

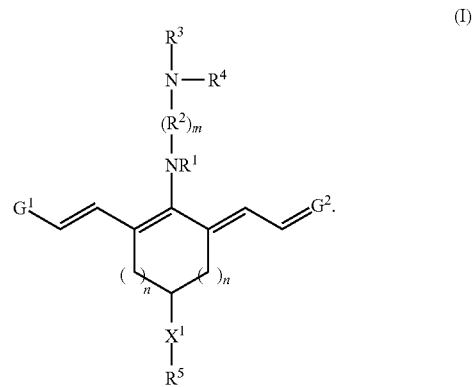

With respect to Formula I, m is 1, 2, 3, 4, or 5; and each n independently is 1, 2, or 3. $R^1$ and $R^4$ independently are alkyl, haloalkyl, cycloalkyl, alkoxy, —ROH, —RC(O)OH, —C(O)—R, or —C(O)—O—R, wherein R is alkyl. $R^2$ is $C(R^c)_2$ wherein each $R^c$ independently is H, halo, alkyl, or aryl, or $(R^2)_m$ collectively is phenyl. $R^3$ is -$L_1$-C(O)—$X^2$-drug, where $L_1$ is a linker moiety or is absent and $X^2$ is O, N(H), or N(CH$_3$). $R^5$ is —(CH$_2$)$_x$-$L_2$-$R^a$, where x is an integer≥1, $L_2$ is a linker moiety or is absent, and $R^a$ is

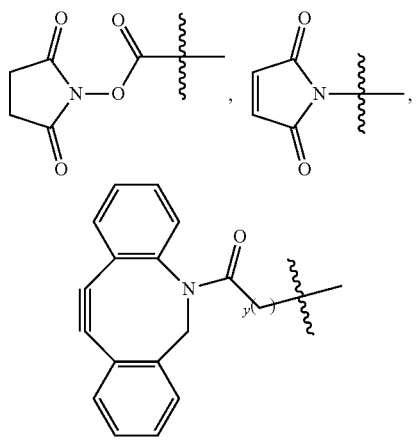

where y is an integer≥1, —C(O)N(H)$R^b$, —N(H)C(O)$R^b$, —N(H)$R^b$, or —S$R^b$ where $R^b$ is a targeting agent,

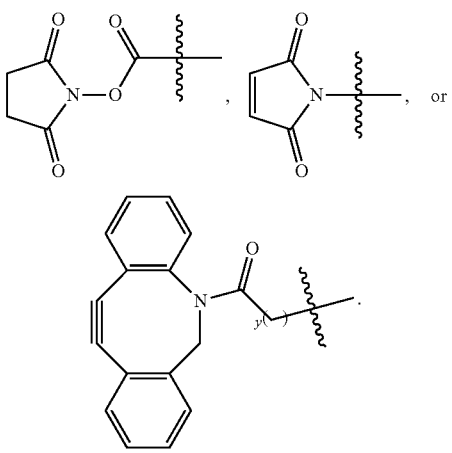

$G^1$ is

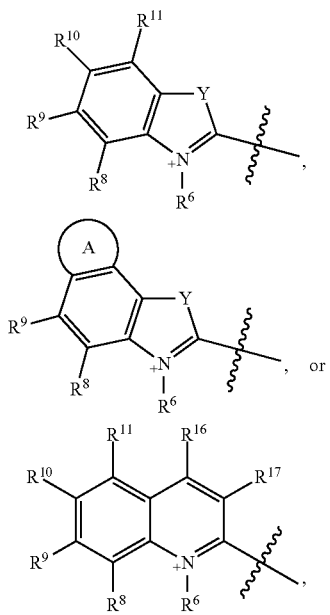

and $G^2$ is

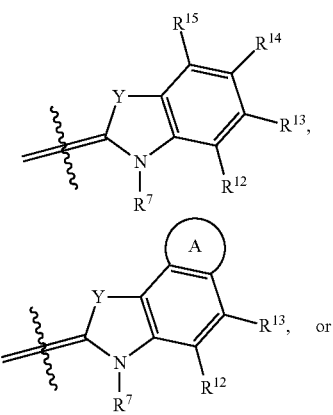

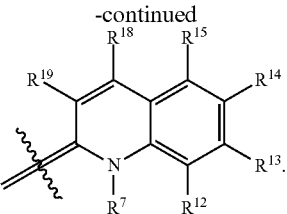

$R^6$ and $R^7$ independently are H, alkyl, alkoxy, alkyl sulfonate, or substituted aminoalkyl. $R^8$-$R^9$ independently are H, alkyl, amino, alkoxy, or alkyl sulfonate. Each Y independently is $C(R^d)_2$, S, O, Se, or $N(R^d)$ wherein each $R^d$ independently is H or alkyl. Each ring A independently is a 6-membered fused aliphatic, heteroaliphatic, aryl, or heteroaryl ring.

In some embodiments, $R^1$ and $R^4$ independently are lower alkyl, —ROH, —RCOOH, or —RCF$_3$, where R is lower alkyl. In certain embodiments, $R^1$ and $R^4$ independently are $C_1$-$C_4$ alkyl or —ROH wherein R is $C_1$-$C_4$ alkyl. For example, $R^1$ and $R^4$ independently may be methyl, ethyl, n-propyl, i-propyl, t-butyl, or —(CH$_2$)$_2$OH. In certain embodiments, $R^1$ and $R^4$ are the same. In one embodiment, $R^1$ and $R^4$ are ethyl. In another embodiment, $R^1$ and $R^4$ are methyl. The identities of IV and $R^4$ influence the wavelength suitable to induce cyclization with subsequent release of the drug. For instance, replacing methyl groups at $R^1$ and $R^4$ with ethyl groups was shown in one example to red-shift the effective wavelength by 50 nm, i.e., from 690 nm to 740 nm. Thus, IV and $R^4$ may be used to "tune" the wavelength effective to induce drug release from the conjugate. A person of ordinary skill in the art will understand that a longer wavelength may penetrate deeper into the tissues of a subject.

In some embodiments, $R^2$ is —CH$_2$— and m is 1, 2 or 3. In certain examples, m is 2, and $(R^2)_m$ is —CH$_2$CH$_2$—. In some embodiments, each n is 1.

$R^6$ and $R^7$ independently are H, alkyl, alkoxy, alkyl sulfonate, or substituted aminoalkyl. In some embodiments, $R^6$ and $R^7$ independently are alkyl sulfonate or substituted aminoalkyl, such as —(CH$_2$)$_p$SO$_3^-$ or —(CH$_2$)$_p$N(CH$_3$)$_3^+$, where p is 1, 2, 3, 4, or 5 In one embodiment, $R^6$ and $R^7$ are —(CH$_2$)$_4$SO$_3^-$. In another embodiment, $R^6$ and $R^7$ are —(CH$_2$)$_4$N(CH$_3$)$_3^+$. In certain embodiments, $R^8$-$R^{19}$ are hydrogen. Each Y independently is $C(R^d)_2$, S, O, Se, or $N(R^d)$ wherein each $R^d$ independently is H or alkyl. In some examples, each Y independently is $C(CH_3)_2$ or S. When $R^6$ is a targeting agent and Y is $C(R^d)_2$, at least one $R^d$ may be alkyl. In certain embodiments, each Y is $C(CH_3)_2$.

Each ring A independently is a 6-membered fused aliphatic, heteroaliphatic, aryl, or heteroaryl ring. Ring A may be substituted or unsubstituted. In some embodiments, ring A is a fused phenyl ring substituted with optionally substituted sulfonate. For example, ring A may be a fused phenyl ring substituted with —SO$_3^-$. In certain examples, inclusion of a sulfonated ring A, such as a sulfonated phenyl, improves biodistribution when the conjugate is administered in vivo and/or red-shifts the wavelength effective to induce cleavage and release the drug from the conjugate.

The two heterocycle moieties, $G^1$ and $G^2$, may be substantially similar or different from one another. In some embodiments, $G^1$ is

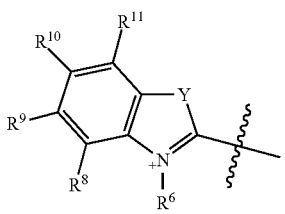

and G² is

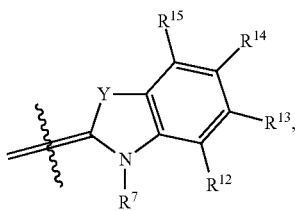

or G¹ is

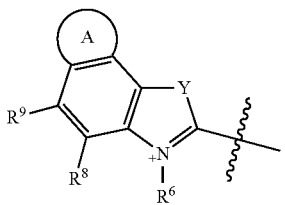

and G² is

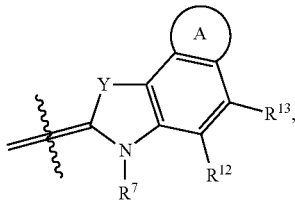

or G¹ is

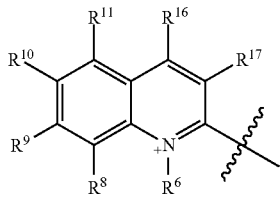

and G² is

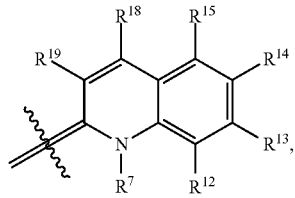

wherein each Y is the same, $R^6$ and $R^7$ are identical, and $R^8$-$R^{11}$ and $R^6$-$R^7$ are identical to $R^{12}$-$R^{15}$ and $R^{18}$-$R^{19}$, respectively.

In some embodiments, the conjugate has a structure according to Formula II, wherein $R^1$-$R^9$, $R^{12}$, $R^{13}$, m, $X^1$, and Y are as previously defined:

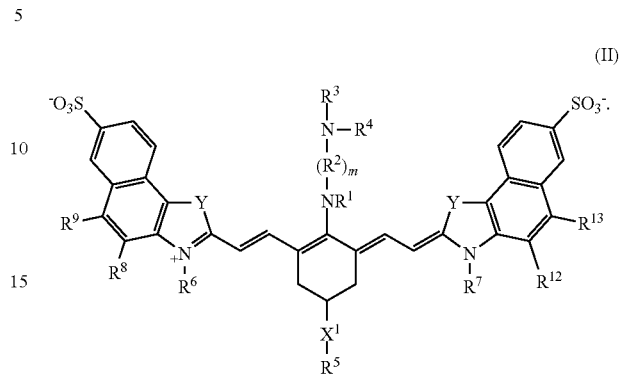

(II)

In certain embodiments, the conjugate has a structure according to Formula II, wherein $R^6$ and $R^7$ are identical, $R^8$ and $R^{12}$ are identical, and $R^9$ and $R^{13}$ are identical.

$R^3$ is -$L_1$-C(O)—$X^2$-drug, where $L_1$ is a linker moiety or is absent and $X^2$ is O, N(H), or N(CH₃). In one embodiment, $L_1$ is absent. In an independent embodiment, $L_1$ is aryl or heteroaryl substituted with at least one substituent comprising a substituted or unsubstituted aliphatic or heteroaliphatic moiety, wherein the aryl or heteroaryl ring is the site of attachment to the nitrogen atom and the substituent is bonded to the —C(O)—$X^2$-drug moiety. In some embodiments, $R^3$ is:

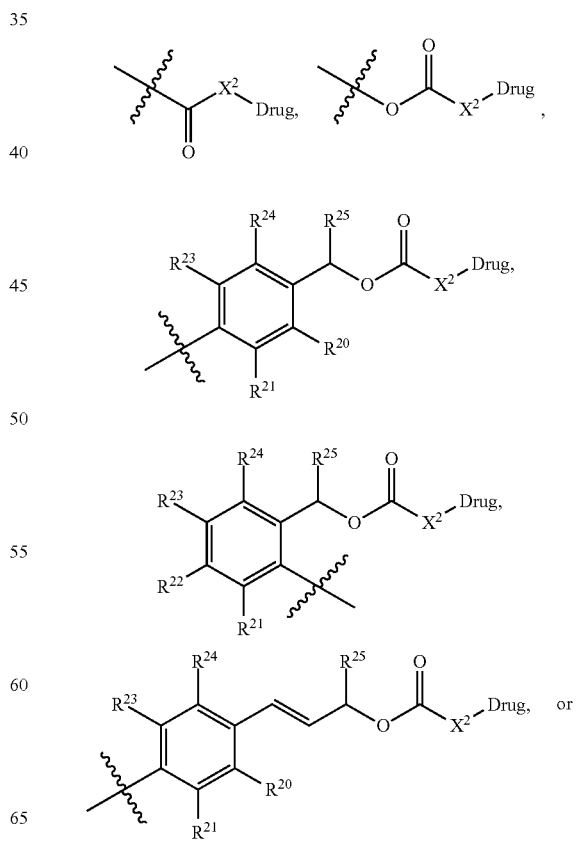

-continued

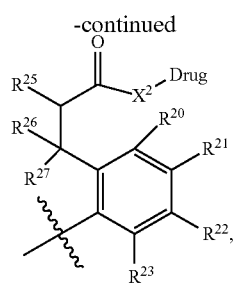

where $X^2$ is O, N(H), or N(CH$_3$), and $R^{20}$-$R^{27}$ independently are H, alkyl, —NO$_2$, —NR$^e_2$, —NR$^e_3$, alkoxy, or sulfonate, wherein each R$^e$ independently is H, halo, or alkyl. In certain embodiments, $R^{20}$-$R^{25}$ are H. In some examples, $R^3$ is —C(O)—X$^2$-Drug.

The drug can be any drug capable of conjugation to the remainder of the R$^3$ moiety. In some embodiments, the drug is a small-molecule drug, e.g., a drug having a molecular weight<1,000 Daltons. In certain embodiments, the drug moiety is an anti-cancer drug. In one embodiment, the drug is an anti-breast cancer drug. In some embodiments, the drug is a duocarmycin, such as duocarmycin DM or duocarmycin SA. The duocarmycins are cytotoxic antibiotics that are DNA minor groove-binding alkylating agents, and are suitable for use against solid tumors. Another exemplary drug is hemiasterlin, a natural product that disrupts microtubule dynamics and, in some doses, depolymerizes microtubules.

Exemplary —X$^2$-Drug moieties include, but are not limited to:

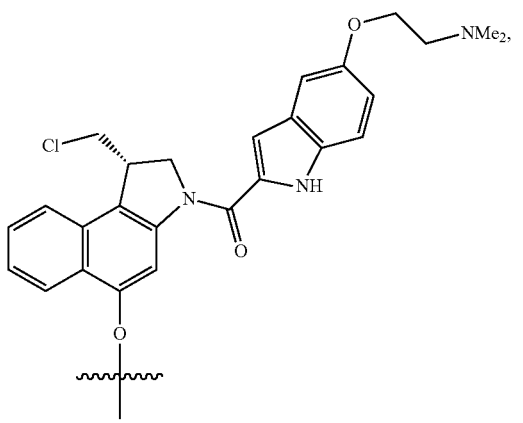

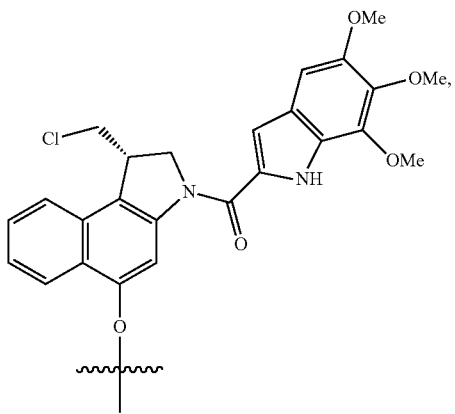

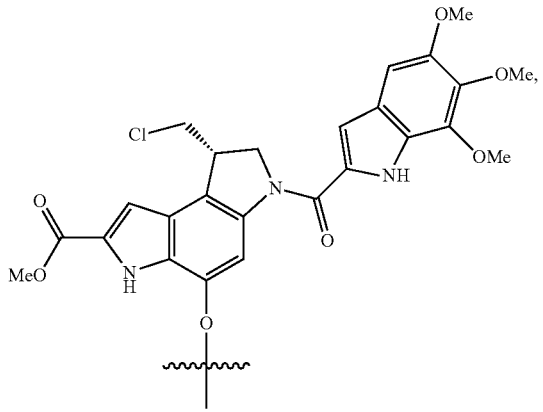

-continued
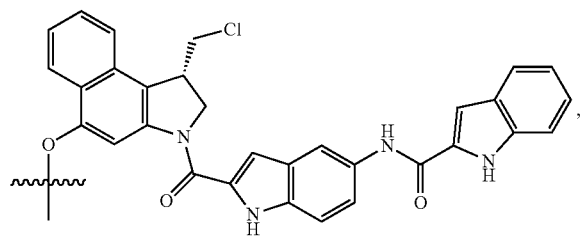
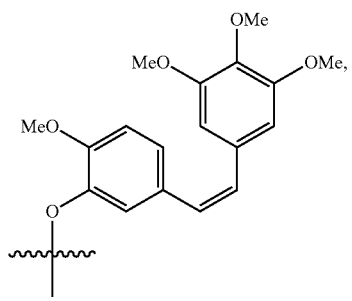
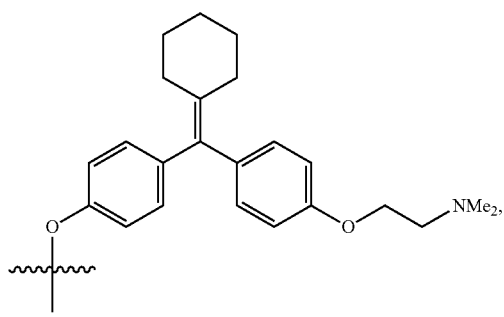
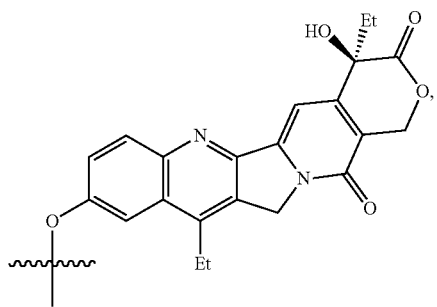
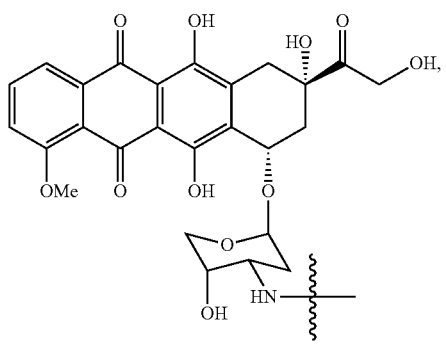

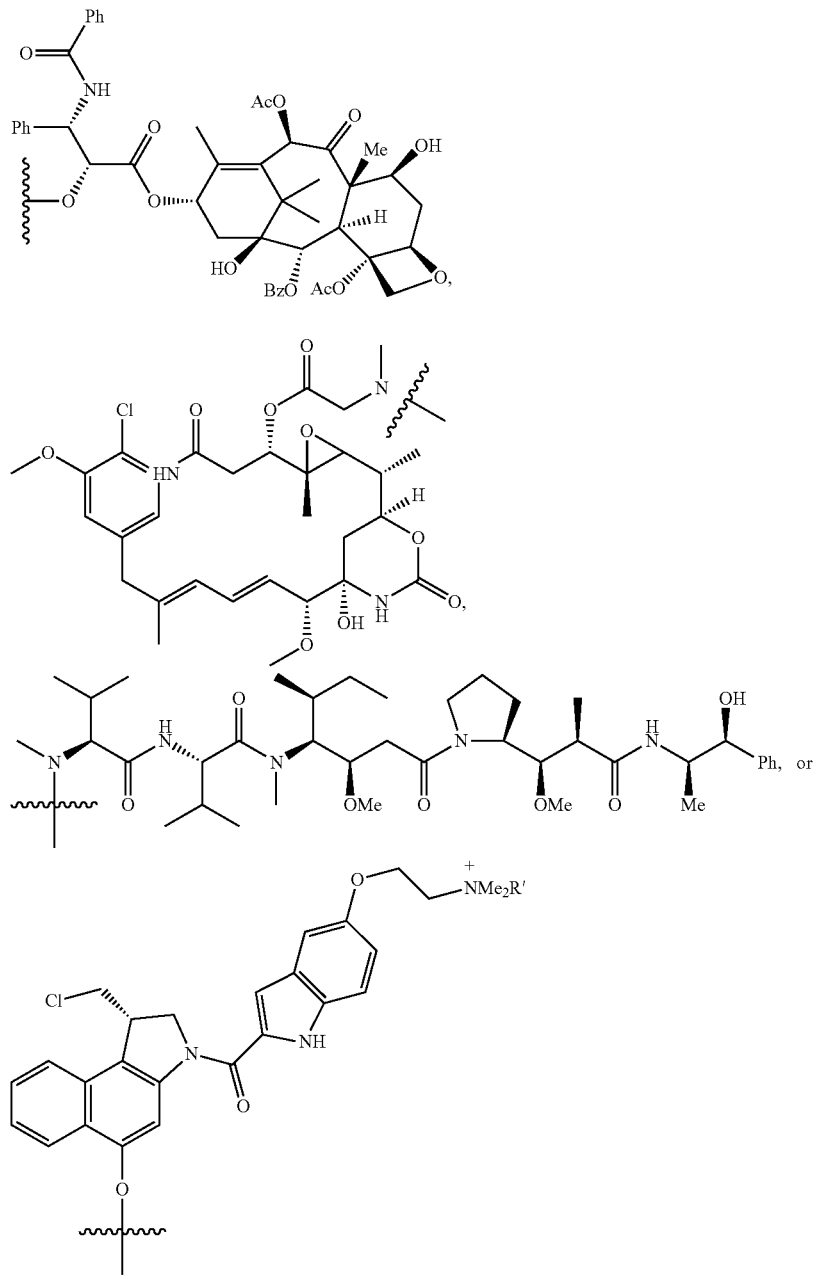
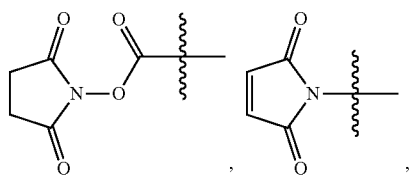
where R' is lower alkyl or alkyl sulfonate, such as methyl or —(CH$_2$)$_4$SO$_3$$^-$. R$^{11}$ is —(CH$_2$)$_x$-L$_2$-R$^a$, where x is an integer ≥1, L$_2$ is a linker moiety or is absent, and R$^a$ is
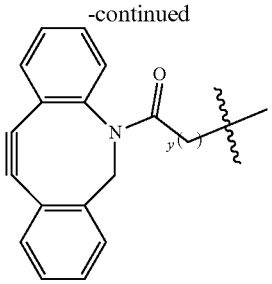
where y is an integer ≥1, —C(O)N(H)R$^b$, —N(H)C(O)R$^b$, —N(H)R$^b$, or —SR$^b$ where R$^b$ is a targeting agent,

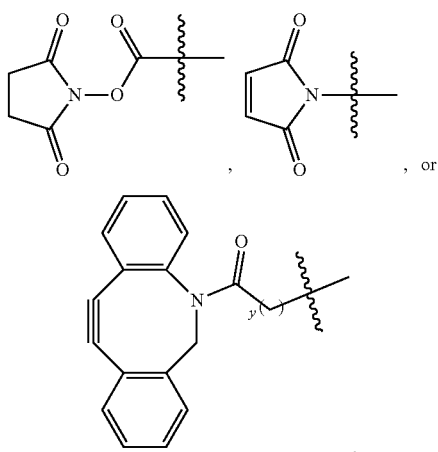

, or

In some embodiments, $L_2$ is aliphatic, heteroaliphatic, or heteroaryl-aliphatic. In one embodiment, $R^a$ is —C(O)N(H)$R^b$ or —N(H)C(O)$R^b$. In an independent embodiment, $R^b$ is a targeting agent. Exemplary targeting agents include, but are not limited to, antibodies, ligands, nucleic acid strands, and the like. In certain examples, the targeting agent is an antibody. In one embodiment, $R^a$ is —C(O)N(H)$R^b$ or —N(H)C(O)$R^b$ and $R^b$ is an antibody. In an independent embodiment, $R^b$ is a ligand, e.g., a ligand capable of binding to a receptor on a cell surface.

Exemplary antibodies include antibodies capable of recognizing and binding to a target molecule, such as a biomarker associated with a disease, infection, or environmental exposure. Biomarkers include, but are not limited to, proteins, peptides, lipids, metabolites, and nucleic acids. In some embodiments, the antibody is capable of recognizing and binding to a tumor biomarker, such as a protein only found in or on tumor cells or to a cell-surface receptor associated with one or more cancers. For example, panitumumab is a human monoclonal antibody that recognizes and binds to human epidermal growth factor receptor 1 (HER1); HER1 is overexpressed in numerous tumor types and is also associated with some inflammatory diseases. Trastuzumab and pertuzumab are monoclonal antibodies that bind to the HER2/neu receptor, which is over-expressed in some breast cancers. Brentuximab is a monoclonal antibody that targets a cell-membrane protein CD30, which is expressed in classical Hodgkin lymphoma and systemic anaplastic large cell lymphoma.

Exemplary $R^5$ groups include:

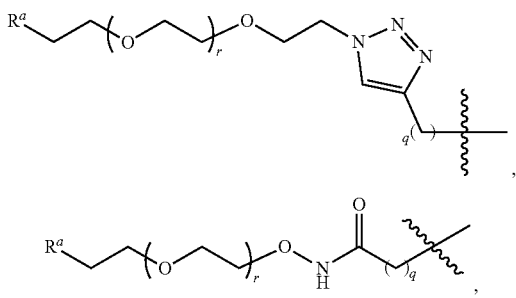

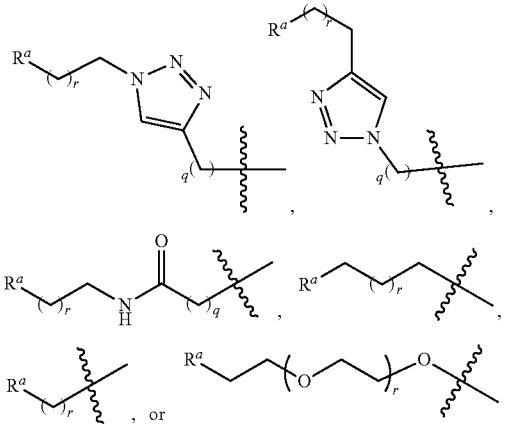

where q and r independently are 1, 2, 3, 4, or 5. In certain examples, $R^5$ is

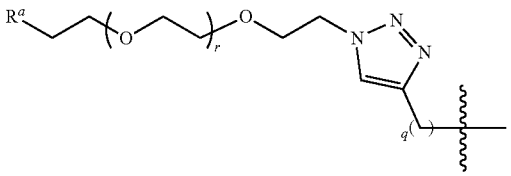

where q and r independently are 1, 2, 3, 4, or 5.

In some embodiments, $R^a$ or $R^b$ is

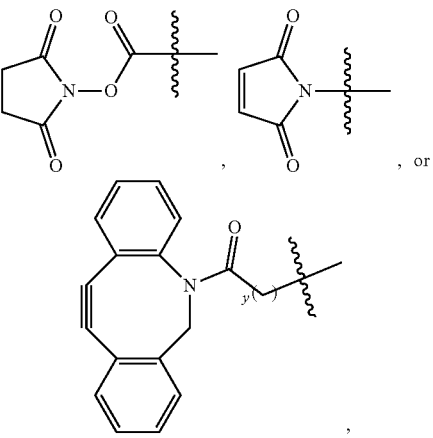

and the conjugate according to Formula I or Formula II is an intermediate conjugate that may be used for further conjugation reactions, such as conjugation to a targeting agent.

Advantageously, the position of $R^5$ facilitates conjugation of multiple heptamethine cyanine-drug moieties to a single targeting agent, such as an antibody. In such embodiments, $R^5$ is —(CH$_2$)$_x$-L$_2$-R$^a$, where x is an integer≥1, $L_2$ is a linker moiety or is absent, $R^a$ is —C(O)N(H)$R^b$, —N(H)C(O)$R^b$, —N(H)$R^b$, or —S$R^b$ where $R^b$ is a targeting agent, and the conjugate further comprises one or more additional moieties bound to $R^b$, each of the additional moieties independently having a chemical structure according to Formula III:

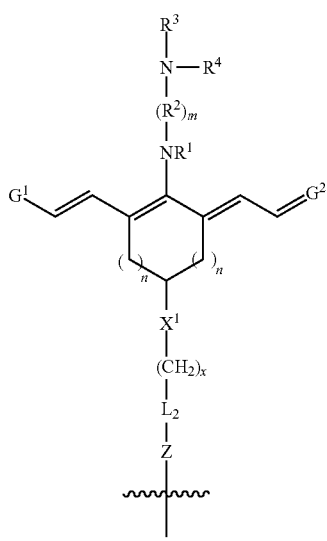

(III)

wherein m, n, x, $R^1$-$R^4$, $X^1$, $G^1$, $G^2$, and $L_2$ are as previously defined, and Z is —C(O)N(H)—, —N(H)C(O)—, —N(H)—, or —S—. In some embodiments, from 1-5 additional moieties, such as from 1-3 additional moieties, are bound to the targeting agent. Thus, from 1-6 heptamethine cyanine-drug moieties may be bound to a single targeting agent. In certain embodiments, from 1-4 heptamethine cyanine-drug moieties are bound to a single targeting agent. Increasing the number of heptamethine cyanine-drug moieties bound to a single targeting agent may increase fluorescence from the conjugate in vivo, and/or increase the concentration of drug released when the conjugate is irradiated with an effective quantity of near-infrared light. In one embodiment, each moiety includes the same drug. In an independent embodiment, the drug may differ such that two or more drugs may be bound to the targeting agent via the heptamethine cyanine-drug moieties.

Exemplary conjugates and intermediate conjugates are shown in Table 1, wherein where $R^1$ and $R^4$ are methyl, ethyl, n-propyl, i-propyl, t-butyl, or —(CH$_2$)$_2$OH; $R^6$ and $R^7$ are —(CH$_2$)$_p$SO$_3^-$ or —(CH$_2$)$_p$N(CH$_3$)$_3^+$, where p is 1, 2, 3, 4, or 5; and Q is —N(H)R$^b$ or

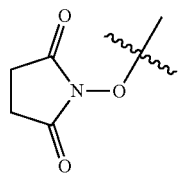

$R^b$ is a targeting agent, particularly an antibody such as panitumumab or trastuzumab.

TABLE 1

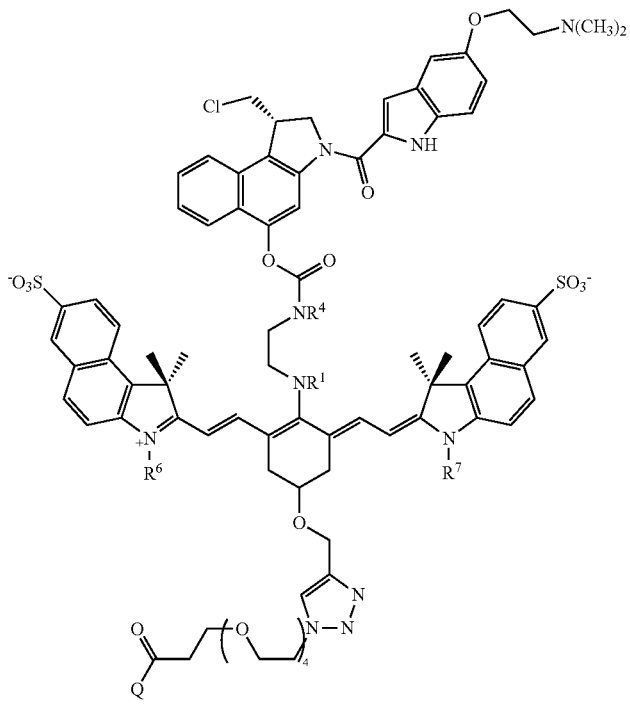

TABLE 1-continued
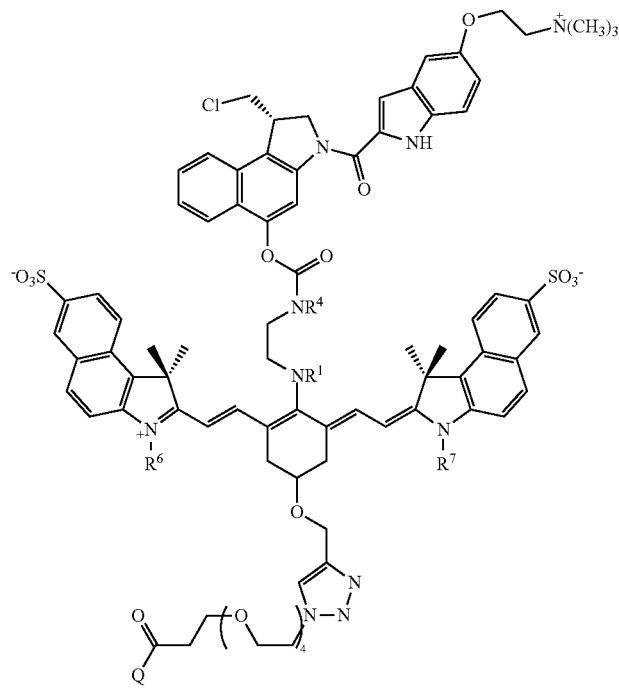
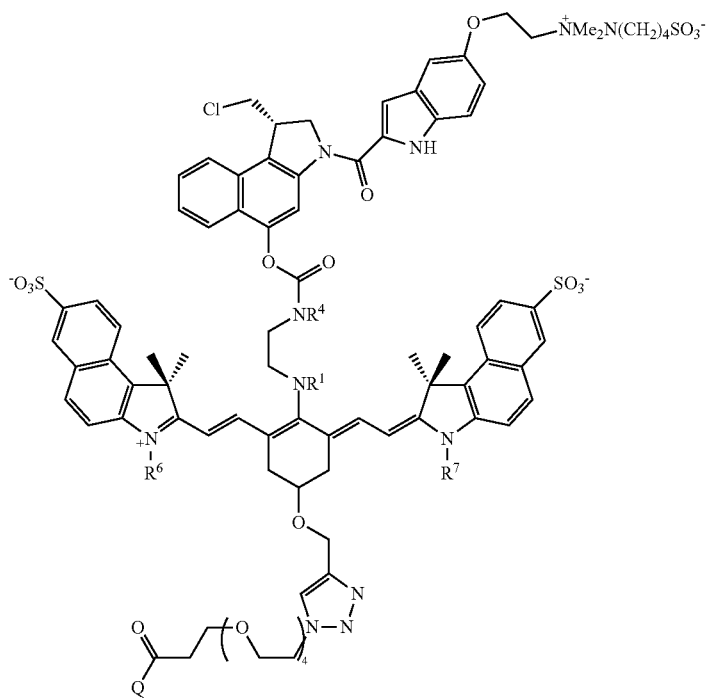

TABLE 1-continued
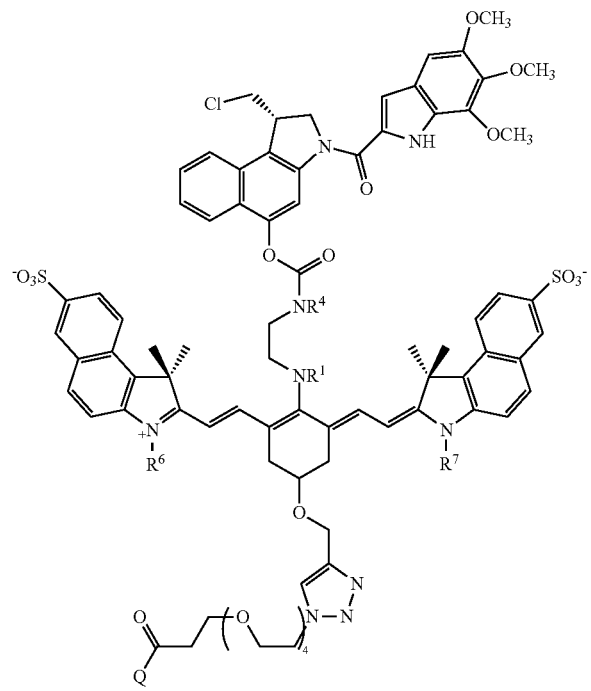
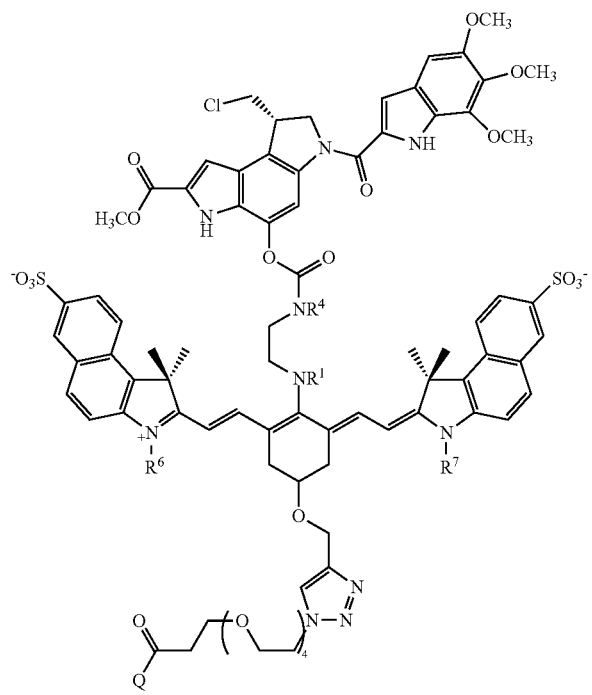

TABLE 1-continued
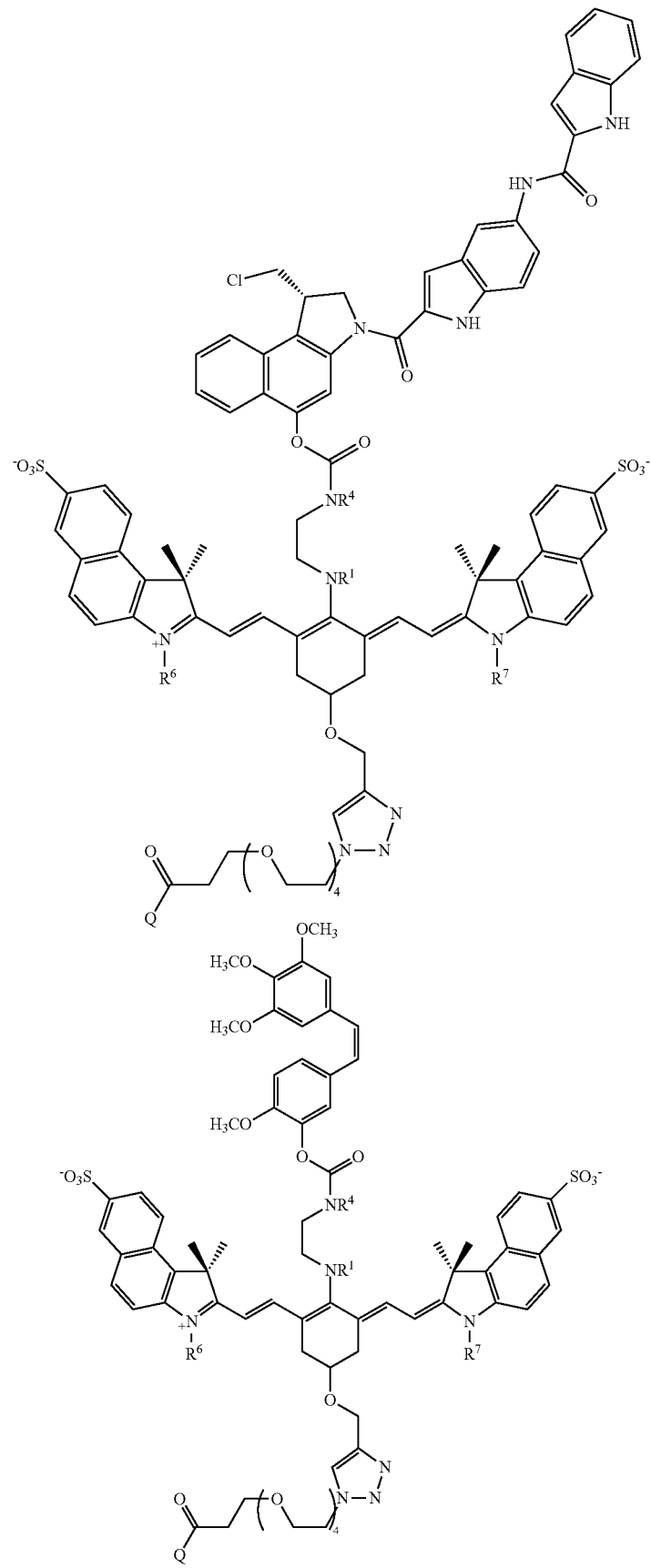

TABLE 1-continued
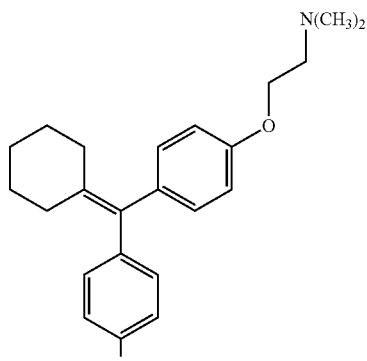
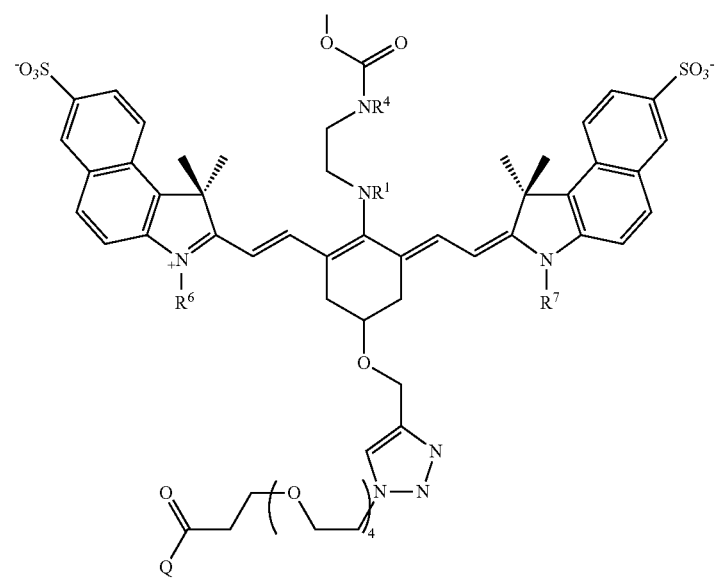
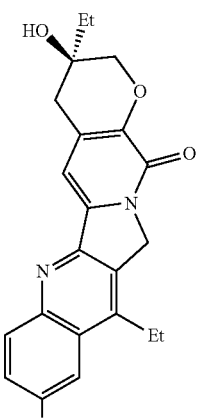

TABLE 1-continued
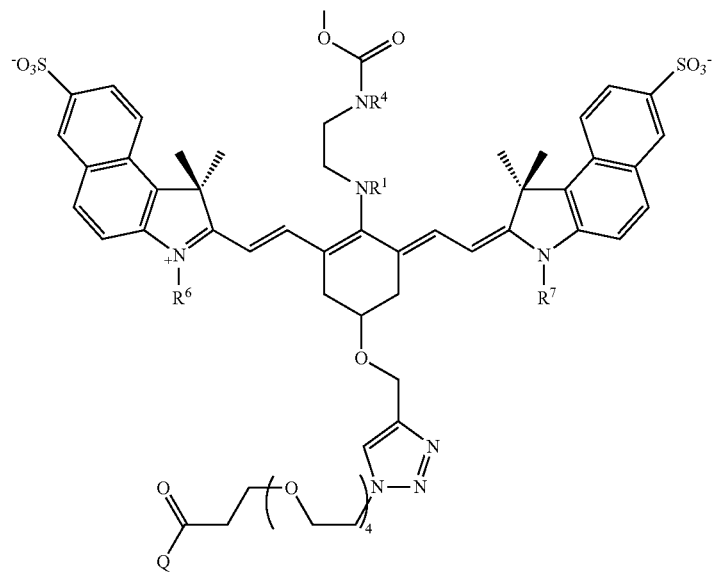
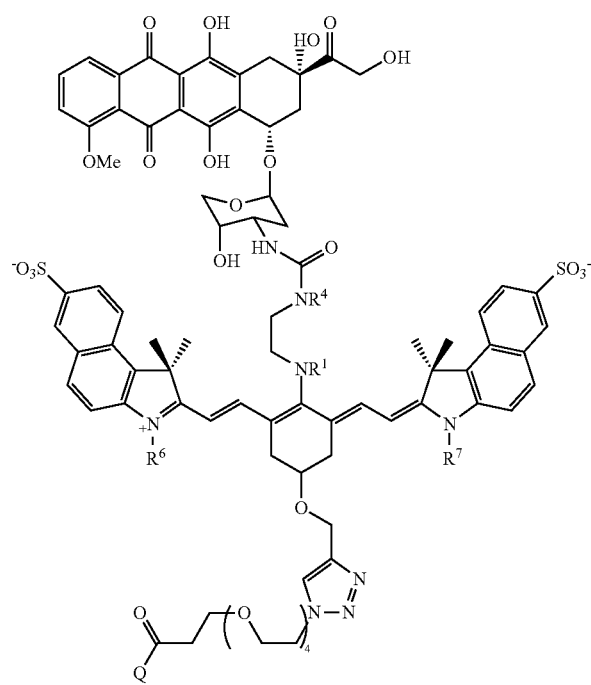

TABLE 1-continued
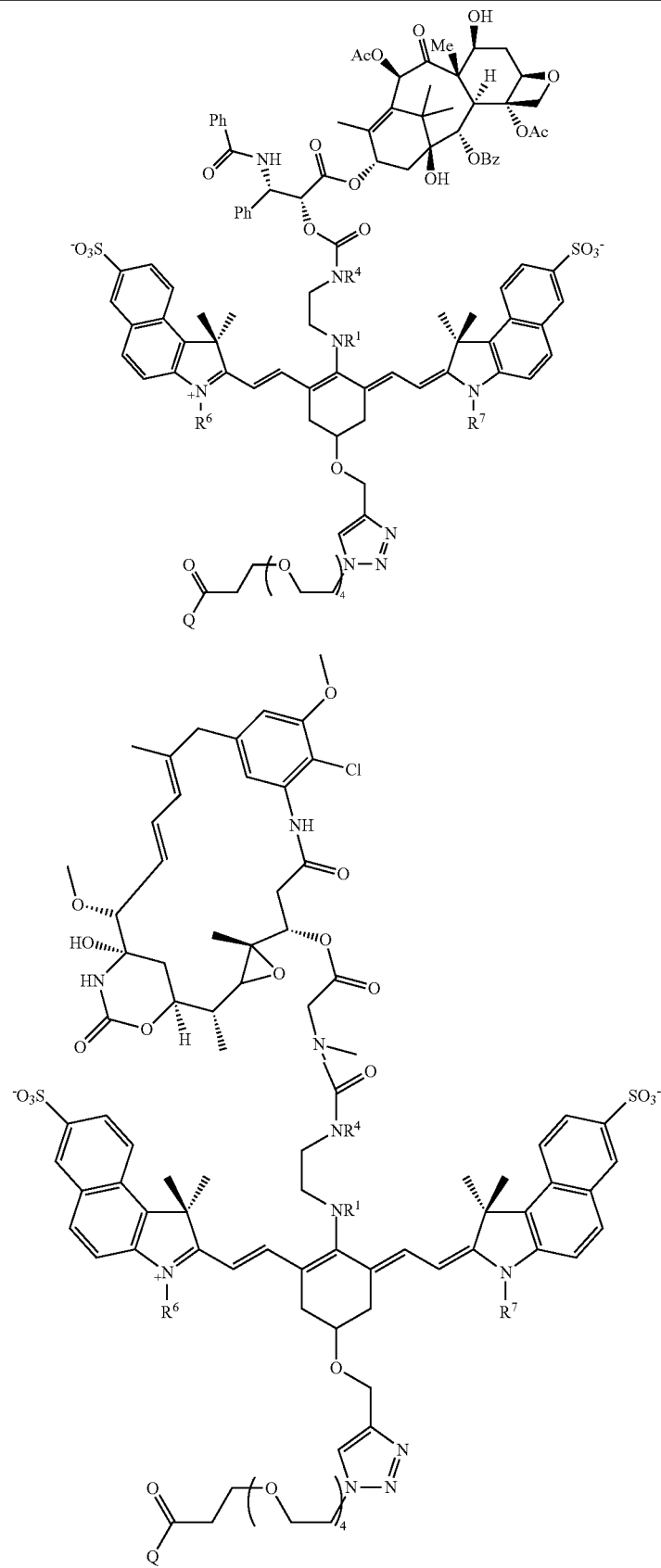

TABLE 1-continued

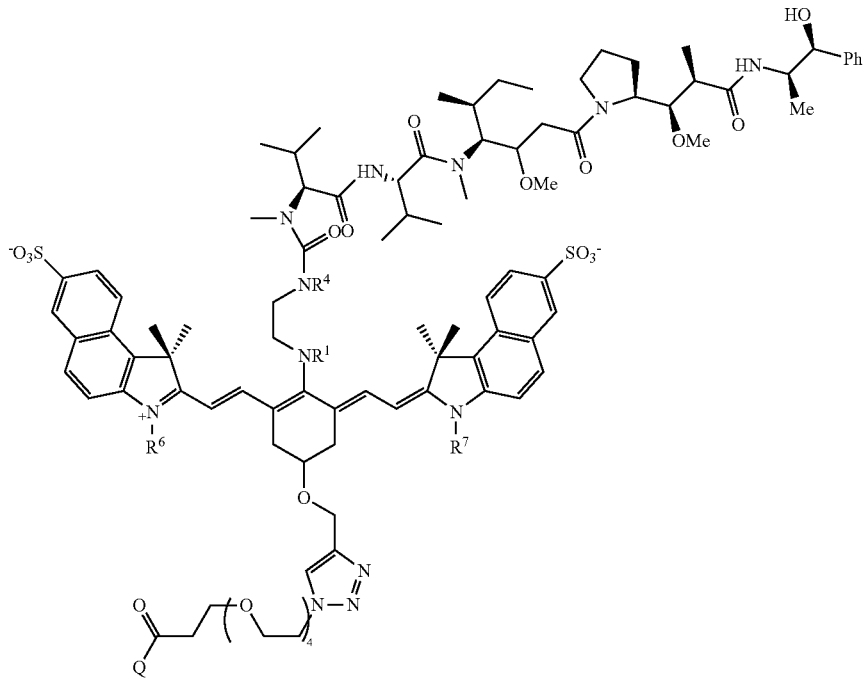

III. Precursor Compounds

Embodiments of a precursor compound useful for making the conjugates according to Formulas I-III have a structure according to Formula IV, or a salt thereof

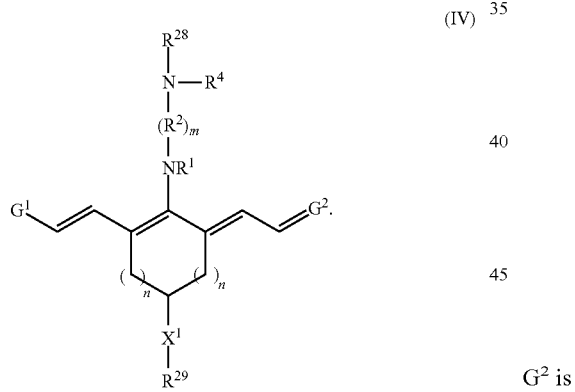
(IV)

With respect to Formula IV, m is 1, 2, 3, 4, or 5; and each n independently is 1, 2, or 3. $R^1$ and $R^4$ independently are alkyl, haloalkyl, cycloalkyl, alkoxy, —ROH, —RC(O)OH, —C(O)—R, or —C(O)—O—R, wherein R is alkyl. $R^2$ is $C(R^c)_2$ wherein each $R^c$ independently is H, halo, alkyl, or aryl, or $(R^2)_m$ collectively is phenyl. $X^1$ is O, N, or $CH_2$. $G^1$ is

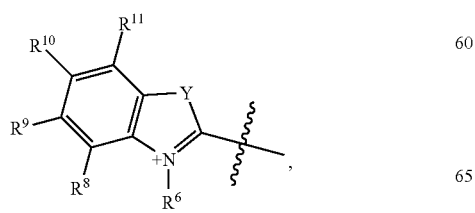

-continued

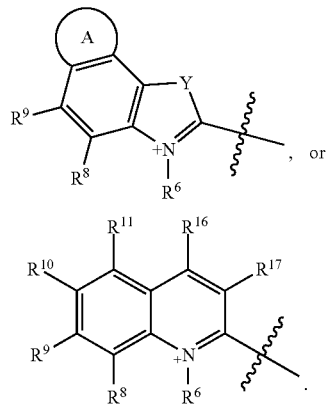
, or $G^2$ is

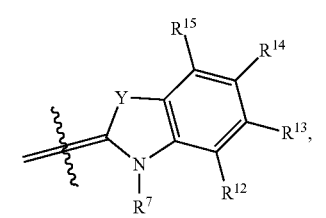

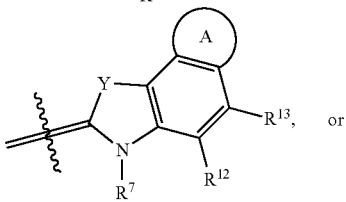
, or

-continued

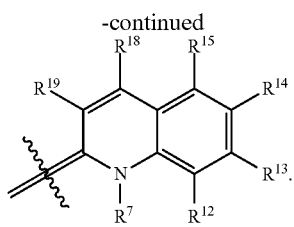

R⁶ and R⁷ independently are H, alkyl, alkoxy, alkyl sulfonate, or substituted aminoalkyl. R⁸-R⁹ independently are H, alkyl, amino, alkoxy, or alkyl sulfonate. Each Y independently is $C(R^d)_2$, S, O, Se, or $N(R^d)$ wherein each $R^d$ independently is H or alkyl. Each ring A independently is a 6-membered fused aliphatic, heteroaliphatic, aryl, or heteroaryl ring. $R^{28}$ is hydrogen or a protecting group. $R^{29}$ is $-(CH_2)_u-C\equiv CH$ where u is 1, 2, 3, 4, or 5.

Suitable protecting groups include, but are not limited to, tert-butyloxycarbonyl (BOC) and 9-fluorenylmethyloxycarbonyl (FMOC). In some embodiments, $R^{28}$ is hydrogen.

The two heterocycle moieties, $G^1$ and $G^2$, may be substantially the same or different from one another. In some embodiments, the two heterocycle moieties are substantially the same as described previously. $R^6$ and $R^7$ independently are H, alkyl, alkoxy, alkyl sulfonate, or substituted aminoalkyl. In some embodiments, $R^6$ and $R^7$ independently are alkyl sulfonate or substituted aminoalkyl, such as $-(CH_2)_pSO_3^-$ or $-(CH_2)_pN(CH_3)_3^+$, where p is 1, 2, 3, 4, or 5. In one embodiment, $R^6$ and $R^7$ are $-(CH_2)_4SO_3^-$. In another embodiment, $R^6$ and $R^7$ are $-(CH_2)_4N(CH_3)_3^+$. In certain embodiments, $R^8$-$R^{19}$ are hydrogen. Each Y independently is $C(R^d)_2$S, O, Se, or $N(R^d)$ wherein each $R^d$ independently is H or alkyl. In some examples, each Y independently is $C(CH_3)_2$ or S. In certain embodiments, each Y is $C(CH_3)_2$. In some embodiments, each ring A is a fused aryl ring, such as a fused phenyl ring substituted with optionally substituted sulfonate.

In certain examples, the precursor compound is

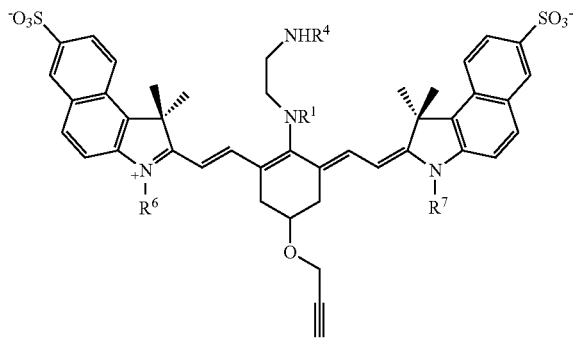

where $R^1$ and $R^4$ are methyl, ethyl, n-propyl, i-propyl, t-butyl, or $-(CH_2)_2OH$; and $R^6$ and $R^7$ are $-(CH_2)_pSO_3^-$ or $-(CH_2)_pN(CH_3)_3^+$, where p is 1, 2, 3, 4, or 5:

IV. Synthesis

Figure 2:
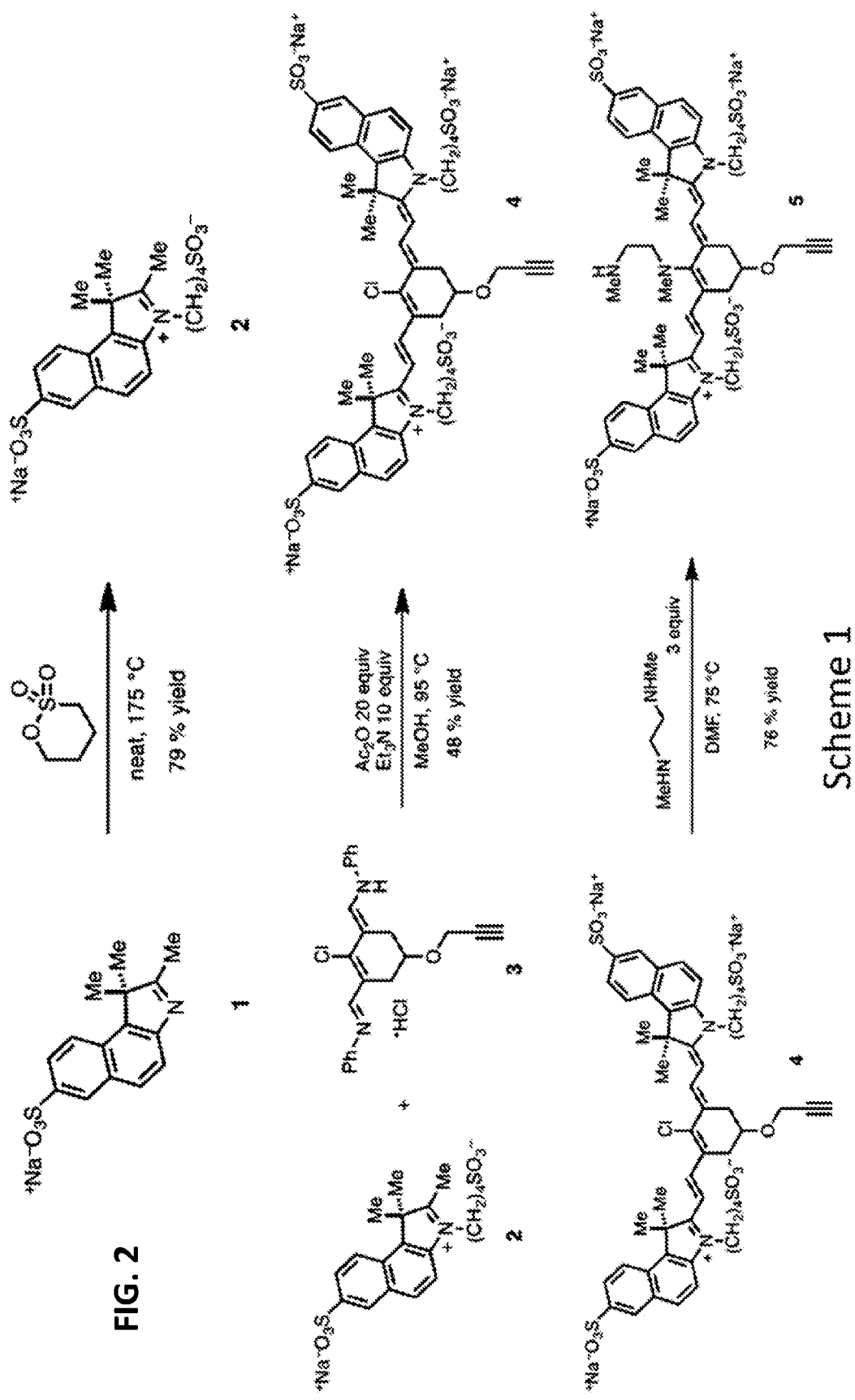
FIG. 2 is a synthetic scheme for a precursor compound as disclosed herein.

Embodiments of the disclosed conjugates and precursor compounds are synthesized from cyanine fluorophores. An exemplary synthesis of one precursor compound according to Formula IV is shown in Scheme 1 (FIG. 2). Indolenine 1 is reacted with 1,4-butanesultone to produce a sulfonated indolenine 2. The sulfonated indolenine 2 is reacted with chloride 3 to produce a heptamethine cyanine 4 including an alkynyl group on the central ring. An N,N'-dimethylethyl-enediamine linker is reacted with compound 4 to yield precursor compound 5 according to Formula IV. Other precursor compounds according to Formula IV can be synthesized with variations in compound 1 and the diamine linker as desired. To substitute indolene 1 with $-(CH_2)_4N(CH_3)_3^+$, bromo-butyl-ammonium bromide or TfO-butyl-ammonium triflate can be used.

Figure 3:
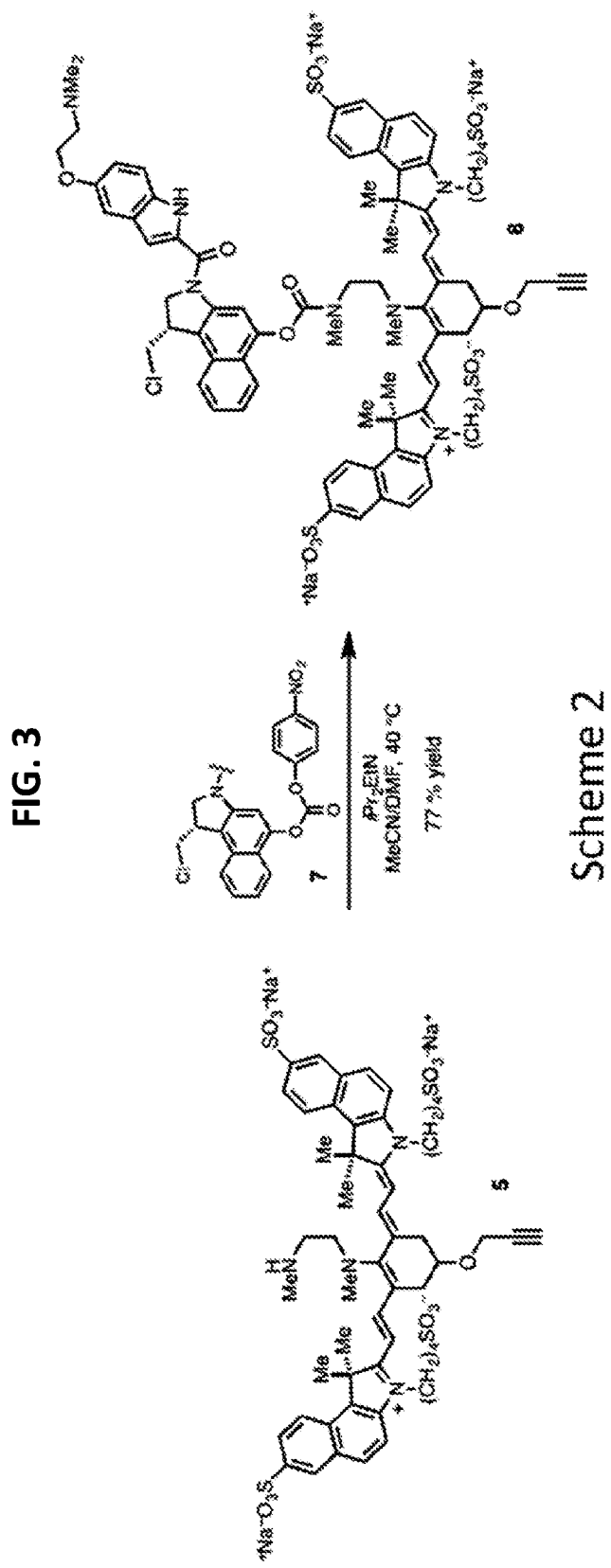
FIG. 3 is a synthetic scheme for an intermediate conjugate comprising a drug.

A drug (e.g., duocarmycin DM 7) may be conjugated to precursor compound 5 via an acylation reaction to produce an intermediate conjugate 8 as shown in Scheme 2 (FIG. 3). Intermediate conjugate 8 is suitable for further conjugation to a targeting agent, e.g., an antibody or a ligand.

Figure 4:
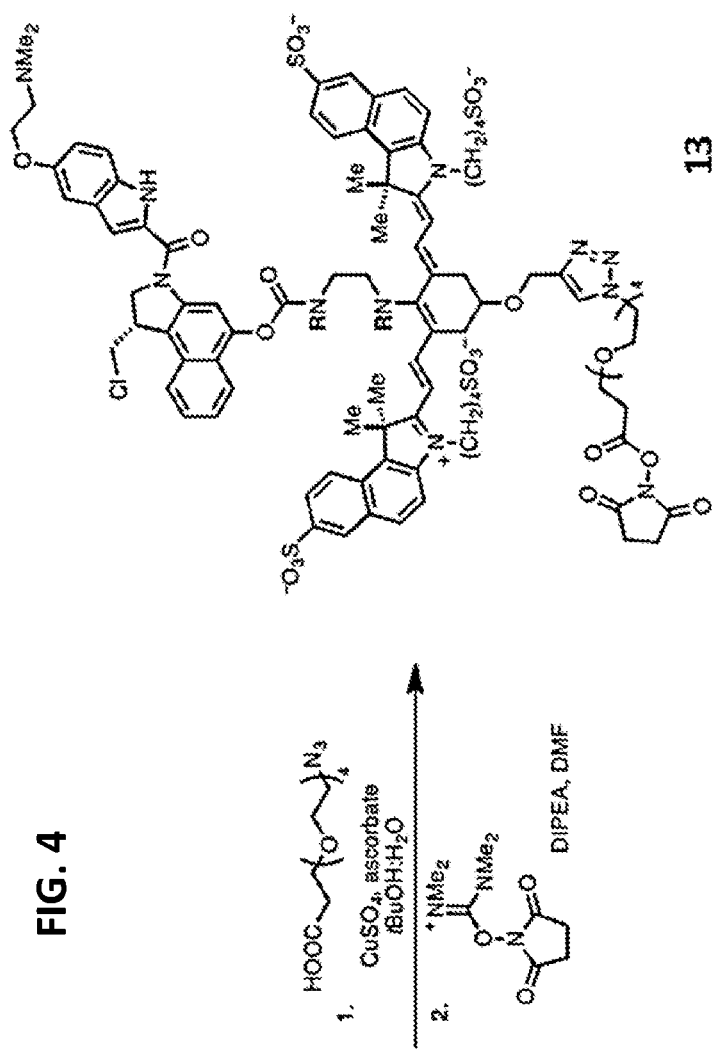
FIG. 4 is a synthetic scheme for adding a reactive moiety to the intermediate conjugate of FIG. 3 in preparation for conjugation to a targeting agent.
Figure 4:
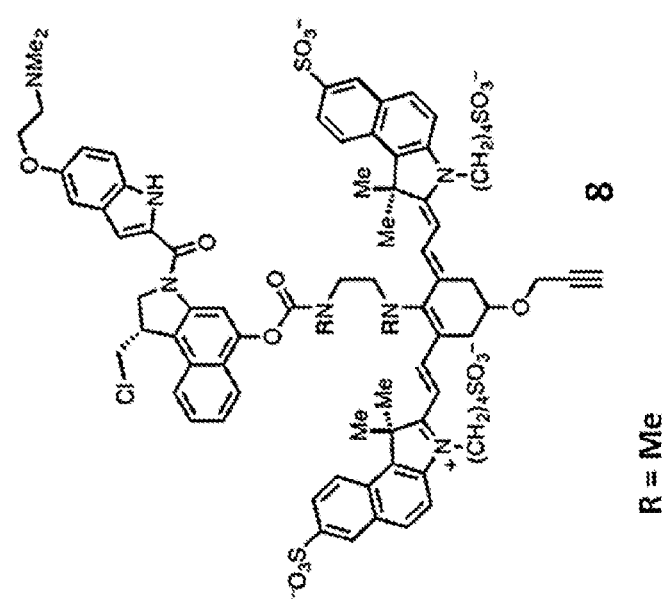

A copper-catalyzed click reaction may be used to form an NHS ester. In a first reaction, a linker comprising an azide group and a carboxylic acid moiety is reacted with the alkynyl group of 8. Subsequently, N,N,N',N'-tetramethyl-O—(N-succinimidyl)uronium tetrafluoroborate is added to the reaction, to produce an NHS ester 13 (R=methyl in this example) as shown in Scheme 3 (FIG. 4). In a final step, a targeting agent, such as an antibody, may be conjugated to the NHS ester to produce conjugate according to Formulas I and II (FIGS. 5 and 6).

V. Pharmaceutical Compositions

This disclosure also includes pharmaceutical compositions comprising at least one conjugate as disclosed herein. Some embodiments of the pharmaceutical compositions include a pharmaceutically acceptable carrier and at least one conjugate. Useful pharmaceutically acceptable carriers and excipients are known in the art.

The pharmaceutical compositions comprising one or more conjugates may be formulated in a variety of ways depending, for example, on the mode of administration and/or on the location to be imaged. Parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as Cremophor®, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation. Generally, embodiments of the disclosed pharmaceutical compositions will be administered by injection, systemically, or orally.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion.

Alternatively, the conjugate may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some conjugate formulations may be dried, e.g., by spray-drying with a disaccharide, to form conjugate powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophor® or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the fluorophore, as is well known.

For rectal and vaginal routes of administration, the conjugate(s) may be formulated as solutions (for retention enemas) suppositories or ointments containing conventional suppository bases such as cocoa butter or other glycerides.

For nasal administration or administration by inhalation or insufflation, the conjugate(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

Certain embodiments of the pharmaceutical compositions comprising conjugates as described herein may be formulated in unit dosage form suitable for individual administration of precise dosages. The pharmaceutical compositions may, if desired, be presented in a pack or dispenser device which may contain one or more unit dosage forms containing the conjugate. The pack may, for example, comprise metal or plastic foil, such as a blister pack. The pack or dispenser device may be accompanied by instructions for administration. The amount of conjugate administered will depend at least in part on the subject being treated, the target (e.g., the size, location, and characteristics of a tumor), and the manner of administration, and is known to those skilled in the art. Within these bounds, the formulation to be administered will contain a quantity of the conjugate disclosed herein in an amount effective to provide a therapeutically effective dose of the drug to the subject being treated when the conjugate is irradiated with NIR light to release the drug from the conjugate.

In some embodiments, the pharmaceutical composition includes a second therapeutic agent other than the conjugate. The second agent may be, for example, an anti-tumor agent or an angiogenesis inhibitor.

VI. Photo-induced Cleavage

Embodiments of the disclosed conjugates according to Formula I are photoactivated by application of light having a desired wavelength, intensity, and/or surface area to a pre-selected target area for an effective period of time. Photoactivation results in cleavage of the drug from the conjugate. The wavelength is selected within the near-infrared range, e.g., from 650 nm to 2500 nm, such as from 650-900 nm. In some embodiments, the light source is a laser that produces light having a wavelength within a range of 650-800 nm, or 680-750 nm. Suitable light intensities may range from 1 mW/cm$^2$ to 1000 mW/cm$^2$, such as 1-750 mW/cm$^2$ or 300-700 mW/cm$^2$, depending on the target site and method of application. Near-infrared light sources can be obtained from commercial sources, including Thorlabs (Newton, N.J.), Laser Components, USA (Hudson, N.H.), ProPhotonix (Salem, N.H.) and others. In some embodiments, the effective quantity of NIR light is 10-250 J, such as 10-200 J, 10-150 J, or 10-100 J. When irradiating a target area (e.g., an area proximate a tumor), the effective quantity of NIR light may be 1-250 J/cm$^2$, such as 1-250 J/cm$^2$, such as 5-250 J/cm$^2$, 10-250 J/cm$^2$, 10-200 J/cm$^2$, 10-150 J/cm$^2$, 10-100 J/cm$^2$, or 30-100 J/cm$^2$.

In some in vivo embodiments, irradiation is performed by external application of light to a targeted area of a subject. NIR light is capable of penetrating transcutaneously into tissue to a depth of several centimeters. In other embodiments, irradiation may be performed by internal application of light, such as by using an endoscope, a fiber optic catheter, or an implantable fluorescence device. Internal application may be used when the target tissue, such as a tumor, is located at a depth that is unsuitable for external light application. For example, an endoscope may be used for light delivery into the lungs, stomach, or bladder. In certain embodiments, a target area is surgically exposed prior to application of light.

The surface area for light application is generally selected to include target tissue, e.g., a tumor or portion of a tumor, or an area of skin external to the target tissue. When targeted application of external light is desired for an in vivo biological sample, the surface area can be controlled by use of an appropriate light applicator, such as a micro-lens, a Fresnel lens, or a diffuser arrangement. For targeted internal light application, a desired endoscope or fiber optic catheter diameter can be selected. In some applications, an indwelling catheter filled with a light scattering solution may be internally placed proximate the target tissue, and an optical fiber light source may be inserted into the catheter (see, e.g., Madsen et al., *Lasers in Surgery and Medicine* 2001, 29, 406-412).

Irradiation is performed for a period of time sufficient to deliver an amount of irradiation effective to induce cleavage of the drug from at least some molecules of the conjugate. In some embodiments, the effective amount of irradiation is at least 10 J/cm$^2$, such as at least 30 J/cm$^2$, at least 50 J/cm$^2$, or at least 100 J/cm$^2$. Effective amounts of irradiation may range from 1-250 J/cm$^2$, such as 5-250 J/cm$^2$, 10-250 J/cm$^2$, 10-200 J/cm$^2$, 10-150 J/cm$^2$, 10-100 J/cm$^2$, or 30-100 J/cm$^2$.

VII. Methods of Use

Conjugates according to Formula I or Formula II are suitable for in vivo, ex vivo, or in vitro use. In some embodiments, when $R^b$ is a targeting agent and Y is $C(R^d)_2$, then at least one $R^d$ is other than H. More than one heptamethine cyanine-drug moiety may be conjugated to each targeting agent. For example, the conjugate may have a degree of labeling (DOL) from 1-6, such as from 1-4 or from 2-4, wherein the DOL is the number of heptamethine cyanine-drug moieties conjugated to the targeting agent. In one embodiment, each heptamethine cyanine-drug moiety comprises the same drug. In an independent embodiment, the heptamethine cyanine-drug moieties comprise different drugs, thereby enabling a single conjugate to deliver a plurality of drugs.

The conjugate is irradiated with targeted application of an effective quantity of light having a selected wavelength in the near-infrared range and a selected intensity to induce a cleavage reaction and release the drug from at least some molecules of the conjugate. For example, drug may be released from at least 10%, at least 20% at least 40%, at least 60%, or at least 80% of the conjugate molecules when the conjugate is irradiated with an effective quantity of light. In some embodiments, from 10-100% of the drug is released, such as from 20-100%, from 40-100%, from 60-100%, or from 80-100%. When the conjugate has a DOL greater than one, a greater quantity of drug may be released from the conjugate, compared to a conjugate with a DOL of one, when the conjugate is irradiated with the effective quantity of light. In one embodiment, the conjugate is evaluated in the absence of a biological sample to confirm that the particular conjugate will undergo photodegradation when irradiated with near-IR light.

Advantageously, the conjugate is fluorescent prior to irradiation and loses fluorescence following the cleavage reaction. When the conjugate has a DOL greater than one, fluorescence advantageously is increased compared to a conjugate with a DOL of one. A fluorescence level of the conjugate may be monitored during irradiation, and irradiation may be ceased when the fluorescence level falls below a target level. Fluorescence decreases as drug is released from the conjugate. Thus, the fluorescence level might be monitored to determine when a desired or sufficient proportion of the conjugate has undergone cleavage and drug release.

A biological sample may be contacted in vivo, ex vivo, or in vitro with the conjugate according to Formula I or Formula II. Following contact with the conjugate, the biological sample is irradiated with near-IR radiation to induce a cleavage reaction and release the drug from the conjugate. In some embodiments, a period of time is allowed to lapse between administration of the conjugate and application of near-IR radiation, thereby providing time for the conjugate to accumulate at and bind to the target site. The period of time may be several hours to several days, such as from 1-7 days or from 12 hours-2 days.

In some embodiments, the conjugate according to Formula I or II comprises a targeting agent capable of recognizing and binding directly or indirectly, in vitro, in vivo, or ex vivo, to a target (e.g., an antigen or a receptor) present or suspected of being present in the biological sample. In one embodiment, the biological sample is visualized under conditions suitable to produce near-IR fluorescence if the conjugate is present in the biological sample. Fluorescence also confirms presence of the target in the biological sample. Excess unbound conjugate may be removed from the biological sample (e.g., by washing a tissue sample) prior to visualizing the sample to detect fluorescence.

In one non-limiting example, a biological sample (e.g., a tissue sample) that may comprise a target is contacted with a conjugate according to Formula I or II comprising an antibody capable of recognizing and binding to the target. In another non-limiting example, a biological sample that may comprise a target is combined with a first antibody capable of recognizing and binding to the target; subsequently, the biological sample is contacted with a conjugate comprising an anti-antibody antibody. In another non-limiting example, the biological sample is contacted with a conjugate comprising a ligand capable of binding to a receptor. For instance, substituent $R^b$ may be a receptor ligand capable of binding to a receptor on a cell surface.

In some embodiments, a subject is identified as having a condition that may be treated with a drug. A therapeutically effective amount of a conjugate according to Formula I or II comprising the drug or a pharmaceutical composition comprising the conjugate is administered to the subject. A therapeutically effective amount of the conjugate is an amount sufficient to release a therapeutically effective dose of the drug when irradiated by targeted application of an effective quantity of light having a wavelength in the near-infrared range and a selected intensity to a targeted portion of the subject. The therapeutically effective amount of the conjugate may be reduced when the conjugate has a DOL greater than one since each conjugate may release more than one drug molecule when irradiated.

In certain embodiments, the light source provides light having a wavelength within a range of 650-900 nm, such as a wavelength from 650-800 nm or 680-750 nm, and an intensity of 1-1000 mW/cm$^2$, such as 300-700 mW/cm$^2$. In one embodiment, the light has a wavelength of 690 nm and an intensity of 500 mW/cm$^2$. In another embodiment, the light has a wavelength of 740 nm and an intensity of 500 mW/cm$^2$. The effective amount may range from 10-250 J, such as 10-200 J, 10-150 J, or 10-100 J. When irradiating a target area (e.g., an area proximate a tumor), the effective quantity of NIR light may be 1-250 J/cm$^2$, such as 1-250 J/cm$^2$, such as 5-250 J/cm$^2$, 10-250 J/cm$^2$, 10-200 J/cm$^2$, 10-150 J/cm$^2$, 10-100 J/cm$^2$, or 30-100 J/cm$^2$.

In one embodiment, the subject has a tumor and a conjugate according to Formula I or II comprises a targeting agent capable of recognizing and binding to an antigen or ligand-binding receptor of the tumor. Suitable tumors include, but are not limited to, solid tumor masses, such as intraperitoneal tumors (e.g., ovarian, prostate, colorectal), breast tumors, or head/neck tumors. The targeting agent may be, for example, an antibody that recognizes and binds to the tumor antigen. A therapeutically effective amount of the conjugate, a pharmaceutically acceptable salt thereof, or a pharmaceutical composition comprising the conjugate, is administered to the subject by any suitable means including, but not limited to, parenteral, intravenous, subcutaneous, oral, rectal, vaginal, or topical administration. The administered conjugate is irradiated by targeted application of NIR light to an area proximate a location of the tumor.

Figure 7:
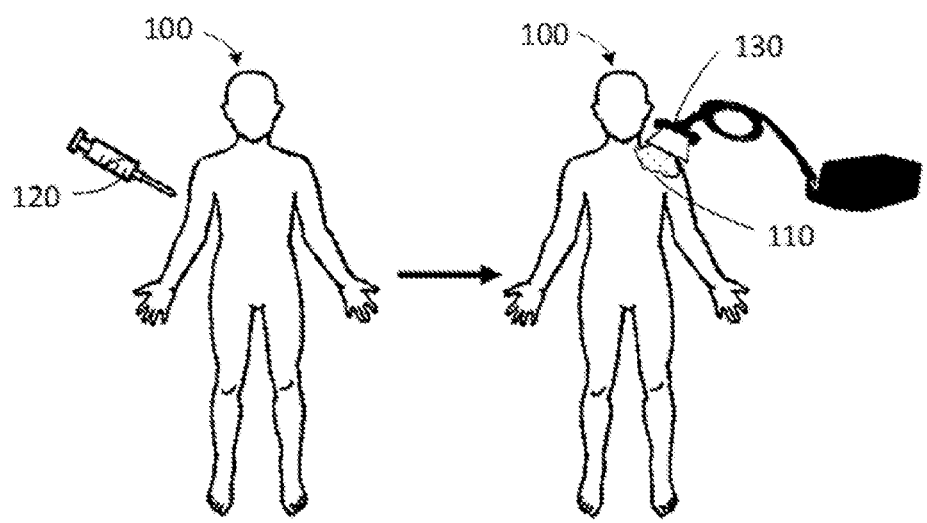
FIG. 7 is a schematic diagram illustrating one embodiment of a method for using the disclosed targeting agent-drug conjugates to treat a subject having a tumor by injection of the conjugate followed by targeted delivery of light of a desired wavelength to the external surface of the skin.

With reference to FIG. 7, a subject 100 with a tumor 110 may be treated with a conjugate comprising an anti-tumor drug and an antibody or ligand capable of recognizing and binding to an antigen or receptor on a tumor cell surface. Administration of the conjugate to the subject may impair growth of the tumor and/or cause tumor regression.

In the example shown in FIG. 7, the conjugate 120 is administered via intravenous injection. A period of time is allowed to elapse during which the conjugate preferentially accumulates at the tumor site as the antibody or ligand moiety binds to the tumor. A target portion of the subject subsequently is selectively irradiated with an effective amount of NIR light energy of a desired wavelength using an external light applicator 130. The light applicator 130 applies the photoactivation energy to a target area limited to the region of the tumor 110, thereby selectively inducing cleavage of the conjugate molecules in and around the tumor 110 and targeting delivery of the anti-tumor drug released from the conjugate.

Embodiments of the disclosed conjugates or a pharmaceutical composition comprising the conjugate are suitable for theranostic use, i.e., to diagnose and then treat a condition. In some embodiments, a therapeutically effective amount of a conjugate as disclosed herein or a pharmaceutical composition comprising the conjugate is administered to a subject suspected of having a condition that may be treated with the drug. The conjugate is subsequently irradiated by targeted application of a quantity of light having a wavelength in the near-infrared range and a selected intensity to a targeted portion of the subject, wherein the quantity of light is sufficient to excite the cyanine fluorophore and induce fluorescence of the conjugate but is insufficient to release the drug from the conjugate. Any fluorescence from the conjugate in the targeted portion of the subject is detected, thereby diagnosing the subject as having the condition. If fluorescence is detected, the conjugate may be subsequently irradiated by targeted application of an effective quantity of light having a wavelength in the near-infrared range and a selected intensity sufficient to release the drug from at least some molecules of the conjugate and treat the condition.

In some theranostic embodiments, the condition is a tumor and the targeted portion of the subject includes the tumor site. Prior to targeted application of NIR light, the administered conjugate is visualized by exposing the tumor to light having a wavelength and intensity sufficient to induce fluorescence of the conjugate but insufficient to induce cleavage. In some examples, the tumor site is exposed by surgical incision prior to exposing the tumor to light. The tumor is excised using the area of fluorescence as guidance. Remaining conjugate and/or tumor tissue is then irradiated by targeted application of NIR light as described above to release the drug from at least some molecules of the conjugate and treat any non-excised cancerous tissue.

In one embodiment, at least a portion of the tumor is excised from the subject before administering the therapeutically effective amount of the conjugate or the pharmaceutical composition comprising the conjugate to the subject. In an independent embodiment, the therapeutically effective amount of the conjugate or the pharmaceutical composition comprising the conjugate is administered to the subject before surgical excision of the tumor or a portion thereof.

A therapeutically effective amount of a second agent may be co-administered with the conjugate or salt thereof. The conjugate (or salt thereof) and the second agent may be administered either separately or together in a single composition. The second agent may be administered by the same route or a different route. If administered concurrently, the conjugate (or salt thereof) and the second agent may be combined in a single pharmaceutical composition or may be administered concurrently as two pharmaceutical compositions. The second agent may be, for example, a chemotherapeutic agent, such as an anti-tumor agent or an angiogenesis inhibitor, an anti-inflammatory agent, an anti-infective agent, an anti-oxidant, or any combination thereof.

In another embodiment, an in vitro or ex vivo evaluation may be performed to determine whether a targeting agent-drug conjugate according to Formula I or II will effectively bind to a tissue sample obtained from a subject having, or suspected of having, a condition that may be treated or ameliorated by the drug and/or to determine whether the drug may be effective for the subject's condition. The conjugate comprises a drug and a moiety at $R^b$ thought to be capable of binding to or associating with the target molecule. In one non-limiting example, $R^b$ is a receptor ligand or antibody capable of binding to a target receptor. The conjugate is combined with the tissue sample, and the sample is subsequently irradiated with an effective amount of near-IR light. In one embodiment, the tissue sample is washed to remove excess, unbound conjugate, and fluorescence of the tissue sample is assessed. Fluorescence indicates that the conjugate has bound to the tissue sample. Following irradiation with near-IR light, fluorescence may again be assessed. A decrease in (or cessation of) fluorescence indicates release of the drug. The drug's efficacy also may be assessed, e.g., by assessing cytotoxicity.

Embodiments of conjugates according to Formula I or Formula II wherein $R^a$ or $R^b$ comprises a succinimidyl, maleimidyl, or dibenzocyclooctynyl group are suitable for customized conjugation to a targeting agent of choice. In one non-limiting example, a tumor sample is obtained from a subject, and a conjugate comprising a drug that may be effective against the tumor is selected. An antibody that specifically recognizes and binds to an antigen on the tumor, or a ligand that specifically recognizes and binds to a receptor on the tumor, is prepared by methods known to one of ordinary skill in the art. The prepared antibody or ligand is then reacted with $R^b$ of the selected conjugate to provide a customized conjugate suitable for administration to the subject.

Precursor compounds according to Formula IV are suitable for customized conjugation to a selected drug and a selected targeting agent. In one embodiment, the precursor compound is used by a pharmaceutical company to develop a conjugate having a desired combination of drug and targeting agent. In another embodiment, the precursor compound is used by a researcher or clinician to develop conjugates having desired combinations of drugs and targeting agents useful for research purposes or for developing a customized conjugate for treating a subject.

VIII. Kits

Kits are also a feature of this disclosure. Embodiments of the kits include at least one conjugate according to general Formula I or II or a precursor compound according to general Formula IV. In one embodiment, the kit includes a conjugate according to Formula I or II wherein $R^b$ is a targeting agent, e.g., an antibody. In another embodiment, the kit includes an intermediate conjugate wherein $R^a$ or $R^b$ is

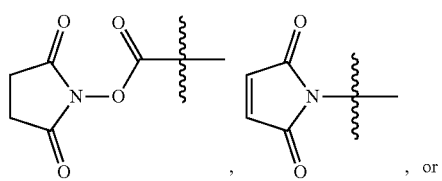

, or

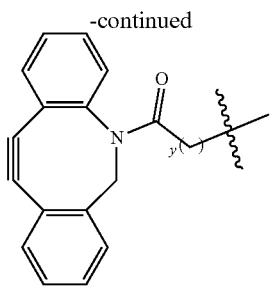

where y is an integer≥1,
and the kit may be used to prepare a further conjugate comprising a desired targeting agent, wherein the targeting agent is capable of reacting with the intermediate compound to provide a conjugate comprising the targeting agent. In yet another embodiment, the kit includes a precursor compound according to Formula IV, and the kit is used to prepare a conjugate having a desired targeting agent and a desired drug.

In some embodiments, the kits also include at least one solution in which the conjugate or precursor compound may be dissolved or suspended. The kits also may include one or more containers, such as a disposable test tube or cuvette. The kits may further include instructions for using the conjugate according to Formula I or II, for conjugating a desired targeting agent if $R^a$ or $R^b$ is a reactive group, and/or for preparing a conjugate comprising a desired targeting agent and a desired drug from the precursor compound according to Formula IV. In some embodiments, the kits further include reagents suitable for conjugating the compound according to Formula I, II, or IV to a targeting agent and/or for conjugating the compound according to Formula IV to a drug.

In some embodiments of the kits, the conjugate or precursor compound is provided as a solid, and the solution is provided in liquid form. In one embodiment, the solution is suitable for dissolving a conjugate according to Formula I or II so that the dissolved conjugate may be administered to a subject or so that a dissolved conjugate wherein $R^a$ or $R^b$ is a reactive group (an intermediate compound comprising a drug and a reactive group) may be conjugated to a targeting agent. In an independent embodiment, the solution is suitable for dissolving a precursor compound according to Formula IV for subsequent conjugation to a drug and/or targeting agent. The solution may be provided at a concentration suitable for the intended use. Alternatively, the solution may be provided as a concentrated solution, which is subsequently diluted prior to use. In certain embodiments, the conjugate or precursor compound is premeasured into one or more containers (e.g., test tubes or cuvettes).

IX. Examples

Example 1

Synthesis

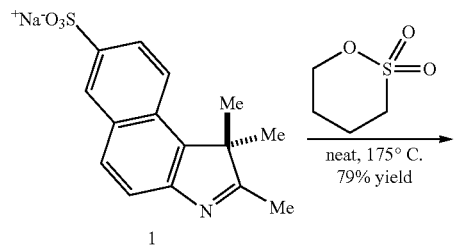

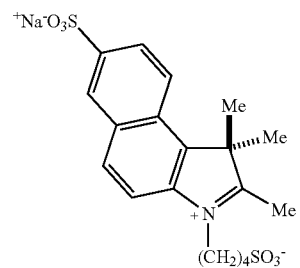

(2): To a microwave vial containing indolenine 1 (75 mg, 0.24 mmol) was added 1,4-butanesultone (1.5 mL). The headspace was flushed with argon, and the light brown suspension was heated in a microwave reactor at 175° C. for 7 hours. Diethyl ether (10 mL) was charged to vial, and the thick slurry was centrifuged to afford a brown pellet. The crude solid was dissolved in water and purified by reversed-phase chromatography ($C_{18}$ Aq gold column, 0-20% MeCN/water). The solvent was removed in vacuo to afford 2 (85 mg, 79% yield) as a tan solid. $^1$H NMR (500 MHz, DMSO-$d_6$) δ 8.41 (d, J=1.8 Hz, 1H), 8.36 (d, J=8.9 Hz, 1H), 8.33 (d, J=8.8 Hz, 1H), 8.20 (d, J=8.9 Hz, 1H), 7.94 (dd, J=8.7, 1.7 Hz, 1H), 4.59 (t, J=8.0 Hz, 2H), 2.94 (s, 3H), 2.55 (t, J=7.3 Hz, 2H), 2.02 (p, J=7.6 Hz, 2H), 1.80 (p, J=7.6 Hz, 2H), 1.75 (s, 6H); MS (ESI) calculated for $C_{19}H_{22}NO_6S_2$ (M)$^-$ 424.1, observed 424.1.

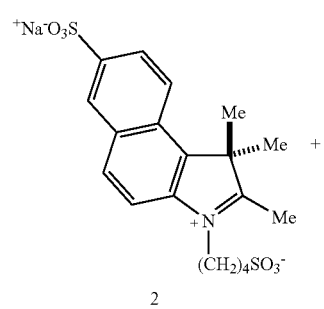

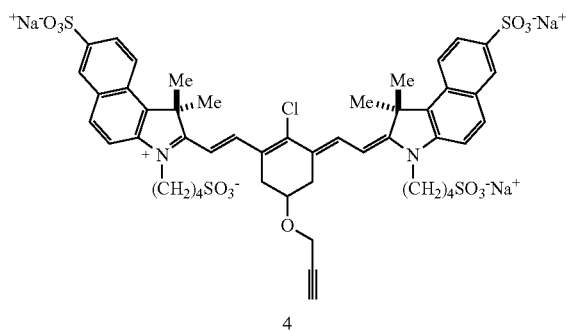

4

(4): To a microwave vial was added indolenine 2 (50 mg, 0.11 mmol) and chloride 3 (12 mg, 0.028 mmol). MeOH (3 mL), triethylamine (39 µL, 0.28 mmol), and acetic anhydride (53 µL, 0.56 mmol) were then added in succession. The yellow solution was heated to 95° C. for 75 minutes, during which time the reaction transitioned to a deep green color. The reaction was cooled and diluted into saturated aqueous NaHCO$_3$, yielding a tan precipitate. The crude solid was dissolved in water and purified by reversed-phase chromatography (C$_{18}$ Aq gold column, 0-30% MeCN/water). The product-containing fractions were lyophilized to afford 4 (15 mg, 48% yield) as fluffy green solid. $^1$H NMR (500 MHz, DMSO-d$_6$) δ 8.39 (d, J=14.1 Hz, 2H), 8.32-8.23 (m, 4H), 8.16 (d, J=8.8 Hz, 2H), 7.88-7.78 (m, 4H), 6.45 (d, J=14.2 Hz, 2H), 4.54-4.24 (m, 6H), 4.12 (m, 1H), 3.50 (t, J=2.3 Hz, 1H), 3.11-2.99 (m, 2H), 2.86 (dd, J=15.8, 6.9 Hz, 2H), 2.54 (t, J=7.3 Hz, 4H), 1.96 (s, 6H), 1.95 (s, 6H), 1.93-1.85 (m, 4H), 1.86-1.77 (m, 4H); MS (ESI) calculated for C$_{49}$H$_{50}$ClN$_2$O$_{13}$S$_4$(M/3z)$^{3-}$ 345.7, observed 346.0.

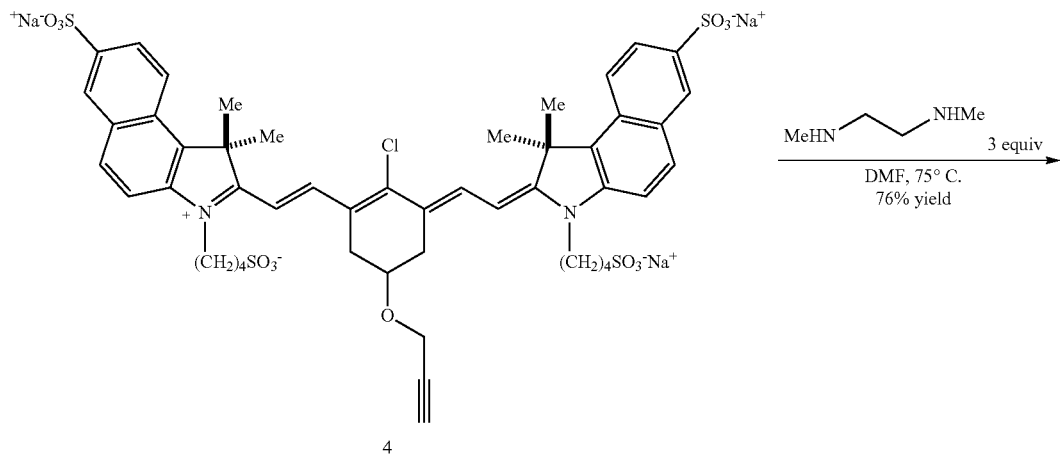

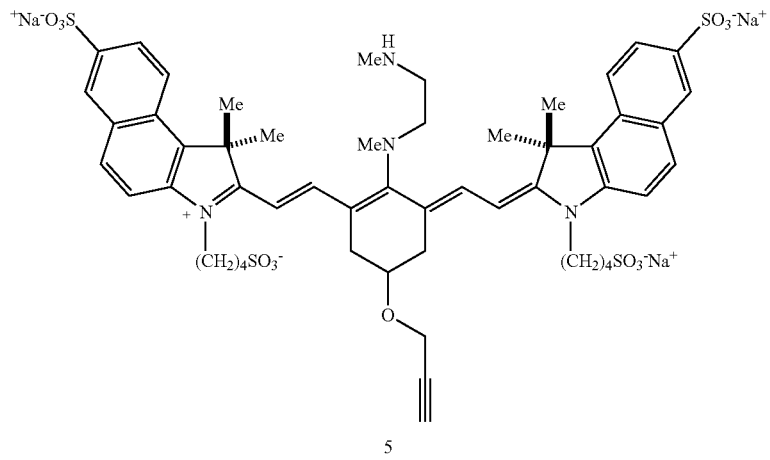

(5): To a 1-dram vial was added chloride 4 (15 mg, 0.014 mmol) and DMF (0.8 mL). N,N'-dimethylethylene diamine (5.0 μL, 0.047 mmol) was added and the reaction was heated to 75° C. for 10 minutes, during which time the reaction color transitioned from green to dark blue. The reaction was cooled and diluted with $H_2O$ (8 mL), and the solution was directly purified by reversed-phase chromatography ($C_{18}$ gold column, 0□30% MeCN/water). The product-containing fractions were lyophilized to afford 5 (12 mg, 76% yield) as fluffy blue solid. $^1$H NMR (400 MHz, Methanol-$d_4$) δ 8.43 (d, J=1.8 Hz, 2H), 8.28 (d, J=8.9 Hz, 2H), 8.09 (d, J=8.8 Hz, 2H), 8.00 (dd, J=8.9, 1.6 Hz, 2H), 7.89 (d, J=13.6 Hz, 2H), 7.66 (d, J=8.9 Hz, 2H), 6.20 (d, J=13.7 Hz, 2H), 4.34 (d, J=2.4 Hz, 2H), 4.32-4.26 (m, 4H), 4.24-4.16 (m, 1H), 4.02-3.92 (m, 2H), 3.49 (s, 3H), 3.42-3.33 (m, 4H), 2.99-2.83 (m, 5H), 2.84-2.67 (m, 5H), 2.15-2.03 (m, 4H), 2.00 (s, 6H), 1.99 (s, 6H), 1.98-1.90 (m, 4H); MS (ESI) calculated for $C_{53}H_{66}N_4O_{13}S_4$ $(M+5H)^{2+}$ 547.2, observed 547.5.

(6): To a 1-dram vial was added chloride 4 (22 mg, 0.020 mmol) and DMF (1.5 mL). N,N'-diethylethylene diamine (14 μL, 0.10 mmol) and diisopropylethylamine (7.0 μL, 0.040 mmol) were added and the reaction was heated to 110° C. for 20 minutes, during which time the reaction color transitioned from green to dark blue. The reaction was cooled and diluted with $H_2O$ (8 mL), and the solution was directly purified by reversed-phase chromatography ($C_{18}$ gold column, 0-30% MeCN/water). The product-containing fractions were lyophilized to afford 5 (14 mg, 59% yield) as fluffy bluish-green solid. $^1$H NMR (500 MHz, Methanol-$d_4$) δ 8.42 (d, J=1.8 Hz, 2H), 8.29 (d, J=9.0 Hz, 2H), 8.09 (d, J=8.9 Hz, 2H), 8.00 (dd, J=8.9, 1.9 Hz, 2H), 7.94 (d, J=13.7 Hz, 2H), 7.66 (d, J=8.9 Hz, 2H), 6.20 (d, J=13.8 Hz, 2H), 4.34 (d, J=2.4 Hz, 2H), 4.28 (t, J=7.3 Hz, 4H), 4.22-4.16 (m, 1H), 3.94-3.85 (m, 2H), 3.81 (q, J=7.0 Hz, 2H), 3.20-3.11 (m, 2H), 2.99-2.86 (m, 9H), 2.75 (dd, J=15.3, 6.1 Hz, 2H), 2.16-1.90 (m, 20H), 1.44 (t, J=6.9 Hz, 3H), 1.23 (t, J=7.2 Hz, 3H); MS (ESI) calculated for $C_{55}H_{70}N_4O_{13}S_4$ $(M+5H)^{2+}$ 561.2, observed 561.4.

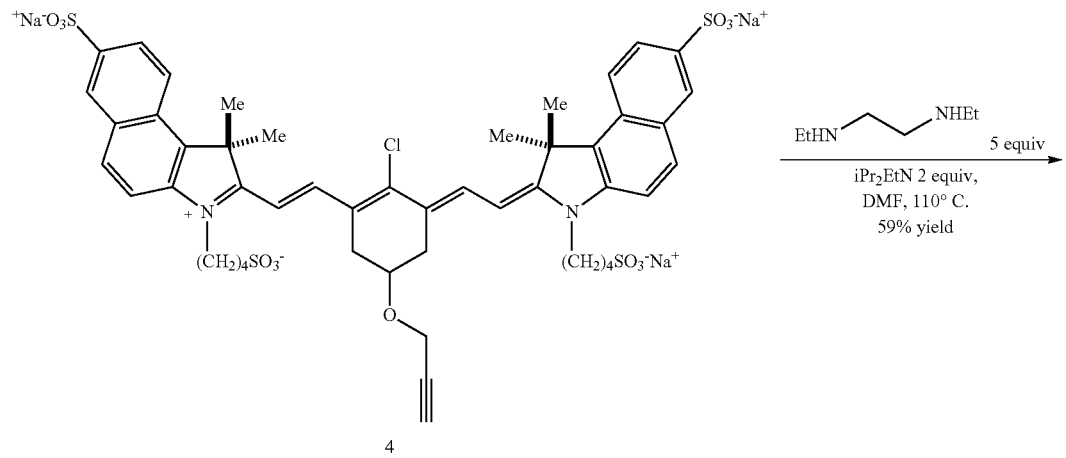

4

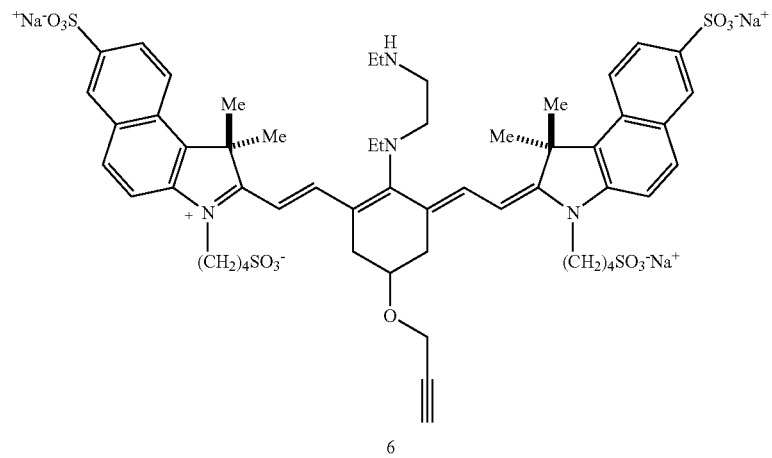

6

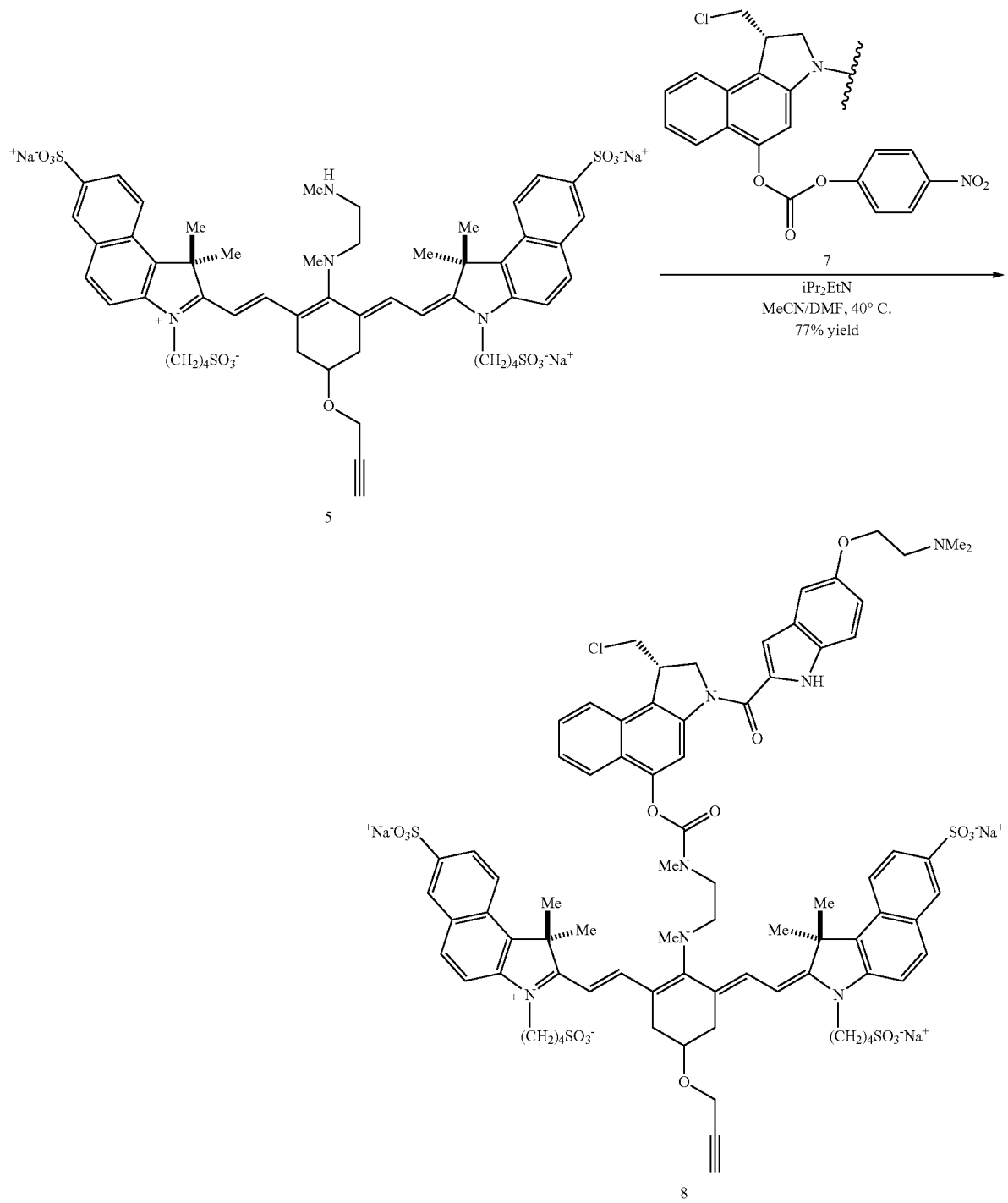

(8): To a 1-dram vial was added duocarmycin DM (1.0 mg, 0.0017 mmol) and MeCN (0.15 mL). Diisopropylethylamine (0.9 μL, 0.005 mmol) and a solution of 4-nitrophenyl-chloroformate (0.70 mg, 0.0035 mmol) in MeCN (0.1 mL) were added in succession. The clear, light yellow solution was stirred for 40 minutes at room temperature, after which time HPLC indicated 80% conversion to mixed carbonate 7. In a separate vessel diamine 5 (2.5 mg, 0.0022 mmol) was dissolved in DMF (0.4 mL) under argon, to which diisopropylethylamine (1.2 μL, 0.0070 mmol) was added. This DMF solution was combined with mixed carbonate 7, and the dark blue mixture was heated to 40° C. for 60 minutes. The reaction was cooled and diluted with $H_2O$ (7 mL), and the solution was directly purified by reversed-phase chromatography ($C_{18}$ gold column, 0→40% MeCN/water). The product-containing fractions were lyophilized to afford 8 (2.2 mg, 77% yield) as fluffy blue solid. MS (ESI) calculated for $C_{80}H_{86}ClN_7O_{17}S_4$ $(M+H)^{2-}$ 790.2, observed 790.3.

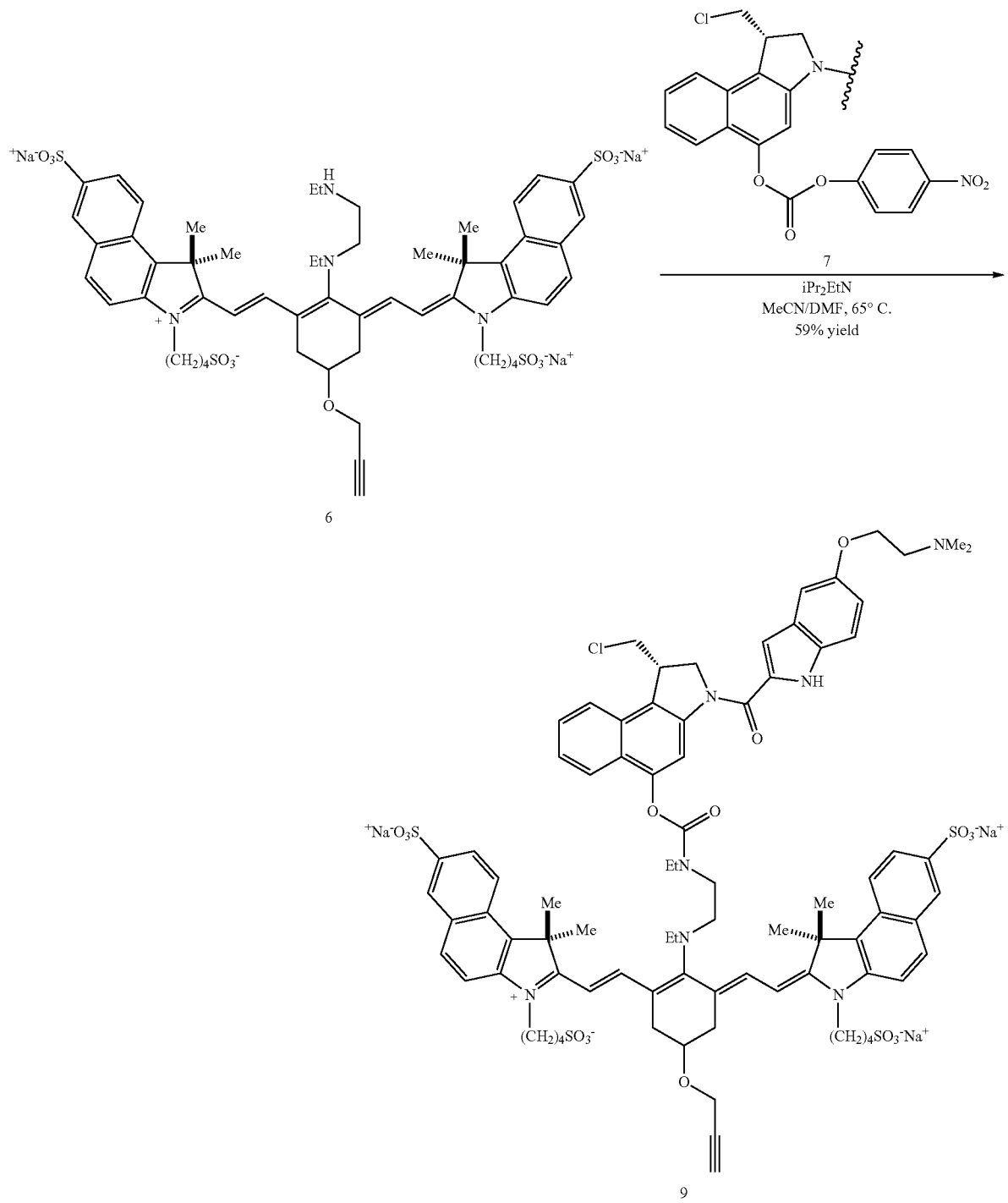

(9): To a 1-dram vial was added duocarmycin DM (4.9 mg, 0.0085 mmol) and MeCN (0.2 mL). Diisopropylethylamine (3.7 µL, 0.021 mmol) and a solution of 4-nitrophenylchloroformate (2.5 mg, 0.013 mmol) in MeCN (0.25 mL) were added in succession. The clear, light yellow solution was stirred for 40 minutes at room temperature, after which time HPLC indicated 80% conversion to mixed carbonate 7. In a separate vessel diamine 6 (6.7 mg, 0.0056 mmol) was dissolved in DMF (1.0 mL) under argon, to which diisopropylethylamine (8.0 µL, 0.046 mmol) was added. This DMF solution was combined with mixed carbonate 7, and the dark blue mixture was heated to 65° C. for 60 minutes. The reaction was cooled and diluted with $H_2O$ (7 mL), and the solution was directly purified by reversed-phase chromatography ($C_{18}$ gold column, 0→35% MeCN/water). The product-containing fractions were lyophilized to afford 9 (5.5 mg, 59% yield) as fluffy bluish-green solid. MS (ESI) calculated for $C_{82}H_{90}ClN_7O_{17}S_4$ $(M+H)^{2-}$ 804.3, observed 804.2.

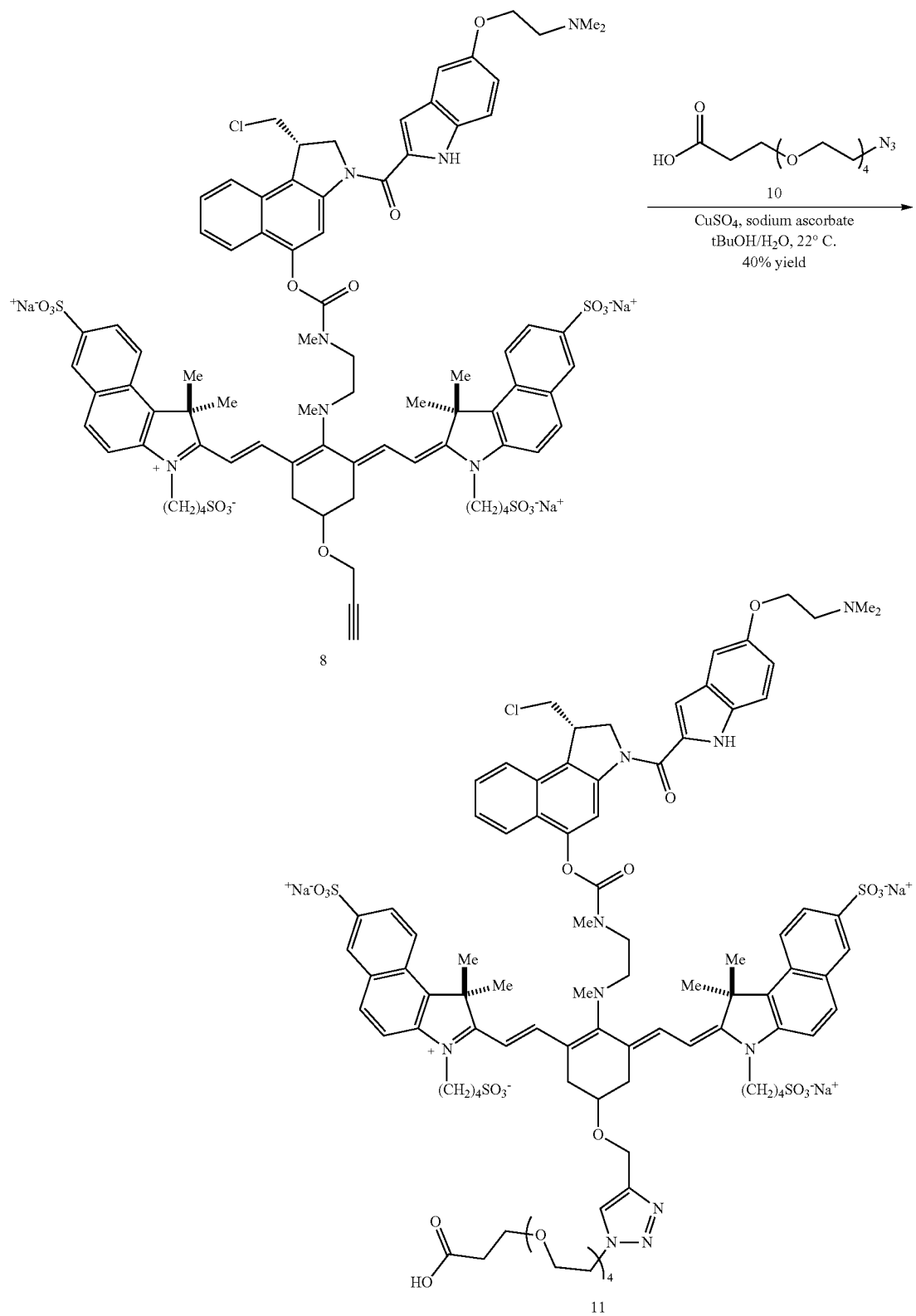

(11): To a 1-dram vial containing 8 (2.1 mg, 0.013 mmol) and 10 (0.5 mg, 0.002 mmol) was added a water/t-butanol mixture (1.0 mL, 3:1 v/v). The deep blue solution was sparged with argon for 1 minute with stirring. Cupric sulfate (0.03 mg, 0.0002 mmol) and sodium ascorbate (0.02 mg, 0.001 mmol) were added from 5 mg/mL aqueous stock solutions. The reaction was stirred for 30 minutes at 22° C., at which time LC/MS indicated consumption of 8. The reaction was diluted with water (4 mL) and the solution was directly purified by reversed-phase preparative HPLC (5-90% MeCN/0.1% aqueous $(NH_4)_2CO_3$). The product-containing fractions were lyophilized to afford 11 (1.0 mg, 40% yield) as fluffy blue solid. MS (ESI) calculated for $C_{91}H_{107}ClN_{10}O_{23}S_4$ $(M+H)^{2-}$ 935.8, observed 936.1.
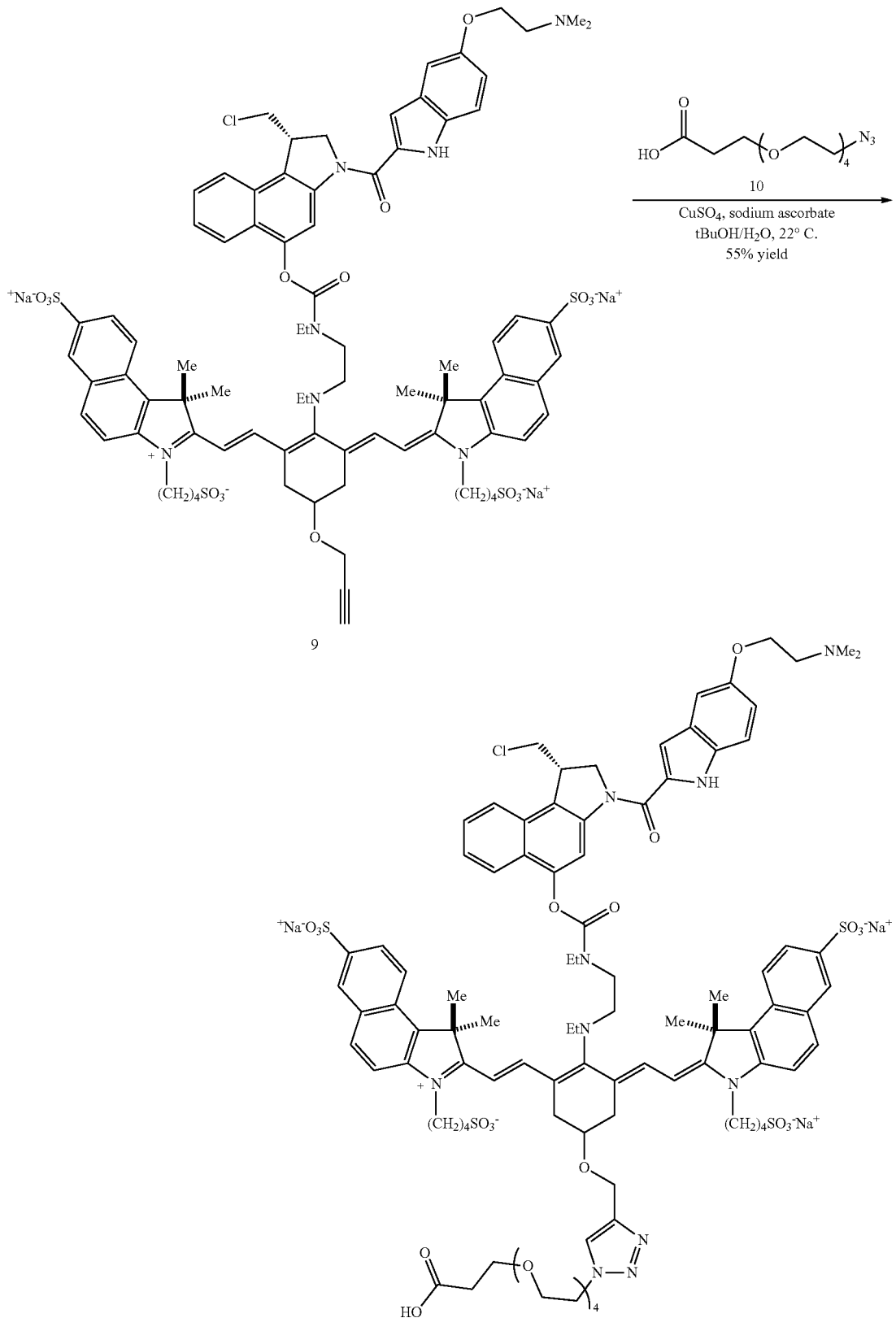

(12): To a 1-dram vial containing 9 (5.5 mg, 0.0033 mmol) and 10 (1.3 mg, 0.0043 mmol) was added a water/t-butanol mixture (1.2 mL, 1:1 v/v). The deep blue solution was sparged with argon for 1 minute with stirring. Cupric sulfate (0.08 mg, 0.0005 mmol) and sodium ascorbate (0.45 mg, 0.0023 mmol) were added from 5 mg/mL aqueous stock solutions. The reaction was stirred for 30 minutes at 22° C., at which time LC/MS indicated consumption of 9. The reaction was diluted with water (4 mL) and the solution was directly purified by reversed-phase preparative HPLC (5□90% MeCN/0.1% aqueous $(NH_4)_2CO_3$). The product-containing fractions were lyophilized to afford 12 (3.5 mg, 55% yield) as fluffy blue solid. MS (ESI) calculated for $C_{93}H_{111}ClN_{10}O_{23}S_4$ $(M+H)^{2-}$ 949.8, observed 950.5.

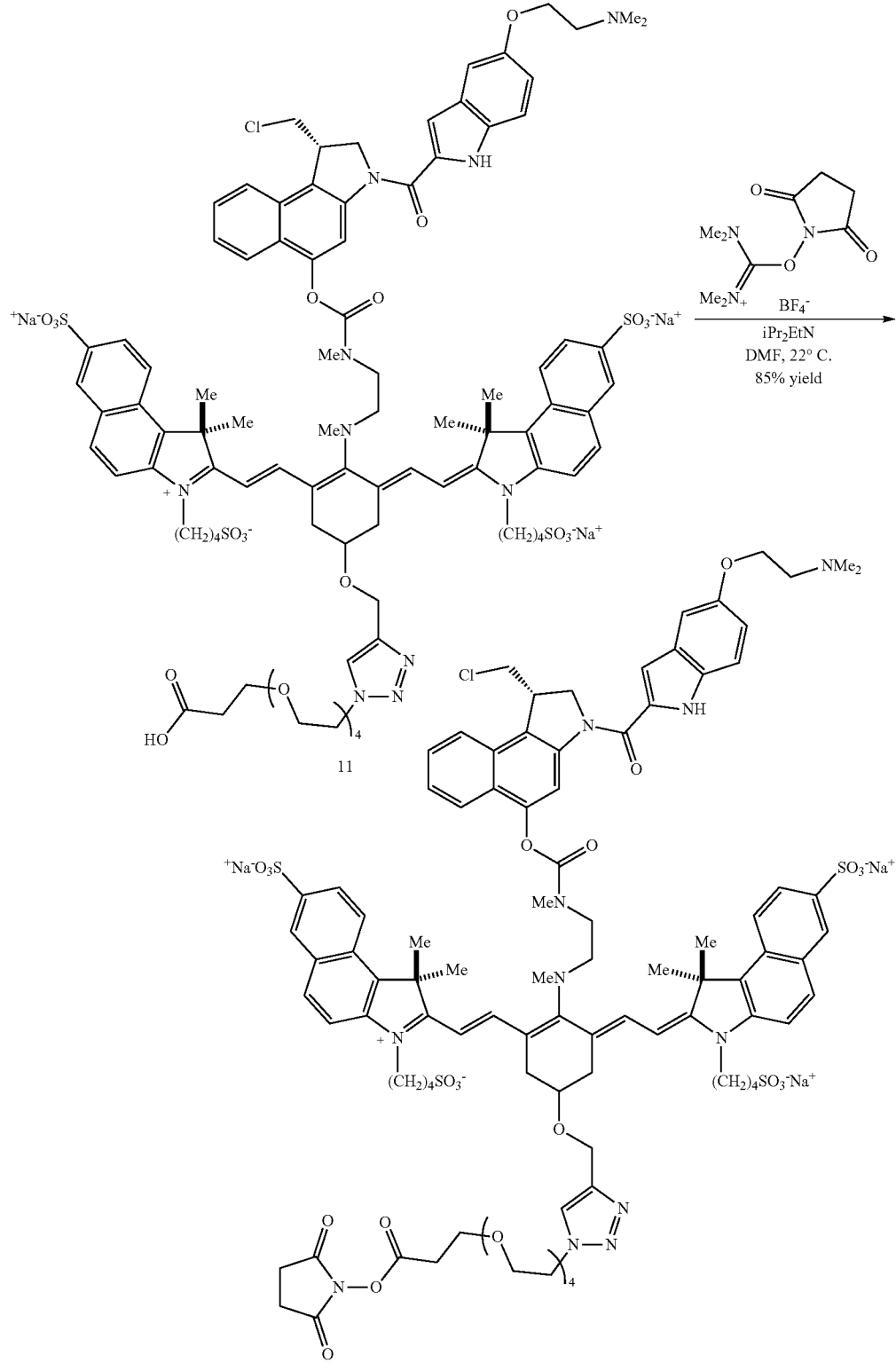

(13): To a 1 dram vial was added 11 (1.0 mg, 0.00046 mmol) and N,N,N',N'-tetramethyl-O—(N-succinimidyl)uranium tetrafluoroborate (0.2 mg, 0.0006 mmol). DMF (0.5 mL) was charged to the vial, followed by N,N-diisopropylethylamine (0.1 µL, 0.0006 mmol). The deep blue solution was stirred for 30 min at 22° C., at which time LC/MS indicated consumption of 11. The reaction was precipitated into ethyl acetate (1.0 mL). The fine suspension was centrifuged, the supernatant decanted, and the pellet resuspended in diethyl ether (0.5 mL). The procedure was repeated twice with diethyl ether, and the pellet was placed under vacuum (<0.1 Torr) for 1 h to afford 13 (0.9 mg, 85% yield) as a dark blue solid. MS (ESI) calculated for $C_{95}H_{110}ClN_{11}O_{25}S_4$ $(M+H)^{2-}$ 984.3, observed 984.4.

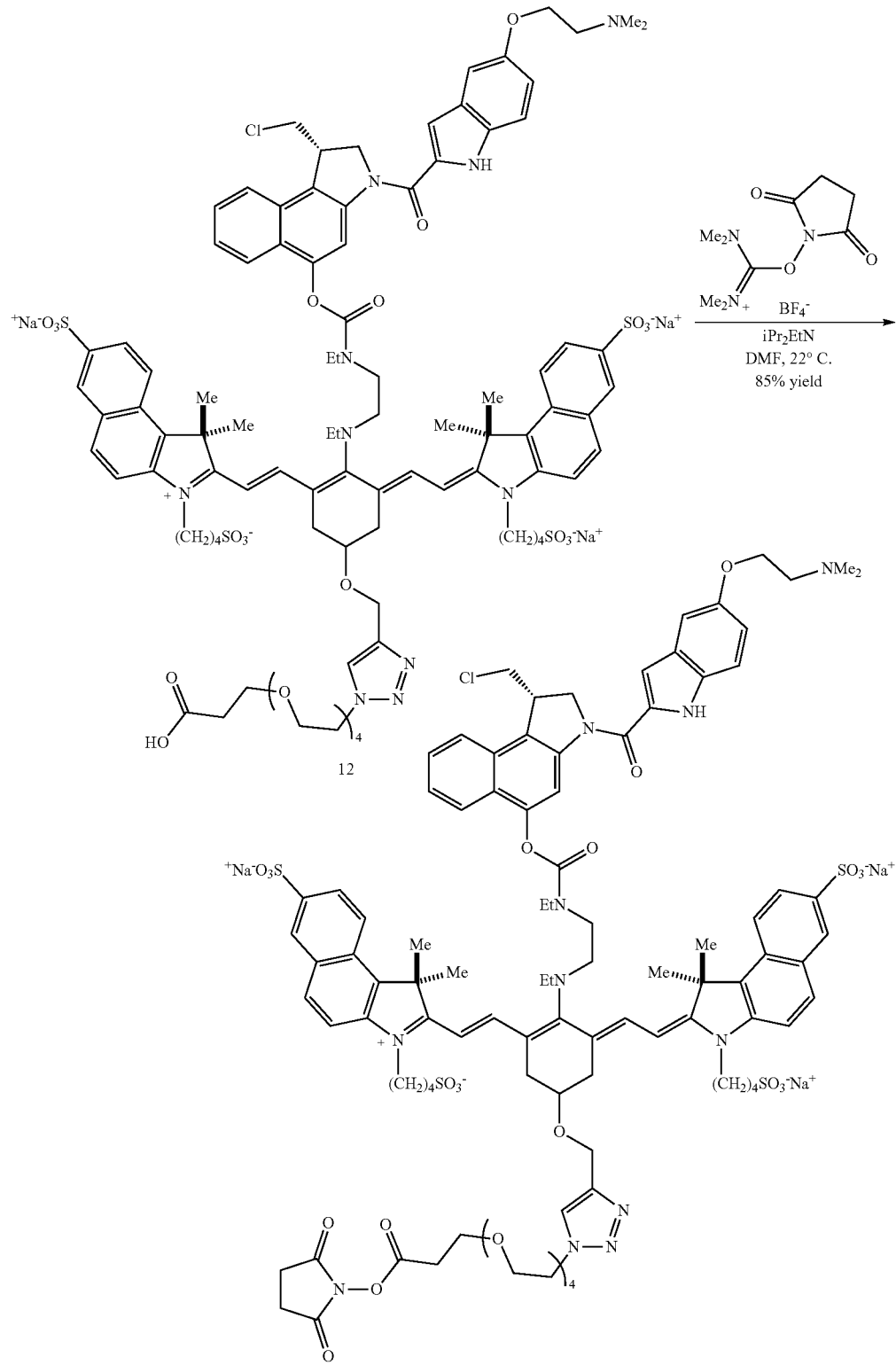

(14): To a 1 dram vial was added 12 (2.0 mg, 0.0010 mmol) and N,N,N',N'-tetramethyl-O—(N-succinimidyl)uranium tetrafluoroborate (0.6 mg, 0.002 mmol). DMF (0.5 mL) was charged to the vial, followed by N,N-diisopropylethylamine (0.3 □L, 0.002 mmol). The deep blue solution was stirred for 30 min at 22° C., at which time LC/MS indicated consumption of 12. The reaction was precipitated into diethyl ether (1.0 mL). The fine suspension was centrifuged, the supernatant decanted, and the pellet resuspended in ethyl acetate (0.5 mL). The procedure was then repeated twice with diethyl ether, and the pellet was placed under vacuum (<0.1 Torr) for 1 h to afford 14 (1.7 mg, 82% yield) as a dark blue solid. MS (ESI) calculated for $C_{97}H_{114}ClN_{11}O_{25}S_4$ $(M+H)^{2-}$ 998.3, observed 998.4.

Example 2

Conjugation to Panitumumab and Characterization

Compounds 12 and 14 were combined with panitumumab in 1 M PBS, pH 8.5, at 22° C. for 1 hour to produce CY(Me)-Pan-DuoDM and CY(Et)-Pan-DuoDM conjugates, respectively (FIGS. 5 and 6). The conjugates were purified by gel chromatography on a PD10 Sephadex G25 column, and dialysis in 50 mM PBS at 4° C. for 16 hours with one exchange. Degrees of labeling (DOL; i.e., number of CY-Drug conjugates per antibody) from 1-4 were obtained.

Figure 8:
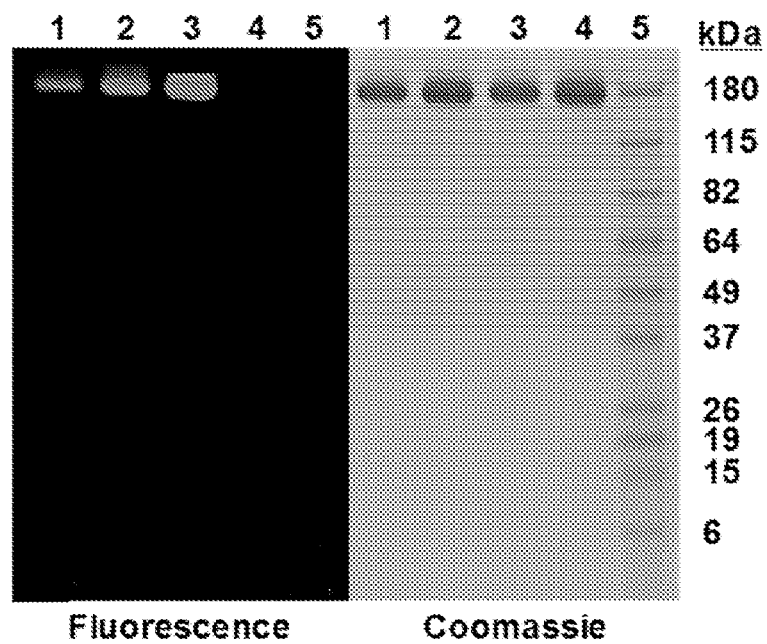
FIG. 8 shows SDS-PAGE analysis of the conjugates of FIGS. 5 and 6.

Sodium dodecyl sulfate-polyacrylamide gel electrophoresis (SDS-PAGE) was conducted to assess the purity of the antibody conjugates. NuPAGE 4-12% Bis-Tris gels (ThermoFisher Scientific) were loaded with 5 µg of CY(Me)-Pan-DuoDM (DOL 3), CY(Et)-Pan-DuoDM (DOL 3 and 4), and Pan (in a 1:4 (v/v) solution of NuPAGE LDS sample buffer and 50 mM pH 7.4 PBS) and run under non-reducing conditions in 1×MES SDS running buffer at 200 V for 35 min. BenchMark Pre-Stained Protein Standard (ThermoFisher Scientific) was used for molecular weight comparison. Fluorescence images were obtained using an ImageQuant LAS 4000 (GE Healthcare) with red epi light (630 nm) excitation and a 670 nm longpass emission filter. Exposure time was 300 s. Gels were stained with SimplyBlue SafeStain (ThermoFisher Scientific) for 1 h and imaged with white transillumination (1 s exposure time). FIG. 8 shows the SDS-PAGE analysis of DOL 3 CY(Et)-Pan-DuoDM (1), DOL 4 CY(Et)-Pan-DuoDM (2), DOL 3 CY(Me)-Pan-DuoDM (3), Pan (4), and molecular weight standards (5).

Figure 9:
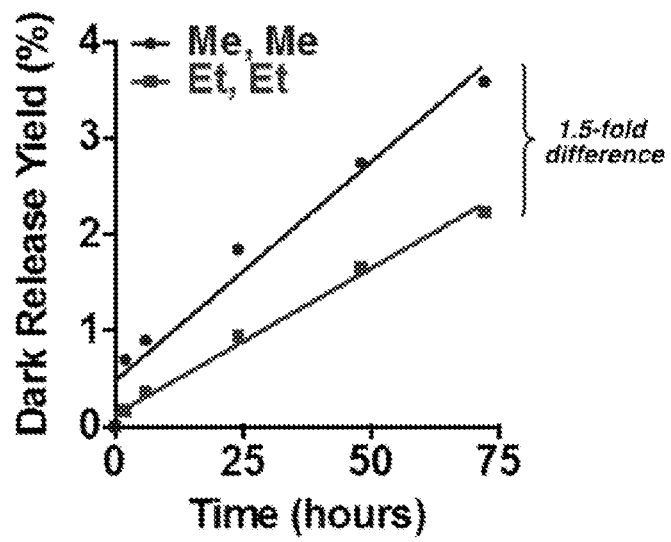
FIG. 9 is a graph showing stability of CY(Me)-Pan-DuoDM and CY(Et)-Pan-DuoDM in the dark.

The CY(Me)-Pan-DuoDM and CY(Et)-Pan-DuoDM conjugates were evaluated for stability. Although both conjugates were stable, CY(Et)-Pan-DuoDM released 1.5-fold less drug in the dark over a period of 75 hours (FIG. 9).

Figure 10:
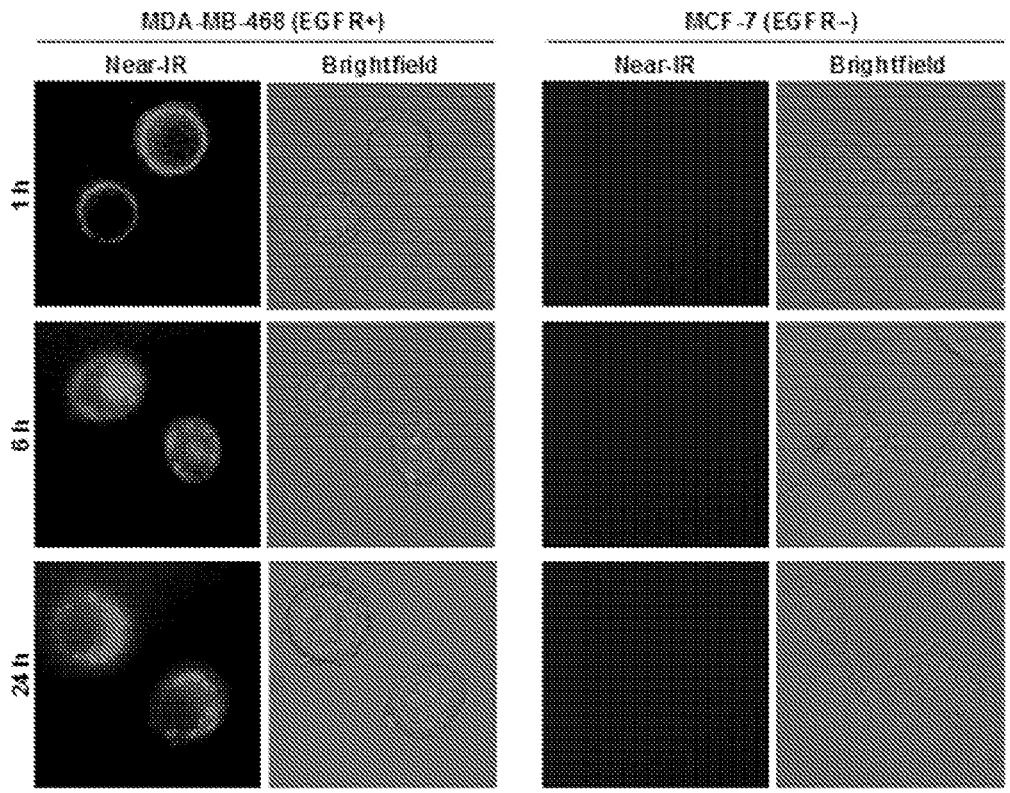
FIG. 10 shows fluorescence and brightfield microscopy images of live MDA-MB-468 and MCF-7 cells treated with CY(Et)-Pan-DuoDM (DOL4) for 1 h on ice, 6 h at 37° C., and 24 h at 37° C. Near-IR fluorescence was imaged using a Cy7 channel.

MDA-MB-468 or MCF-7 cells ($2 \times 10^4$ cells/dish) were plated on #1.5 cover glass-bottomed dishes (Cellvis) and allowed to adhere overnight. Cells were incubated with 1 µM CY(Et)-Pan-DuoDM (DOL 4) for 1 h on ice, the media replaced, and imaged. Alternatively, cells were incubated with conjugate for 1 h on ice, the media replaced, incubated for 6 h or 24 h at 37° C., and imaged. Fluorescence microscopy was performed using an Evos FL Auto Cell Imaging System (ThermoFisher Scientific) at 100× magnification using a plan-fluorite oil immersion objective. Near-IR fluorescence was obtained with a Cy7 LED light cube ($\lambda_{ex}$ 710±20 nm, $\lambda_{em}$ 775±23 nm). Image processing was conducted with ImageJ. FIG. 10 shows that the conjugates bound to MDA-MB-468 (EGFR+) cells, but did not bind to MCF-7 (EGFR−) cells.

Example 3

Cell Photolysis and Cytotoxicity

MDA-MB-468 (EGFR overexpression) and MCF-7 (normal EGFR expression) human breast cancer cell lines were obtained from the NCI DTP, DCTD Tumor Repository. MDA-MB-468 was cultured in RPMI supplemented with 2 mM L-glutamine, 11 mM D-glucose, 24 mM sodium bicarbonate, 10% heat-inactivated fetal bovine serum, 100 units/mL penicillin, 100 µg/mL streptomycin, and 0.25 µg/mL amphotericin B. MCF-7 was cultured in DMEM supplemented with 4 mM L-glutamine, 25 mM D-glucose, 44 mM sodium bicarbonate, 10% heat-inactivated fetal bovine serum, 100 units/mL penicillin, 100 µg/mL streptomycin, and 0.25 µg/mL amphotericin B. Both cell lines were grown at 37° C. in an atmosphere of 20% $O_2$ and 5% $CO_2$. Stock cultures were maintained in continuously exponential growth by weekly passage of the appropriate number of cells following trypsinization with 0.25% Trypsin-EDTA (0.9 mM) in PBS.

CY(Me)-Pan-DuoDM was determined to have a maximum absorbance at 690 nm. Replacement of the methyl substituents with ethyl groups produced a red shift of about 50 nm, and CY(Et)-Pan-DuoDM was determined to have a maximum absorbance at 740 nm.

MDA-MB-468 or MCF-7 cells were seeded into 96-well plates ($5 \times 10^4$ cells/well) and allowed to adhere overnight. Initial seeding densities were such to ensure cells remained in exponential growth for the duration of the assay. For the continuous dose assay, media was replaced with that containing CY(Me)-Pan-DuoDM (DOL 3), CY(Et)-Pan-DuoDM (DOL 3), DuoDM, or DMSO. Cells were exposed to the indicated dosage of irradiation from a 690 or 740 nm LED (20 mW/cm$^2$) or kept dark. Irradiation times may be calculated according to the following formula:

$$\text{Irradiation time(s)} = \frac{\text{Light Dose(J/cm}^2\text{)}}{\text{Light Power(W/cm}^2\text{)}}$$

For the pre-incubation assay, media was replaced with that containing test compounds, incubated for 24 h at 37° C. in the dark, media replaced with fresh, inhibitor free media, and irradiated as above. Following a 72 h incubation period at 37° C., 20 µL of MTT (3-(4,5-dimethylthiazol-2-yl)-2,5-diphenyltetrazolium bromide) from a 5 mg/mL stock in PBS was added to each well and incubated for 4 h at 37° C. Media was removed, 100 µL of DMSO added to each well to solubilize MTT formazan, and absorbance at 550 nm was recorded using a microplate reader. Drug effects were expressed as % cell viability relative to the DMSO (no inhibitor) control. Half maximal inhibitory concentrations ($IC_{50}$s) were obtained from sigmoidal curve fits of % viability vs. concentration data using GraphPad Prism 6. All experiments were conducted in quadruplicate, with error bars representing the standard deviation.

Table 2 shows near-IR light-dependent growth inhibition of EGFR-positive and EGFR-negative cells in the presence of CY(Me)-Pan-DuoDM or CY(Et)-Pan-DuoDM.

TABLE 2

| Species | Cell Line | Irradiation Condition[a] | $IC_{50}$[b] | Fold Δ[c] |
|---|---|---|---|---|
| CY(Me)-Pan-DuoDM | MDA-MB-468 (EGFR+) | +hv | 62.0 ± 1.2 pM | 203 |
| | | −hv | 12.6 ± 0.7 nM | |
| | MCF-7 (EGFR−) | +hv | 48.8 ± 1.6 nM | 2 |
| | | −hv | 90.0 ± 2.2 nM | |

TABLE 2-continued

| Species | Cell Line | Irradiation Condition[a] | IC$_{50}$[b] | Fold Δ[c] |
|---|---|---|---|---|
| CY(Et)-Pan-DuoDM | MDA-MB-468 (EGFR+) | +hv<br>−hv | 57.1 ± 0.9 pM<br>16.7 ± 1.9 nM | 292 |
|  | MCF-7 (EGFR−) | +hv<br>−hv | 65.4 ± 1.0 nM<br>>100 nM | <2 |
| DuoDM | MDA-MB-468 (EGFR+) | ±hv | 7.0 ± 0.6 pM | — |
|  | MCF-7 (EGFR−) | ±hv | 13.3 ± 1.1 pM |  |

Figure 11A:
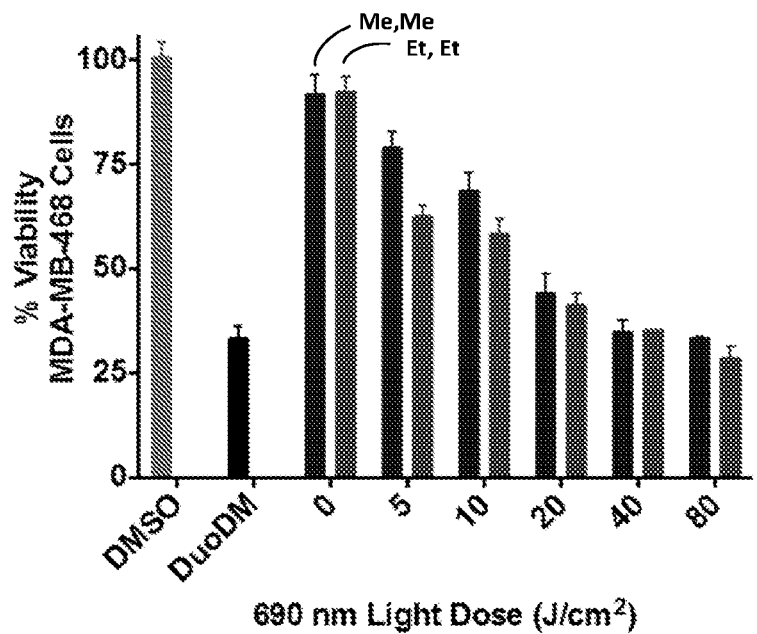
FIGS. 11A and 11B show the effects of light dose and wavelength on the near-IR light-dependent growth inhibition of MDA-MB-468 cells in the continuous presence of CY(Me)-Pan-DuoDM (first bar at each light dose) or CY(Et)-Pan-DuoDM (second bar at each light dose). The degree of labeling for each conjugate was four.
Figure 11B:
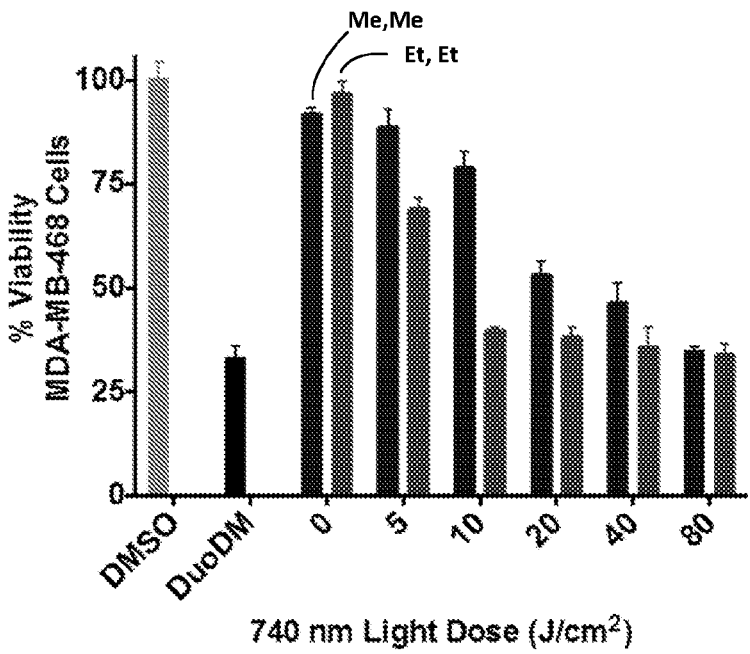

[a]Media was exchanged prior to photolysis;
[b]30 J/cm$^2$, 690 nm;
[c]average IC$_{50}$ value ± standard deviation (n = 4);
[d]Ratio −hv/+hv FIGS. 11A (690 nm) and 11B (740 nm) show the effects of light dose and wavelength on the near-IR light-dependent growth inhibition of MDA-MB-468 cells in the continuous presence (i.e. media not exchanged during the assay) of CY(Me)-Pan-DuoDM (first bar at each light dose) or CY(Et)-Pan-DuoDM (second bar at each light dose). Both conjugates had a DOL of 3. Light dosages required to achieve 50% growth inhibition (hv$_{1/2}$ (light dose required to achieve 50% cell viability)) were calculated by nonlinear curve fitting. Error bars represent the standard deviation (n=4). For CY(Me)-Pan-DuoDM, hv$_{1/2}$ was 10.5±2.2 J/cm$^2$ at 690 nm, and 17.0±3.5 J/cm$^2$ at 740 nm. For CY(Et)-Pan-DuoDM, hv$_{1/2}$ was 8.0±2.5 J/cm$^2$ at 690 nm, and 4.4±2.6 J/cm$^2$ at 740 nm.

Example 4

Biodistribution and Photolysis In Vivo

All in vivo procedures were conducted in compliance with the Guide for the Care and Use of Laboratory Animal Resources (1996), US National Research Council, and approved by the National Cancer Institute/NIH Animal Care and Use Committee. Six- to 8-week-old female homozygote athymic nude mice were purchased from Charles River Laboratories International, Inc. (NCI-Frederick). During treatment, mice were anesthetized with isoflurane. MDA-MB-468 cells (6×10$^6$) were injected subcutaneously in the right dorsum of each mouse. Experiments were performed at 8-9 days after cell injection. Tumors reaching approximately 5-7 mm were selected for the study.

Biodistribution: Serial ventral and dorsal fluorescence images of MDA-MB-468 tumor-bearing mice were obtained before and 0, 1, 3, 6, 9, 24, 48, 72, 96, 120, 144, and 168 h after i.v. injection of 100 μg of CY(Et)-Pan-DuoDM (DOL 4) via the tail vein. Images were collected with a Pearl Imager (LI-COR Biosciences) using a 800 nm fluorescence channel Regions of interest (ROIs) were placed on the fluorescent images with a white light reference to measure fluorescence intensities of the tumor, the liver, and the left dorsum (i.e. background tissue on the opposite side of the target). Pearl Cam software (LI-COR Biosciences) was used to calculate the average fluorescence intensity within each ROI. Target-to-background ratio (TBR) was calculated using the following formula (n=5):

$$TBR = \frac{\text{mean target intensity} - \text{mean background intensity}}{\text{mean non-target intensity} - \text{mean background intensity}}$$

Figure 12A:
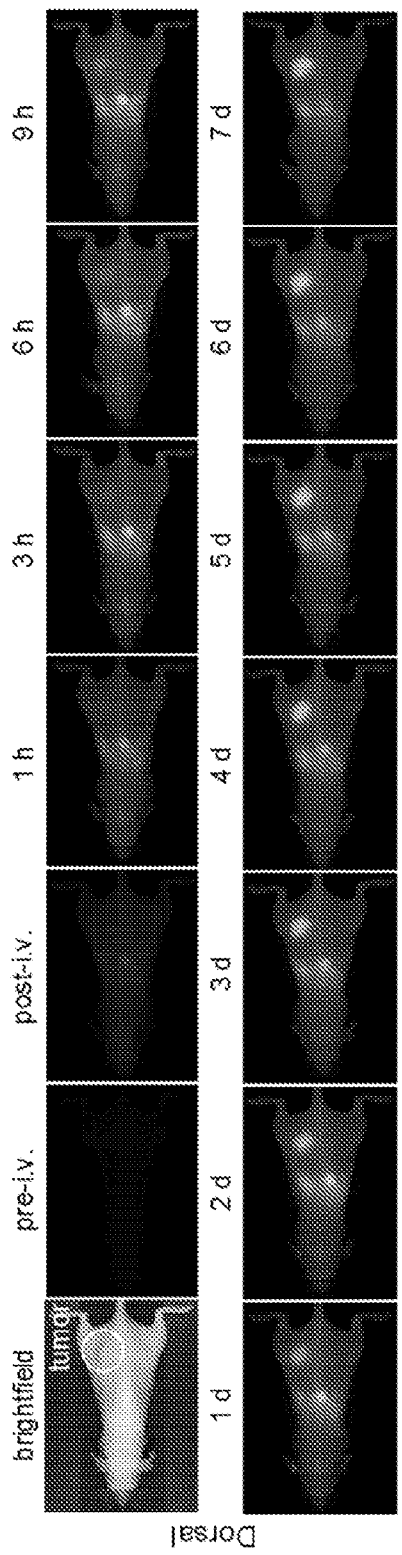
FIGS. 12A and 12B show biodistribution and tumor localization of CY(Et)-Pan-DuoDM (DOL4) in MDA-MB-468 tumor-bearing mice as a function of time. Serial fluorescence images were taken from the dorsal (12A) and ventral (12B) sides.
Figure 12B:
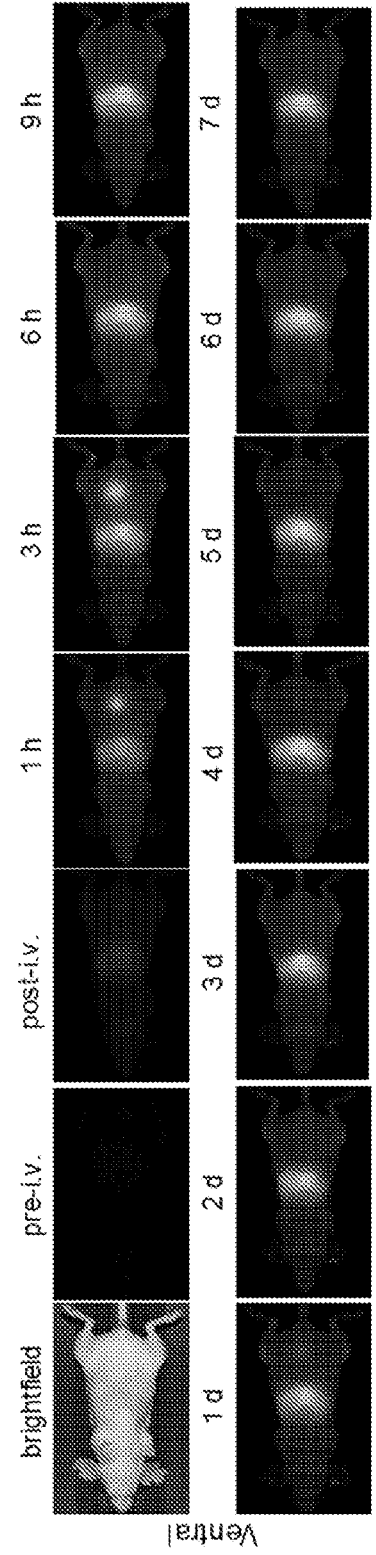
Figure 13A:
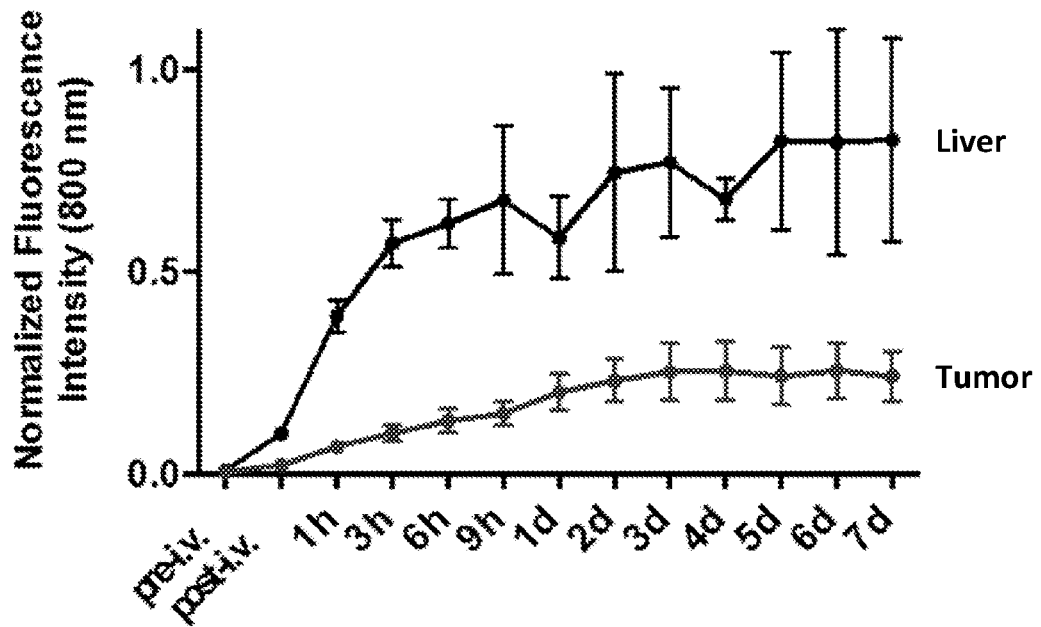
FIGS. 13A and 13B are graphs of normalized fluorescence intensity (13A) and target-to-background ratio (13B) of the tumor and liver of the mice in FIGS. 12A and 12B as a function of time post-injection. Error bars represent S.E.M. (n=5).
Figure 13B:
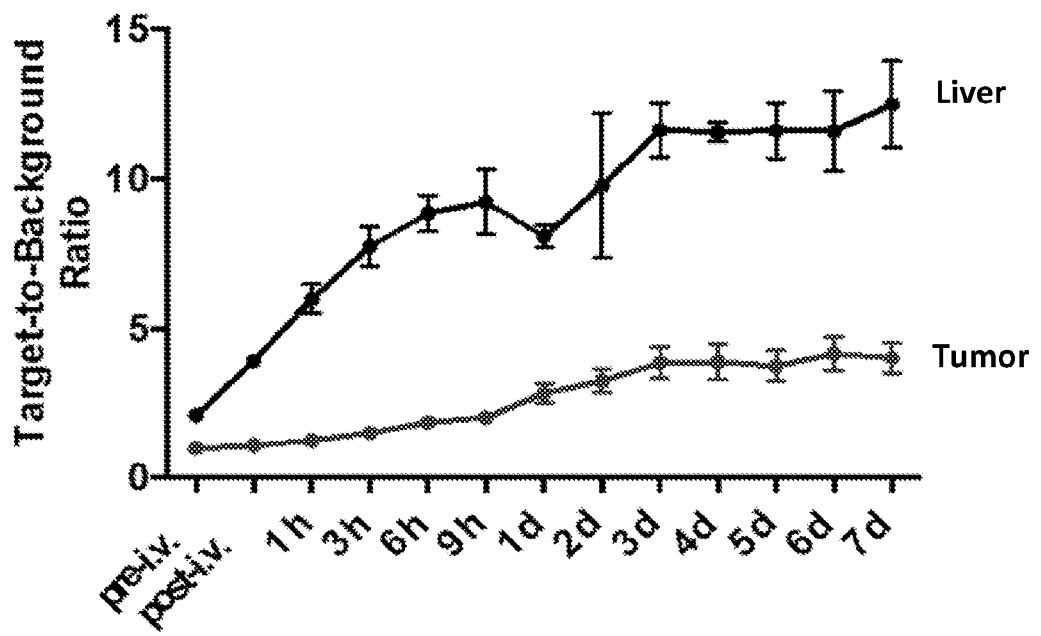

FIGS. 12A and 12B show the biodistribution and tumor localization of CY(Et)-Pan-DuoDM (DOL 4) as a function of time. Serial fluorescence images of MDA-MB-468 tumor-bearing mice were taken from the dorsal (12A) and ventral (13B) sides. n=5. FIGS. 13A and 13B are graphs of normalized fluorescence intensity (13A) and target-to-background ratio (13B) of the tumor and liver of the mice from FIGS. 12A and 12B as a function of time post-injection. Error bars represent S.E.M. (n=5). Additional studies (data not shown) demonstrated that the fluorescence was proportional to the degree of labeling, i.e., the number of CY(Et)-DuoDM moieties conjugated to a single antibody, and that the differences persisted for at least seven days post injection.

Figures 14, 15:
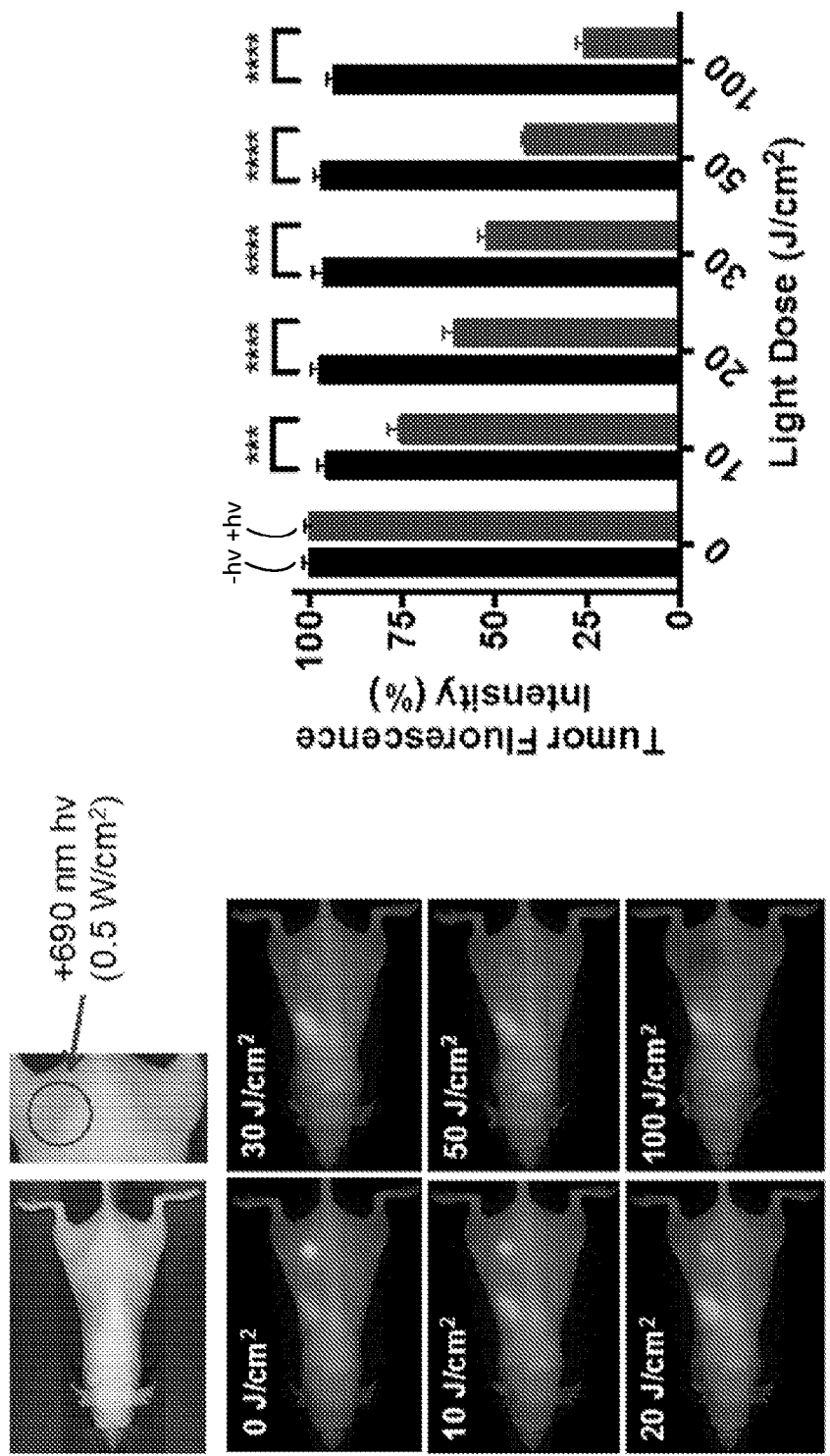
FIG. 14 shows serial fluorescence images of MDA-MB-468 tumor-bearing mice, pre- and post-irradiation of the tumor with increasing doses of 690 nm light at four days post-injection of CY(Et)-PanDuoDM (DOL4).
FIG. 15 is a graph showing average tumor fluorescence intensity as a function of near-IR light dose, relative to the 0 J dose point. The first bar at each time point is the fluorescence without irradiation. The second bar at each time point is the fluorescence following the indicated light dose.

In Vivo Near-IR Irradiation: CY(Et)-Pan-DuoDM (DOL 4, 100 μg) was administered i.v. via the tail vein to MDA-MB-468 tumor-bearing mice (n=5 mice per condition). Four days post-injection, the tumor was exposed to 0, 10, 20 30, 50, and 100 J/cm$^2$ doses of 690 nm light (0.5 W/cm$^2$) using a laser system (BWFS-690-8-600-0.37; B&W Tek, Inc.). A second cohort was maintained without irradiation Immediately after exposing tumors to the indicated dose, serial dorsal fluorescence images of irradiated and corresponding unirradiated mice were obtained with a Pearl Imager using a 800 nm fluorescence channel Regions of interest (ROIs) were placed on the tumor and average fluorescence intensity determined using Pearl Cam software, with the intensity of the 0 J dose point set to 100%. FIGS. 14 and 15 show fluorescence signal of MDA-MB-468 tumors as a function of near-IR irradiation. FIG. 14 is serial fluorescence images of MDA-MB-468 tumor-bearing mice, pre- and post-irradiation of the tumor with increasing doses of 690 nm light at four days post-injection of CY(Et)-PanDuoDM (DOL 4). Images from the irradiated cohort are shown; the unirradiated cohort is similar to the 0 J/cm$^2$ dose point; n=5. FIG. 15 is a graph showing average tumor fluorescence intensity as a function of near-IR light dose, relative to the 0 J/cm$^2$ dose point. Error bars represent S.E.M. (n=5). *p<0.001, **p<0.0001. The first bar at each time point is the fluorescence without irradiation. The second bar at each time point is the fluorescence following the indicated light dose. FIGS. 14 and 15 clearly demonstrate tumor-specific localization of the conjugate and loss of fluorescence upon targeted irradiation.

Figure 16:
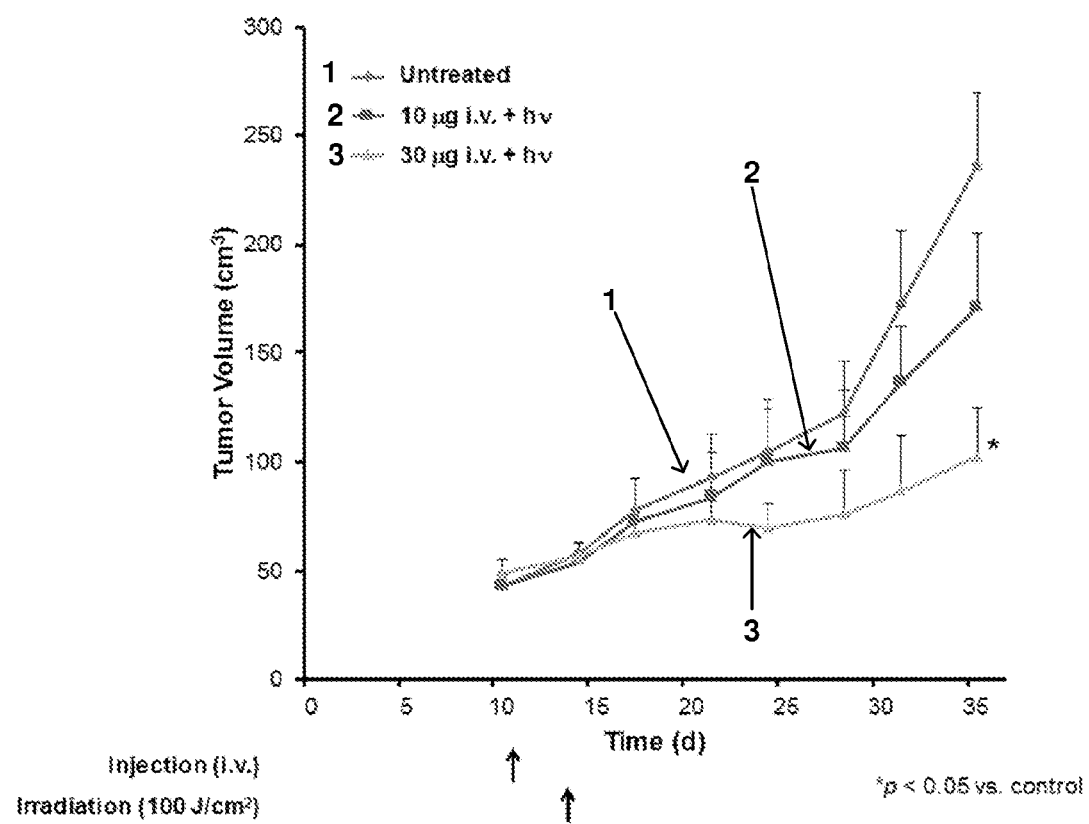
FIG. 16 is a graph showing in vivo effects of the CY(Et)-PanDuoDM (DOL4) conjugate on tumor growth.

FIG. 16 is a graph showing in vivo effects of the conjugate on tumor growth. MDA-MB-468 cells (6×10$^6$) were injected subcutaneously on right dorsum of the mice. Tumor bearing mice were randomized into 3 groups (n=4-5) for the following treatments: (1) no treatment (control, ♦); (2, ■) 10 μg of CY(Et)-PanDuoDM DOL4 i.v., NIR light was administered at 100 J/cm$^2$ on day 4; (3, ▲) 30 μg of CY(Et)-PanDuoDM DOL4 i.v., NIR light was administered at 100 J/cm$^2$ on day 4. Tumor growth was significantly inhibited in the 30 μg i.v. irradiated group relative to the control group.

Example 5

Treatment of Tumors with the Disclosed Conjugates

A subject having a tumor is identified and selected for treatment. The subject may be selected based on a clinical presentation and/or by performing tests to demonstrate presence of a tumor.

The subject is treated by administering a conjugate according to Formula I or Formula II, a pharmaceutically acceptable salt thereof, or a pharmaceutical composition thereof at a dose determined by a clinician to be therapeutically effective. The conjugate is administered by any suitable means, such as parenteral, intravenous, or subcutaneous injection. In some instances, the conjugate is injected directly into the tumor. In some examples, the location of the conjugate is monitored by exposure to light having a wavelength suitable for inducing fluorescence of the cyanine fluorophore, thereby exciting the cyanine fluorophore, and detecting fluorescence of the conjugate. Monitoring may be performed after a period of time sufficient to allow binding of the conjugate to the tumor.

The administered conjugate subsequently is irradiated by targeted application of an effective quantity of light having a wavelength in the near-infrared range and a selected intensity to a targeted portion of the subject, thereby releasing the drug from at least some molecules of the conjugate. Advantageously, the targeted portion of the subject is proximate the tumor. Irradiation may be performed after a period of time sufficient to allow binding of the conjugate to the tumor. For example, irradiation may be performed several hours to several days after administration of the conjugate, such as from 1-7 days after administration of the conjugate. In some instances, drug release is assessed by monitoring a decrease in fluorescence emission of the conjugate in vivo.

In some instances, at least a portion of the tumor is surgically excised prior to targeted application of near-infrared light with subsequent release of the drug from at least some molecules of the conjugate. Fluorescence-guided surgery is used to determine the location and extent of tissue excision.

In some cases, the subject is suspected of having a tumor and presence of a tumor is confirmed by administering the conjugate to the subject and monitoring the conjugate's fluorescence at a suspected tumor site. Accumulation of the conjugate and fluorescence at the suspected tumor site diagnoses presence of a tumor. The administered conjugate subsequently is irradiated as described above to release the drug from at least some molecules of the conjugate.

A therapeutically effective amount of a second agent may be co-administered with the conjugate or salt thereof. The conjugate (or salt thereof) and the second agent may be administered either separately or together in a single composition. The second agent may be administered by the same route or a different route. If administered concurrently, the conjugate (or salt thereof) and the second agent may be combined in a single pharmaceutical composition or may be administered concurrently as two pharmaceutical compositions. The second agent may be, for example, an anti-tumor agent or an angiogenesis inhibitor.

Representative embodiments are described in the following numbered clauses.

1. A conjugate having a chemical structure according to Formula I, or a pharmaceutically acceptable salt thereof:

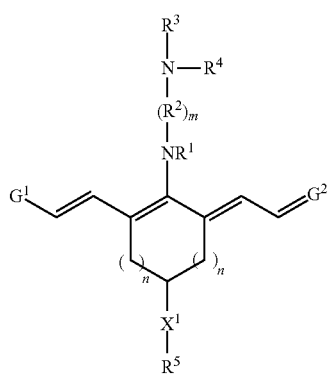

(I)

wherein m is 1, 2, 3, 4, or 5; each n independently is 1, 2, or 3; $R^1$ and $R^4$ independently are alkyl, haloalkyl, cycloalkyl, alkoxy, —ROH, —RC(O)OH, —C(O)—R, or —C(O)—O—R, wherein R is alkyl; $R^2$ is $C(R^c)_2$ wherein each $R^c$ independently is H, halo, alkyl, or aryl, or $(R^2)_m$ collectively is phenyl; $R^3$ is -$L_1$-C(O)—$X^2$-drug, where $L_1$ is a linker moiety or is absent and $X^2$ is O, N(H), or N($CH_3$); $R^5$ is —$(CH_2)_x$-$L_2$-$R^a$, where x is an integer$\geq$1, $L_2$ is a linker moiety or is absent, and $R^a$ is

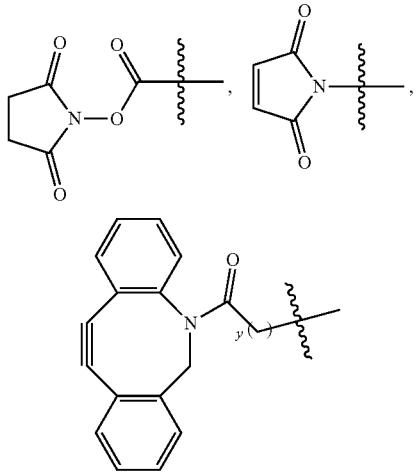

where y is an integer$\geq$1, —C(O)N(H)$R^b$, —N(H)C(O)$R^b$, —N(H)$R^b$, or —S$R^b$ where $R^b$ is a targeting agent,

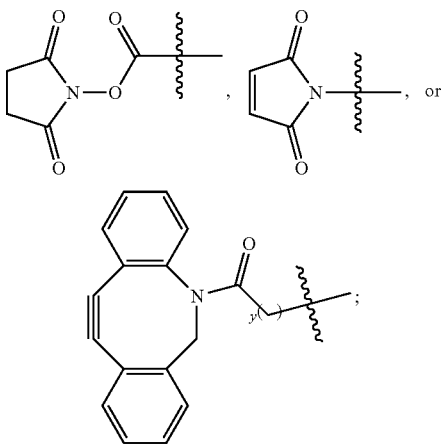

$X^1$ is O, N, or $CH_2$; $G^1$ is

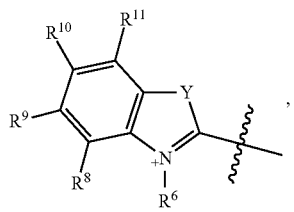

-continued

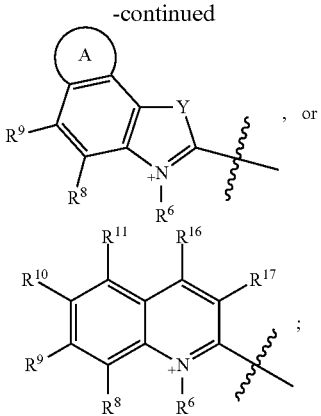, or

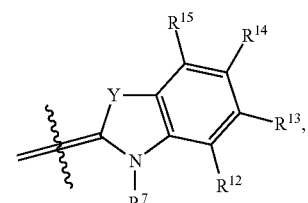;

G² is

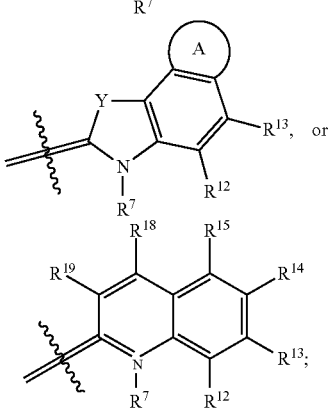,

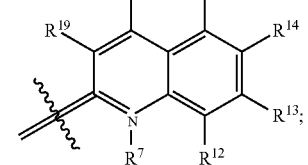, or

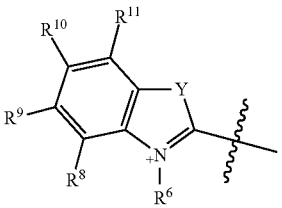;

R⁶ and R⁷ independently are H, alkyl, alkoxy, alkyl sulfonate, or substituted aminoalkyl; R⁸-R¹⁹ independently are H, alkyl, amino, alkoxy, or alkyl sulfonate; each Y independently is $C(R^d)_2$, S, O, Se, or $N(R^d)$ wherein each $R^d$ independently is H or alkyl; and each ring A independently is a 6-membered fused aliphatic, heteroaliphatic, aryl, or heteroaryl ring.

2. The conjugate according to clause 1, wherein R¹ and R⁴ independently are $C_1$-$C_4$ alkyl, —ROH, —RCOOH, or —RCF₃, where R is $C_1$-$C_4$ alkyl.

3. The conjugate according to clause 1, wherein R¹ and R⁴ independently are methyl, ethyl, n-propyl, i-propyl, t-butyl, or —(CH₂)₂OH.

4. The conjugate according to clause 1, wherein R¹ and R⁴ are ethyl.

5. The conjugate according to any one of clauses 1-4, wherein ring A is a fused phenyl ring substituted with optionally substituted sulfonate.

6. The conjugate according to any one of clauses 1-5, wherein: G¹ is

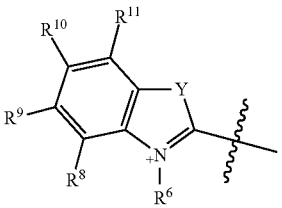

and G² is

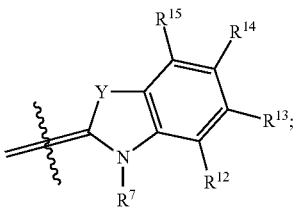

or G¹ is

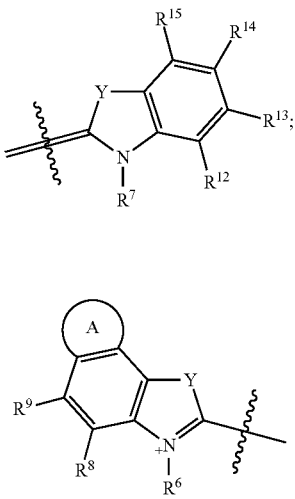

and G² is

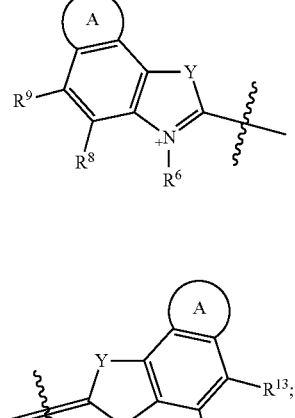

or G¹ is

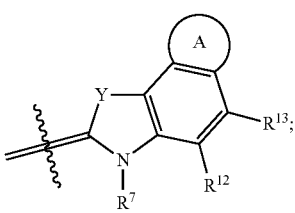

and G² is

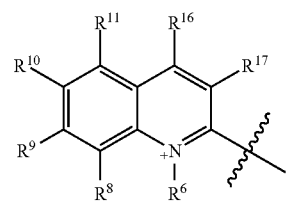, wherein each Y is the same, R⁶ and R⁷ are identical, and R⁸-R¹¹ and R¹⁶-R¹⁷ are identical to R¹²-R¹⁵ and R¹⁸-R¹⁹, respectively.

7. The conjugate according to any one of clauses 1-6, wherein each Y is C(CH₃)₂.

8. The conjugate according to any one of clauses 1-7, wherein $R^6$ and $R^7$ are —(CH$_2$)$_p$SO$_3$⁻ or —(CH$_2$)$_p$N(CH$_3$)$_3$⁺, where p is 1, 2, 3, 4, or 5.

9. The conjugate according to any one of clauses 1-8, wherein $R^8$-$R^{19}$ are H.

10. The conjugate according to any one of clauses 1-10, having a structure according to Formula II:

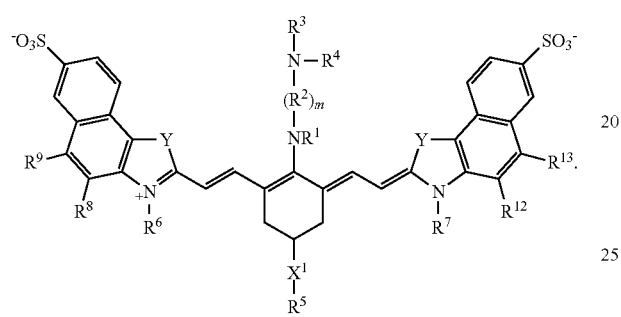

(II)

11. The conjugate according to any one of clauses 1-10, wherein $R^3$ is

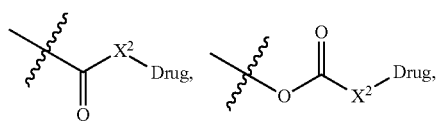

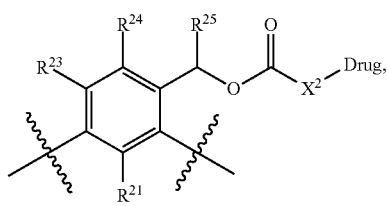

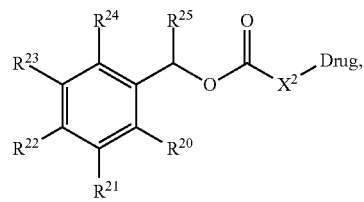

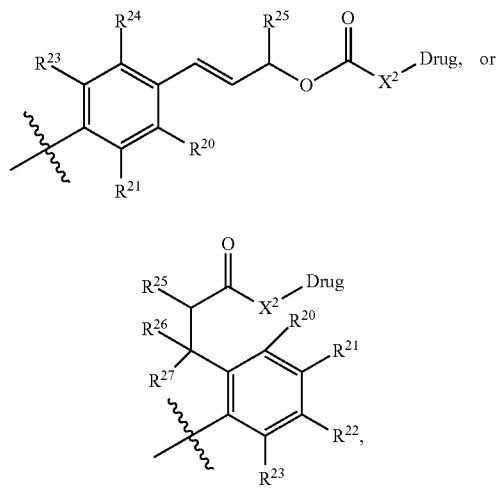

where $R^{20}$-$R^{27}$ independently are H, alkyl, —NO$_2$, —NR$^e$$_2$, —NR$^e$$_3$, alkoxy, or sulfonate, wherein each R$^e$ independently is H, halo, or alkyl.

12. The conjugate according to clause 11, wherein $R^{20}$-$R^{25}$ are H.

13. The conjugate according to any one of clauses 1-12, wherein $R^3$ is

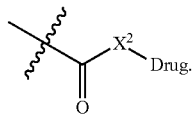

14. The conjugate according to any one of clauses 1-13, wherein —X²-Drug is

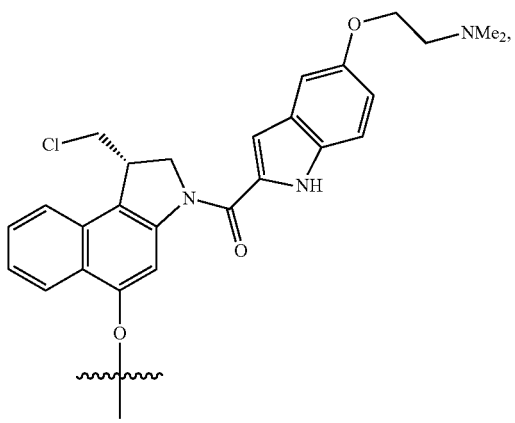

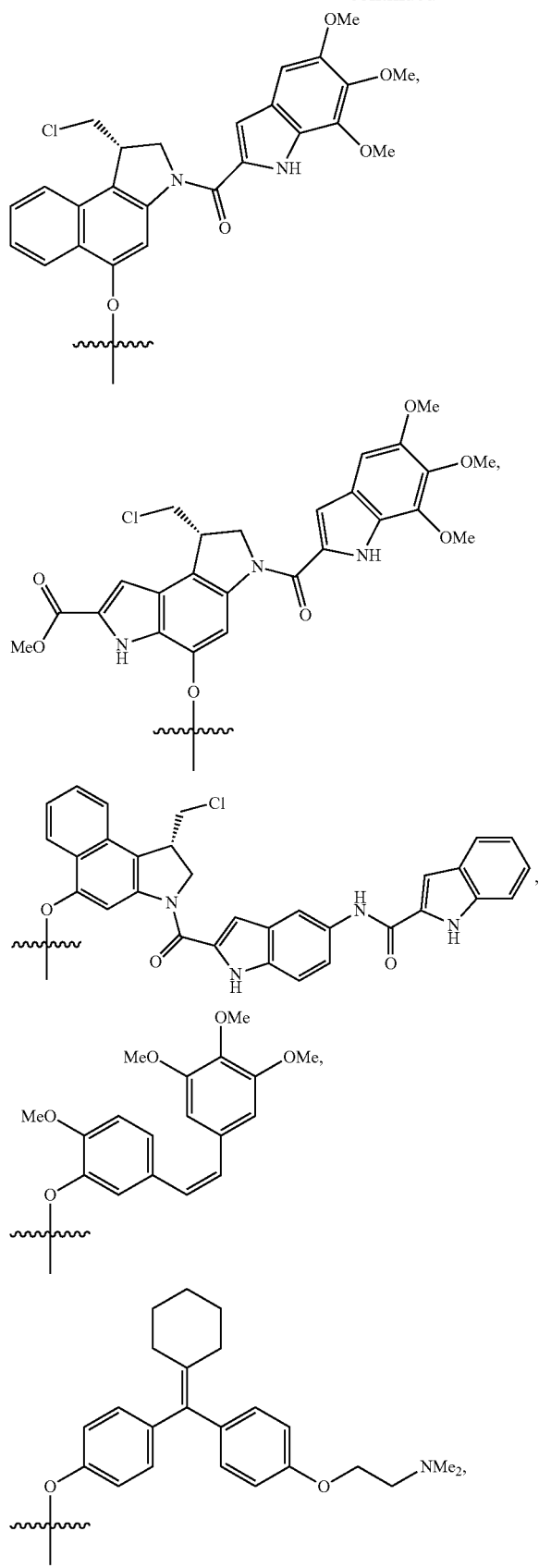

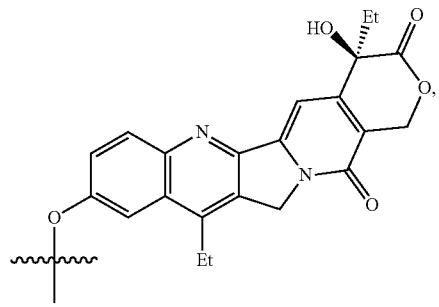
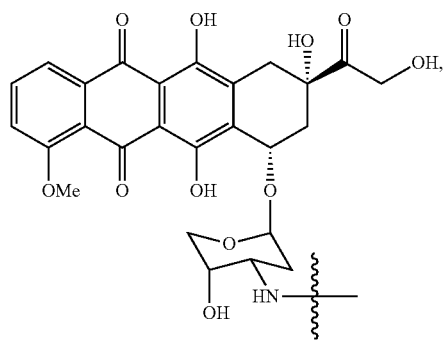
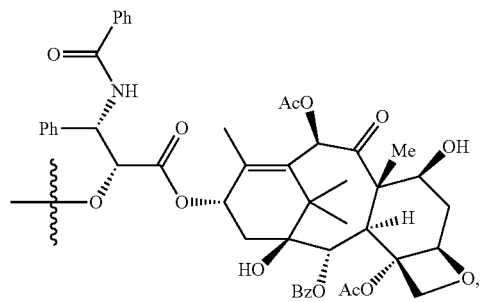
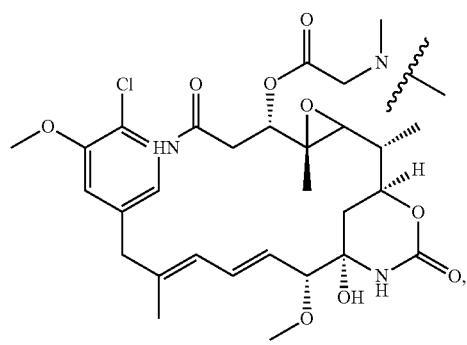
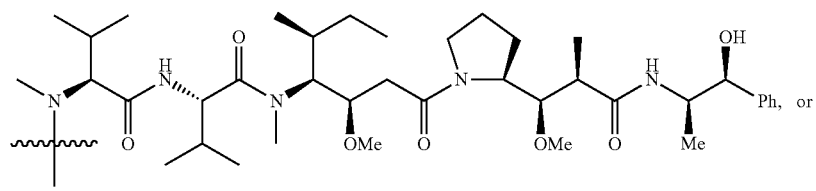

-continued

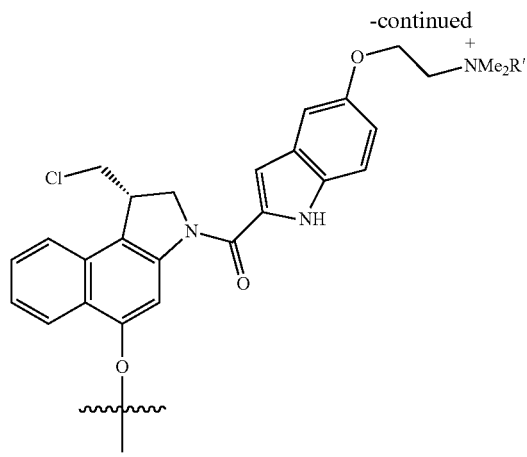

where R' is $C_1$-$C_{10}$ alkyl or alkyl sulfonate.

15. The conjugate according to any one of clauses 1-14, wherein $R^5$ is

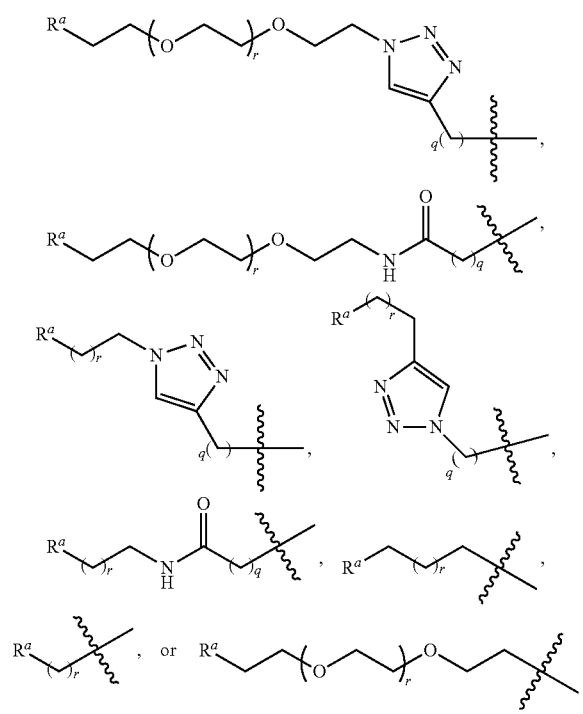

where q and r independently are 1, 2, 3, 4, or 5.

16. The conjugate according to any one of clauses 1-14, wherein $R^5$ is

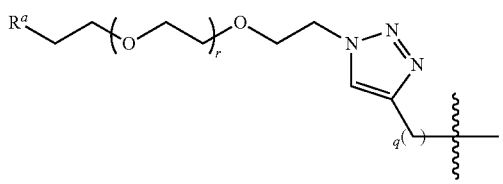

where q and r independently are 1, 2, 3, 4, or 5.

17. The conjugate according to any one of clauses 1-16, wherein $R^b$ is a targeting agent.

18. The conjugate according to any one of clauses 1-17, wherein $R^b$ is an antibody.

19. The conjugate according to any one of clauses 1-18, wherein $R^5$ is —$(CH_2)_x$-$L_2$-$R^a$, where x is an integer≥1, $L_2$ is a linker moiety or is absent, and $R^a$ is —C(O)N(H)$R^b$, —N(H)C(O)$R^b$, —N(H)$R^b$, or —S$R^b$ where $R^b$ is a targeting agent, the conjugate further comprising one or more additional moieties bound to $R^b$, each of the additional moieties independently having a chemical structure according to Formula III:

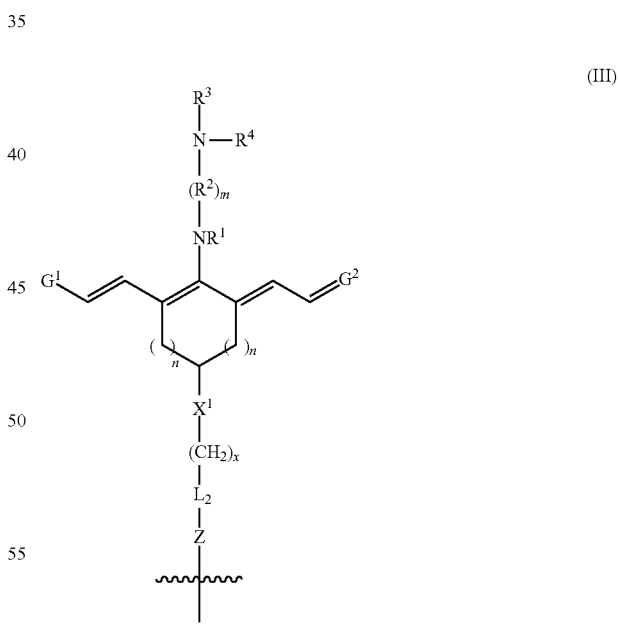

(III)

wherein m, n, x, $R^1$-$R^4$, $X^1$, $G^1$, $G^2$, and $L_2$ are as defined in clause 1, and Z is —C(O)N(H)—, —N(H)C(O)—, —N(H)—, or —S—.

20. The conjugate according to any of clauses 1-19, wherein $R^b$ is an antibody and $R^3$ is

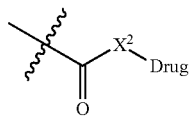

where —X²-Drug is

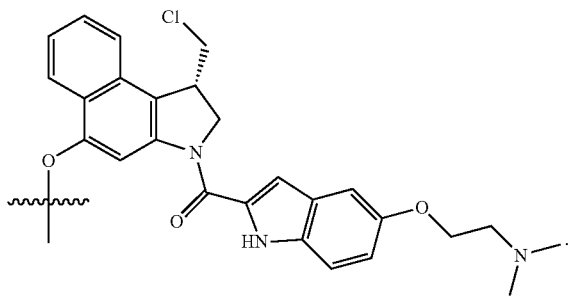 [SMILES: *Oc1cc2c(c3ccccc13)[C@H](CCl)CN2C(=O)c1cc2cc(OCCN(C)C)ccc2[nH]1]

21. The conjugate according to clause 1, wherein the conjugate is:

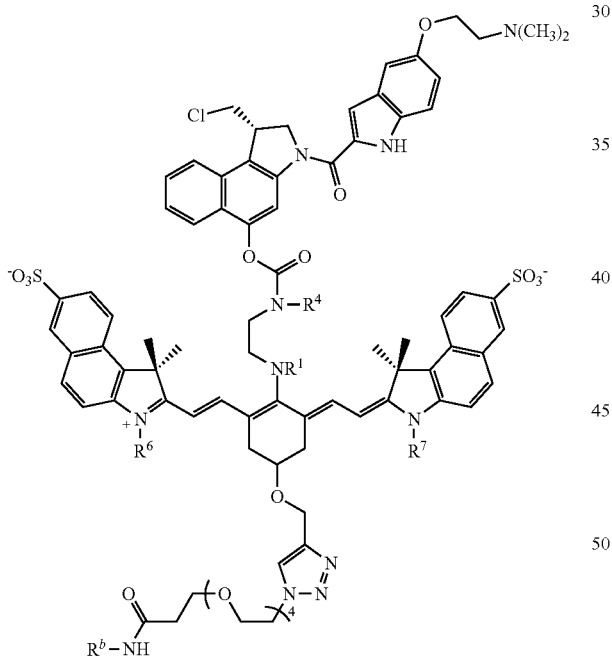

where $R^1$ and $R^4$ are methyl, ethyl, n-propyl, i-propyl, t-butyl, or —(CH$_2$)$_2$OH; $R^6$ and $R^7$ are —(CH$_2$)$_4$SO$_3^-$ or —(CH$_2$)$_4$N(CH$_3$)$_3\pm$; and $R^b$ is an antibody.

22. The conjugate according to clause 21, wherein the antibody is panitumumab or trastuzumab.

23. A pharmaceutical composition comprising a conjugate according to any one of clauses 1-22 wherein $R^b$ is a targeting agent and a pharmaceutically acceptable carrier.

24. A precursor compound having a structure according to Formula IV, or a salt thereof:

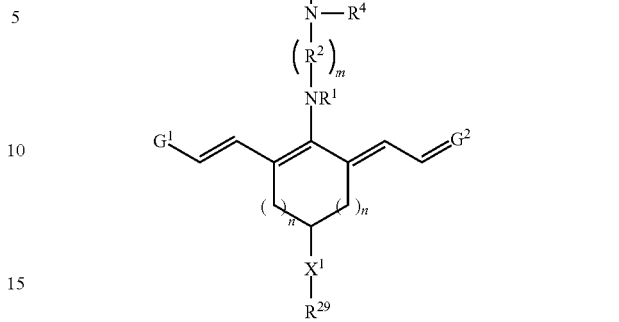

(IV)

wherein m is 1, 2, 3, 4, or 5; each n independently is 1, 2, or 3; $R^1$ and $R^4$ independently are alkyl, haloalkyl, cycloalkyl, alkoxy, —ROH, —RC(O)OH, —C(O)—R, or —C(O)—O—R, wherein R is alkyl; $R^2$ is C($R^c$)$_2$ wherein each $R^c$ independently is H, halo, alkyl, or aryl, or ($R^2$)$_m$ collectively is phenyl; $X^1$ is O, N, or CH$_2$; $G^1$ is

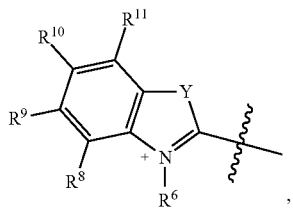

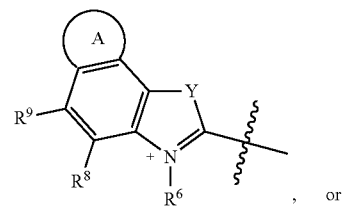

, or

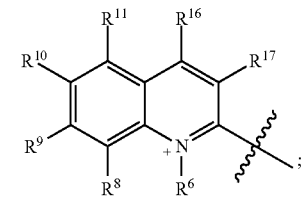

;

$G^2$ is

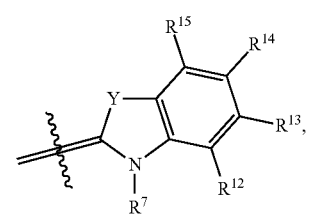

,

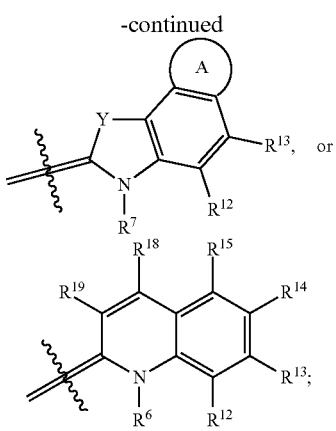

$R^6$ and $R^7$ independently are H, alkyl, alkoxy, alkyl sulfonate, or substituted aminoalkyl; $R^8$-$R^{19}$ independently are H, alkyl, amino, alkoxy, or alkyl sulfonate; each Y independently is $C(R^d)_2$, S, O, Se, or $N(R^d)$ wherein each $R^d$ independently is H or alkyl; each ring A independently is a 6-membered fused aliphatic, heteroaliphatic, aryl, or heteroaryl ring; $R^{28}$ is hydrogen or a protecting group; and $R^{29}$ is —$(CH_2)_u$—C≡CH where u is 1, 2, 3, 4, or 5.

25. The precursor compound of clause 24, wherein $R^{28}$ is hydrogen.

26. The precursor compound of clause 24, wherein the precursor compound is

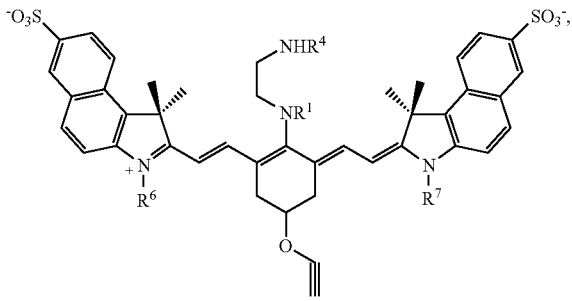

wherein $R^1$ and $R^4$ are methyl, ethyl, n-propyl, i-propyl, t-butyl, or —$(CH_2)_2OH$; and $R^6$ and $R^7$ are —$(CH_2)_pSO_3^-$ or —$(CH_2)_pN(CH_3)_3^+$, where p is 1, 2, 3, 4, or 5.

27. A method, comprising: providing a conjugate according to any one of clauses 1-22, wherein $R^b$ is a targeting agent; and subsequently irradiating the conjugate with targeted application of an effective quantity of light having a selected wavelength in the near-infrared range and a selected intensity to induce a cleavage reaction and release the drug from the conjugate.

28. The method of clause 27, wherein irradiating the conjugate with targeted application of light comprises irradiating the conjugate with a laser that produces light having a wavelength of 650-900 nm.

29. The method of clause 27 or clause 28, further comprising: monitoring a level of fluorescence of the conjugate; and ceasing irradiation when the level of fluorescence falls below a target level.

30. The method of any one of clauses 27-29, further comprising: providing a biological sample including, or suspected of including, a target molecule; contacting the biological sample with the conjugate, wherein the targeting agent of the conjugate is capable of recognizing and binding to the target molecule; and subsequently irradiating the biological sample with the targeted application of light.

31. The method of any one of clauses 27-29, further comprising: identifying a subject as having a condition that may be treated with the drug; administering a therapeutically effective amount of the conjugate or a pharmaceutical composition comprising the conjugate to the subject; and subsequently irradiating the conjugate by targeted application of an effective quantity of light having a wavelength in the near-infrared range and a selected intensity to a targeted portion of the subject, thereby releasing the drug from at least some molecules of the conjugate.

32. The method of clause 31, wherein the subject has a tumor and the targeted portion of the subject includes an area proximate a location of the tumor.

33. The method of clause 32, further comprising excising at least a portion of the tumor from the subject before administering the therapeutically effective amount of the conjugate or the pharmaceutical composition comprising the conjugate to the subject.

34. The method of any one of clauses 31-33, wherein the effective quantity of light applied to the targeted portion is from 5-250 J/cm$^2$.

35. The method of any one of clauses 31-34, wherein the subject has previously been treated unsuccessfully for the condition.

36. A method, comprising: administering a therapeutically effective amount of a conjugate according to any one of clauses 1-22 or a pharmaceutical composition comprising the conjugate to a subject suspected of having a condition that may be treated with the drug; subsequently irradiating the conjugate by targeted application of a quantity of light having a wavelength in the near-infrared range and a selected intensity to a targeted portion of the subject, wherein the quantity of light is sufficient to produce fluorescence of the conjugate but insufficient to induce cleavage of the conjugate and release the drug from the conjugate; detecting any fluorescence from the conjugate in the targeted portion of the subject; and subsequently irradiating the conjugate, if fluorescence is detected, by targeted application of an effective quantity of light having a wavelength in the near-infrared range and a selected intensity to the targeted portion of the subject, thereby releasing the drug from at least some molecules of the conjugate.

37. The method of clause 36, wherein the condition is a tumor that may be treated with the drug and the targeted portion of the subject includes the tumor site, the method further comprising: excising at least a portion of the tumor from the subject before administering the therapeutically effective amount of the conjugate.

38. The method of clause 36, wherein (i) the condition is a tumor that may be treated with the drug, (ii) the targeted portion of the subject includes the tumor site, and (iii) fluorescence is detected in the targeted portion of the subject, the method further comprising: excising at least a portion of the tumor from the subject after detecting the fluorescence in the targeted portion of the subject; and subsequently irradiating the conjugate by targeted application of the effective quantity of light to the targeted portion of the subject.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A precursor compound having a structure according to Formula IV, or a salt thereof:

(IV)

wherein m is 1, 2, 3, 4, or 5;
each n independently is 1, 2, or 3;
$R^1$ and $R^4$ independently are alkyl, haloalkyl, cycloalkyl, alkoxy, —ROH, —RC(O)OH, —C(O)—R, or —C(O)—O—R, wherein R is alkyl;
$R^2$ is $C(R^c)_2$ wherein each $R^c$ independently is H, halo, alkyl, or aryl, or $(R^2)_m$ collectively is phenyl;
$X^1$ is O, N, or $CH_2$;
$G^1$ is , or

;

$G^2$ is

, or

;

$R^6$ and $R^7$ independently are alkyl sulfonate, H, alkyl, alkoxy, or substituted aminoalkyl;
$R^8$-$R^{19}$ independently are H, alkyl, amino, alkoxy, or alkyl sulfonate;
each Y independently is $C(R^d)_2$, S, O, Se, or $N(R^d)$ wherein each $R^d$ independently is alkyl or H;
each ring A independently is a 6-membered fused aryl, aliphatic, heteroaliphatic, or heteroaryl ring;
$R^{28}$ is hydrogen or a protecting group; and
$R^{29}$ is —$(CH_2)_u$—C≡CH where u is 1, 2, 3, 4, or 5.

2. The precursor compound of claim 1, wherein the precursor compound is wherein $R^1$ and $R^4$ are methyl, ethyl, n-propyl, i-propyl, t-butyl, or —$(CH_2)_2OH$; and
$R^6$ and $R^7$ are —$(CH_2)_pSO_3^-$ or —$(CH_2)_pN(CH_3)_3^+$, where p is 1, 2, 3, 4, or 5.

3. The precursor compound of claim 1, wherein $R^{28}$ is hydrogen, tert-butyloxycarbonyl, or 9-fluorenylmethyloxycarbonyl.

4. The precursor compound of claim 1, wherein $R^{28}$ is hydrogen.

5. The precursor compound of claim 1, wherein $R^6$ and $R^7$ independently are alkyl sulfonate or substituted aminoalkyl.

6. The precursor compound of claim 1, wherein $R^6$ and $R^7$ independently are —$(CH_2)_pSO_3^-$ or —$(CH_2)_pN(CH_3)_3^-$, where p is 1, 2, 3, 4, or 5.

7. The precursor compound of claim 1, wherein:
$R^6$ and $R^7$ are —$(CH_2)_4SO_3^-$; or
$R^6$ and $R^7$ are —$(CH_2)_4N(CH_3)_3^+$.

8. The precursor compound of claim 1, wherein $R^8$-$R^{19}$ are H.

9. The precursor compound of claim 1, wherein each Y independently is $C(CH_3)_2$ or S.

10. The precursor compound of claim 1, wherein each Y is $C(CH_3)_2$.

11. The precursor compound of claim 1, wherein each ring A is a fused phenyl ring substituted with —$SO_3^-$.

* * * * *